(12) United States Patent
Johnson et al.

(10) Patent No.: US 10,792,373 B2
(45) Date of Patent: Oct. 6, 2020

(54) DRUG DELIVERY POLYMERS AND USES THEREOF

(71) Applicant: Massachusetts Institute of Technology, Cambridge, MA (US)

(72) Inventors: Jeremiah A. Johnson, Boston, MA (US); Longyan Liao, Midland, MI (US); Jonathan Christopher Barnes, Waltham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/167,412

(22) Filed: Oct. 22, 2018

(65) Prior Publication Data

US 2019/0054187 A1   Feb. 21, 2019

Related U.S. Application Data

(62) Division of application No. 15/616,498, filed on Jun. 7, 2017, now Pat. No. 10,105,449.

(60) Provisional application No. 62/346,923, filed on Jun. 7, 2016.

(51) Int. Cl.
| | |
|---|---|
| *A61K 31/282* | (2006.01) |
| *A61K 33/243* | (2019.01) |
| *C07F 19/00* | (2006.01) |
| *C08G 69/48* | (2006.01) |
| *A61K 47/69* | (2017.01) |
| *A61K 33/00* | (2006.01) |
| *A61K 31/4745* | (2006.01) |
| *A61K 31/704* | (2006.01) |
| *A61K 33/24* | (2019.01) |
| *C07F 15/00* | (2006.01) |

(52) U.S. Cl.
CPC ........ *A61K 47/6935* (2017.08); *A61K 31/282* (2013.01); *A61K 31/4745* (2013.01); *A61K 31/704* (2013.01); *A61K 33/00* (2013.01); *A61K 33/24* (2013.01); *C07F 15/0093* (2013.01); *C08G 69/48* (2013.01)

(58) Field of Classification Search
CPC . A61K 31/282; A61K 33/243; C07F 15/0093; C08G 69/48
See application file for complete search history.

(56) References Cited

U.S. PATENT DOCUMENTS

| | | | |
|---|---|---|---|
| 4,359,425 A | 11/1982 | Totani et al. | |
| 5,811,515 A | 9/1998 | Grubbs et al. | |
| 8,067,505 B2 | 11/2011 | Harris et al. | |
| 9,381,253 B2 | 7/2016 | Johnson et al. | |
| 9,447,129 B2 | 9/2016 | Johnson et al. | |
| 9,822,216 B2 | 11/2017 | Mahanthappa et al. | |
| 10,023,536 B2 | 7/2018 | Johnson et al. | |
| 10,105,449 B2 | 10/2018 | Johnson et al. | |
| 10,159,749 B2 | 12/2018 | Johnson et al. | |
| 2002/0183473 A1 | 12/2002 | Matyjaszewski et al. | |
| 2002/0198328 A1 | 12/2002 | L'Alloret | |
| 2003/0065023 A1 | 4/2003 | Swindell et al. | |
| 2005/0109976 A1 | 5/2005 | Fuchs et al. | |
| 2011/0300219 A1 | 12/2011 | Lippard et al. | |
| 2013/0296491 A1 | 11/2013 | Xia et al. | |
| 2013/0324666 A1 | 12/2013 | Yan et al. | |
| 2014/0308234 A1 | 4/2014 | Johnson et al. | |
| 2014/0142249 A1 | 5/2014 | Cho et al. | |
| 2015/0225438 A1 | 8/2015 | Johnson et al. | |
| 2016/0024246 A1 | 1/2016 | Mahanthappa et al. | |
| 2016/0289392 A1 | 10/2016 | Grubbs et al. | |
| 2016/0296631 A1 | 10/2016 | Johnson et al. | |
| 2016/0361702 A1 | 12/2016 | Cohen et al. | |
| 2017/0000909 A1 | 1/2017 | Gianneschi et al. | |
| 2017/0073311 A1 | 3/2017 | Johnson et al. | |
| 2017/0348431 A1 | 12/2017 | Johnson et al. | |
| 2018/0030213 A1 | 2/2018 | Johnson et al. | |
| 2018/0036415 A9 | 2/2018 | Johnson et al. | |
| 2018/0094099 A1 | 4/2018 | Johnson et al. | |
| 2019/0030067 A1 | 1/2019 | Johnson et al. | |
| 2019/0038751 A1 | 2/2019 | Johnson et al. | |
| 2019/0038782 A1 | 2/2019 | Johnson et al. | |
| 2019/0192672 A1 | 6/2019 | Johnson et al. | |

FOREIGN PATENT DOCUMENTS

| | | |
|---|---|---|
| CN | 101412792 A | 4/2009 |
| KR | 20120113694 A | 10/2012 |
| WO | WO 2010/047765 A2 | 4/2010 |
| WO | WO 2013/169739 A1 | 11/2013 |
| WO | WO 2014/169073 A1 | 10/2014 |
| WO | WO 2016/023036 A1 | 2/2016 |

OTHER PUBLICATIONS

International Search Report and Written Opinion for PCT/US2017/036447, dated Sep. 7, 2018.
International Preliminary Report on Patentability for Application No. PCT/US2017/036447 dated Dec. 20, 2018.
International Search Report and Written Opinion for Application No. PCT/US/2018/040496 dated Jan. 14, 2019.
International Search Report and Written Opinion for PCT/US2018/040488, dated Oct. 15, 2018.
International Search Report and Written Opinion for PCT/US2018/040494, dated Oct. 10, 2018.
International Search Report and Written Opinion for PCT/US2017/064784, dated Mar. 1, 2018.
Extended European Search Report for EP 14782253.0, dated Nov. 11, 2016.

(Continued)

*Primary Examiner* — Brenda L Coleman
(74) *Attorney, Agent, or Firm* — Wolf, Greenfield & Sacks, P.C.

(57) ABSTRACT

Described herein are platinum-based brush-arm star polymers (Pt-BASPs), or a pharmaceutical composition thereof, for delivery of platinum-based agents, such as oxaliplatin. Also provided are methods and kits involving the Pt-BASPs, or a pharmaceutical composition thereof, for treating proliferative diseases such as cancers (e.g., lung cancer, head-and-neck cancer, esophagus cancer, stomach cancer, breast cancer, pancreas cancer, colorectal cancer, liver cancer, kidney cancer, or prostate cancer) in a subject.

31 Claims, 40 Drawing Sheets
(40 of 40 Drawing Sheet(s) Filed in Color)

(56) References Cited

OTHER PUBLICATIONS

International Search Report and Written Opinion for PCT/US2014/033554, dated Aug. 29, 2014.
International Preliminary Report on Patentability for PCT/US2014/033554, dated Oct. 22, 2015.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328, 2004.
Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol-yne core functionalization/crosslinking of block copolymer micelles. Polym. Chem., 2011;2:21180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996;120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR to Compare PEG-branch-nitroxide "Bivalent-Brush Polymers" and Traditional PEG Bottle-Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.
Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.
Campos-Fernández et al., Fine-tuning the ring-size of metallacyclophanes: a rational approach to molecular pentagons. J Am Chem Soc. Jan. 31, 2001;123(4):773-4.
Caravan et al., Gadolinium(III) Chelates as MRI Contrast Agents: Structure, Dynamics, and Applications. Chem Rev. Sep. 8, 1999;99(9):2293-352.

(56) References Cited

OTHER PUBLICATIONS

Castilla et al., Stereochemistry in subcomponent self-assembly. Acc Chem Res. Jul. 15, 2014;47(7):2063-73. doi: 10.1021/ar5000924. Epub May 2, 2014.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheon et al., Synergistically integrated nanoparticles as multimodal probes for nanobiotechnology. Acc Chem Res. Dec. 2008;41(12):1630-40. doi: 10.1021/ar800045c.

Chifotides et al., Anion-π interactions in supramolecular architectures. Acc Chem Res. Apr. 16, 2013;46(4):894-906. doi: 10.1021/ar300251k. Epub Mar. 11, 2013.

Choi et al., Self-confirming "AND" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Dag et al., Three-arm star ring opening metathesis polymers via alkyne-azide click reaction. J. Polym. Sci. A Polym. Chem., 47: 2344-2351. doi:10.1002/pola.23324, 2009.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.

Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan, The dawning era of polymer therapeutics. Nat Rev Drug Discov. May 2003;2(5):347-60.

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Fullenkamp et al., Mussel-Inspired Histidine-Based Transient Network Metal Coordination Hydrogels. Macromolecules. Jan. 18, 2013;46(3):1167-1174.

Gao et al., Development of star polymers as unimolecular containers for nanomaterials. Macromol Rapid Commun. May 14, 2012;33(9):722-34. doi: 10.1002/marc.201200005. Epub Mar. 14, 2012.

Gao et al., Modular Approaches to Star and Miktoarm Star Polymers by ATRP of Cross-Linkers. Macromol. Symp., 291-292: 12-16. doi:10.1002/masy.201050502, 2010.

Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.

Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125.

Ge et al., A Pyrene-functionalized Polynorbornene for Ratiometric Fluorescence Sensing of Pyrophosphate. Chem. Asian J. 2016;11:687.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Glunde et al., Magnetic resonance spectroscopy in metabolic and molecular imaging and diagnosis of cancer. Chem Rev. May 12, 2010;110(5):3043-59. doi: 10.1021/cr9004007.

Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.

(56) References Cited

OTHER PUBLICATIONS

Greenwald et al., Effective drug delivery by PEGylated drug conjugates. Adv Drug Deliv Rev. Feb. 10, 2003;55(2):217-50.

Gumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Haddleton et al., Well-defined oligosaccharide-terminated polymers from living radical polymerization. Biomacromolecules. 2000 Summer;1(2):152-6.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition-fragmentation chain transfer agents: Syntheses and polymerization. J. Polym. Sci. A Polym. Chem., 2004;42:5877-5890. doi:10.1002/pola.20434.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi:10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jamieson et al., Structure, Recognition, and Processing of Cisplatin-DNA Adducts. Chem Rev. Sep. 8, 1999;99(9):2467-98.

Jesberger et al., Hyperbranched polymers as scaffolds for multifunctional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

(56) References Cited

OTHER PUBLICATIONS

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs. 6b07670. Epub Sep. 1, 2016.

Kean et al., Increasing the maximum achievable strain of a covalent polymer gel through the addition of mechanically invisible cross-links. Adv Mater. Sep. 10, 2014;26(34):6013-8. doi: 10.1002/adma. 201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14. With Supporting Information. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel. 2013.03.016. Epub Mar. 29, 2013.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02. 040. Epub Mar. 21, 2009.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci. 2009.11.002.

Leininger et al., Self-assembly of discrete cyclic nanostructures mediated by transition metals. Chem Rev. Mar. 8, 2000;100(3):853-908.

Li et al., Polycatechol Nanoparticle MRI Contrast Agents. Small, 2016;12(5):668-677. https://doi.org/10.1002/smll.201502754.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Li et al., Surface Properties of Bottlebrush Polymer Thin Films. Macromolecules. 2012;45(17):7118-7127.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Liao et al., A Convergent Synthetic Platform for Single-Nanoparticle Combination Cancer Therapy: Ratiometric Loading and Controlled Release of Cisplatin, Doxorubicin, and Camptothecin. J. Am. Chem. Soc., 2014;136(16):5896-5899. DOI: 10.1021/ja502011g.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 4, 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm. 2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc. 201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805.

(56) References Cited

OTHER PUBLICATIONS

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366, 2009.

Nair et al., Modulating mechanical properties of self-assembled polymer networks by multi-functional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer as the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197, 2001.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

(56) References Cited

OTHER PUBLICATIONS

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik, 86: 2195-2214. doi:10.1002/cite.201400088, 2014.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

Rzayev et al., Molecular Bottlebrushes: New Opportunities in Nanomaterials Fabrication. ACS Macro Lett., 2012;1(9):1146-1149. DOI: 10.1021/mz300402x.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001, 2003.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multi-modal imaging. Chem Soc Rev. Jul. 21, 2015;44(14):4501-16. doi: 10.1039/c4cs00345d.

Skomski et al., Redox-active on-surface assembly of metal-organic chains with single-site Pt(II). * J Am Chem Soc. Jul. 16, 2014;136(28):9862-5. doi: 10.1021/ja504850f. Epub Jul. 1, 2014.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications2014;5:Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Coordination-directed assembly of trigonal and tetragonal molecular boxes encapsulating anionic guests. Journal of the Chemical Society, Dalton Transactions. 2001:359-361. doi: 10.1039/B010118O.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Thompson et al., Labelling polymers and micellar nanoparticles via initiation, propagation and termination with ROMP. Polym. Chem., 2014;5:1954-1964.

(56) References Cited

OTHER PUBLICATIONS

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.
Tolmasoff et al., Superoxide dismutase: correlation with life-span and specific metabolic rate in primate species. Proc Natl Acad Sci U S A. May 1980;77(5):2777-81.
Tominaga et al., Finite, spherical coordination networks that self-organize from 36 small components. Angew Chem Int Ed Engl. Oct. 25, 2004;43(42):5621-5.
Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.
Tsuji et al., Facile Palladium catalyzed decarboxylative allylation of active methylene compounds under neutral conditions using allylic carbonates. Tetrahedron Letters. 1982;23(46):4809-12.
Tu et al., Multimodal magnetic-resonance/optical-imaging contrast agent sensitive to NADH. Angew Chem Int Ed Engl. 2009;48(35):6547-51. doi: 10.1002/anie.200900984.
Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284, 2004.
Valeur et al., Amide bond formation: beyond the myth of coupling reagents. Chem. Soc. Rev., 2009;38:606-631. DOI: 10.1039/B701677H.
Verduzco et al., Correction: Structure, function, self-assembly, and applications of bottlebrush copolymers. Chem Soc Rev. Nov. 7, 2015;44(21):7916. doi: 10.1039/c5cs90099a.
Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.
Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.
Wang et al., Advances of cancer therapy by nanotechnology. Cancer Res Treat. Mar. 2009;41(1):1-11. doi: 10.4143/crt.2009.41.1.1. Epub Mar. 31, 2009.
Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].
Wei et al., Exceedingly small iron oxide nanoparticles as positive MRI contrast agents. Proc. Natl. Acad. Sci. USA 2017;114(9):2325-2330.
Weng et al., Control of Gel Morphology and Properties of a Class of Metallo-Supramolecular Polyers by Good/Poor Solvent Environments. Macromolecules. 2009;42(1):236-246.
Weng et al., Effect of monomer structure on the gelation of a class of metallo-supramolecular polymers. Soft Matter. 2009;5(23):4647-4657.
Weng et al., Structural origin of the thixotropic behavior of a class of metallosupramolecular gels. Tetrahedron. Jul. 30, 2007;63(31):7419-7431.
Weng et al., Understanding the mechanism of gelation and stimuli-responsive nature of a class of metallo-supramolecular gels. J Am Chem Soc. Sep. 6, 2006;128(35):11663-72.
Westhaus et al., Triggered release of calcium from lipid vesicles: a bioinspired strategy for rapid gelation of polysaccharide and protein hydrogels. Biomaterials. Mar. 2001;22(5):453-62.
Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.
Wong et al., Quantitative formation of core cross-linked star polymers via a one-pot two-step single electron transfer-living radical polymerization. Polym. Chem., 2013;4:4562-4565. DOI: 10.1039/C3PY00726J.
Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.
Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.
Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.
Xia et al., EPR study of spin labeled brush polymers in organic solvents. J Am Chem Soc. Dec. 14, 2011;133(49):19953-9. doi: 10.1021/ja2085349. Epub Nov. 21, 2011.
Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. EpubAug. 28, 2012.
Xing et al., A stable metal coordination polymer gel based on a calix[4]arene and its 'uptake' of non-ionic organic molecules from the aqueous phase. Chem Commun (Camb). Feb. 21, 2002;(4):362-3.
Xing et al., Design of coordination polymer as stable catalytic systems. Chemistry. Nov. 4, 2002;8(21):5028-32.
Xing et al., Spontaneous Enrichment of Organic Molecules from Aqueous and Gas Phases into a Stable Metallogel. Langmuir. 2002;18:9654-9658.
Xu et al., Mechanism of Shear Thickening in Reversibly Cross-linked Supramolecular Polymer Networks. Macromolecules. Apr. 13, 2010;43(7):3556-3565.
Xu et al., Scaling Laws in Supramolecular Polymer Networks. Macromolecules. 2011;44(13):5465-5472.
Xu et al., Strain Hardening and Strain Softening of Reversibly Cross-linked Supramolecular Polymer Networks. Macromolecules. Sep. 27, 2011;44(18):7478-7488.
Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. EpubAug. 8, 2013.
Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yang et al., Luminescent chemodosimeters for bioimaging. Chem Rev. Jan. 9, 2013;113(1):192-270. doi: 10.1021/cr2004103. Epub Jun. 18, 2012.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.
Yount et al., Small-molecule dynamics and mechanisms underlying the macroscopic mechanical properties of coordinatively cross-linked polymer networks. J Am Chem Soc. Oct. 19, 2005;127(41):14488-96.

(56) References Cited

OTHER PUBLICATIONS

Yount et al., Strong means slow: dynamic contributions to the bulk mechanical properties of supramolecular networks. Angew Chem Int Ed Engl. Apr. 29, 2005;44(18):2746-8.

Yue et al., Macrocyclic and lantern complexes of palladium(II) with bis(amidopyridine) ligands: synthesis, structure, and host-guest chemistry. Inorg Chem. Nov. 29, 2004;43(24):7671-81.

Zhang et al., Active cross-linkers that lead to active gels. Angew Chem Int Ed Engl. Oct. 25, 2013;52(44):11494-8. doi: 10.1002/anie.201304437. Epub Sep. 12, 2013.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.

Zhang et al., Redox-Responsive, Core Cross-Linked Polyester Micelles. ACS Macro Lett., 2013;2(1):40-44. DOI: 10.1021/mz300522n.

Zhao et al., Rheological Behavoir of Shear-Responsive Metallo-Supramolecular Gels. Macromolecules. 2004;37(10):3529-3531.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.

Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.

Zhou et al., Counting primary loops in polymer gels. Proc Natl Acad Sci U S A. Nov. 20, 2012;109(47):19119-24. doi: 10.1073/pnas.1213169109. Epub Nov. 6, 2012.

Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.

U.S. Appl. No. 15/725,036, filed Oct. 4, 2017, Johnson et al.
U.S. Appl. No. 16/080,503, filed Aug. 28, 2018, Johnson et al.
PCT/US2018/040496, Jan. 14, 2019, International Search Report and Written Opinion.
International Search Report and Written Opinion for PCT/US2017/055145, dated Jan. 23, 2018.
International Preliminary Report on Patentability for PCT/US2017/055145, dated Apr. 18, 2019.
International Preliminary Report on Patentability for PCT/US2017/064784, dated Jun. 20, 2019.
International Search Report for PCT/US2017/48641, dated Nov. 9, 2017.
International Preliminary Report on Patentability for Application No. PCT/US2017/48641 dated Mar. 7, 2019.
Invitation to Pay Additional Fees for PCT/US2018/040496, dated Nov. 21, 2018.

Bates et al., Polarity-switching top coats enable orientation of sub-10-nm block copolymer domains. Science. Nov. 9, 2012;338(6108):775-9. doi: 10.1126/science.1226046.

Bohbot-Raviv et al., Discovering new ordered phases of block copolymers. Phys Rev Lett. Oct. 16, 2000;85(16):3428.

Bolton et al., Synthesis and Melt Self-Assembly of PS-PMMA-LA Triblock Bottlebrush Copolymers. Macromolecules, 2014;47(9):2864-74. DOI: 10.1021/ma500625k.

Cheng et al., Well-defined diblock macromonomer with a norbornene group at block junction: anionic living linking synthesis and ring-opening metathesis polymerization. Macromol. Mar. 4, 2010;43(7):3153-5.

Dalsin et al., Bottlebrush block polymers: Quantitative theory and experiments. ACS Nano. Nov. 6, 2015;9(12):12233-45.

Davis et al., Atom transfer radical polymerization of tert-butyl acrylate and preparation of block copolymers. Macromol. May 30, 2000;33(11):4039-47.

Frechet, Functional polymers and dendrimers: reactivity, molecular architecture, and interfacial energy. Science. Mar. 25, 1994;263(5154):1710-5.

Gestwicki et al., Influencing receptor-ligand binding mechanisms with multivalent ligand architecture. J Am Chem Soc. Dec. 18, 2002;124(50):14922-33.

Grason et al., Geometric theory of diblock copolymer phases. Phys Rev Lett. Jul. 31, 2003;91(5):058304. 4 pages.

Gu et al., PolyMOF Nanoparticles: Dual Roles of a Multivalent polyMOF Ligand in Size Control and Surface Functionalization. Angewandte Chemie Int. Ed. 2019;58:2-8. Epub Sep. 10, 2019.

Hawker et al., Preparation of polymers with controlled molecular architecture. A new convergent approach to dendritic macromolecules. J Am Chem Soc. Oct. 1990;112(21):7638-47.

Heroguez et al., Novel Styrene-Butadiene Copolymers by Ring-Opening Metathesis Polymerization. Macromol. Oct. 3, 2000;33(20):7241-8.

Hoogenboom et al., 1-Lactide Polymerization Utilizing a Hydroxy-Functionalized 3,6-Bis(2-pyridyl)pyridazine as Supramolecular (Co)initiator: Construction of Polymeric [2×2] Grids. Macromolecules, 2003;36(13):4743-9. DOI: 10.1021/ma034119e.

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.

Jeong et al., Highly tunable self-assembled nanostructures from a poly (2-vinylpyridine-b-dimethylsiloxane) block copolymer. Nano Lett. Sep. 27, 2011;11(10):4095-101.

Jiang et al., Morphology and Phase Diagram of Comb Block Copolymer Am+ 1 (BC) m. J Phys Chem B. May 7, 2009;113(21):7462-7.

Jung et al., Orientation-controlled self-assembled nanolithography using a polystyrene-polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kawamoto et al., Loops versus branch functionality in model click hydrogels. Macromol. Dec. 1, 2015;48(24):8980-8.

Lee et al., Novel phase morphologies in a microphase-separated dendritic polymer melt. Macromol. Jan. 12, 2009;42(3):849-59.

Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.

Li et al., Dynamic cylindrical assembly of triblock copolymers by a hierarchical process of covalent and supramolecular interactions. J Am Chem Soc. Jan. 4, 2011;133(5):1228-31.

Li et al., Efficient synthesis of narrowly dispersed amphiphilic double-brush copolymers through the polymerization reaction of macromonomer micelle emulsifiers at the oil-water interface. Polym Chem. 2016;7(27):4476-85.

Li et al., Facile syntheses of cylindrical molecular brushes by a sequential RAFT and ROMP "grafting-through" methodology. J Polym Sci A Polym Chem. Oct. 15, 2009;47(20):5557-5563.

(56) References Cited

OTHER PUBLICATIONS

Li et al., Synthesis of Hetero-Grafted Amphiphilic Diblock Molecular Brushes and Their Self-Assembly in Aqueous Medium. Macromolecules. 2010;43(3):1182-1184.

Li et al., Well-defined amphiphilic double-brush copolymers and their performance as emulsion surfactants. Macromol. May 18, 2012;45(11):4623-9.

Luo et al., Toroidal structures from brush amphiphiles. Chem Commun. 2014;50(5):536-8.

Rangadurai et al., Temporal and triggered evolution of host-guest characteristics in amphiphilic polymer assemblies. J Am Chem Soc. Jun. 10, 2016;138(24):7508-11.

Runge et al., "Synthesis and Self-Assembly of Bottlebrush Block Copolymers" PMSEPreprints, 2005, 92, 5-6.

Rzayev, Synthesis of polystyrene-polylactide bottlebrush block copolymers and their melt self-assembly into large domain nanostructures. Macromol. Feb. 20, 2009;42(6):2135-41.

Sinturel et al., High $\chi$-low N block polymers: how far can we go?. ACS Macro Lett. Sep. 2, 2015;4:1044-50.

Theodorakis et al., Interplay between chain collapse and microphase separation in bottle-brush polymers with two types of side chains. Macromol. May 4, 2010;43(11):5137-48.

Verduzco et al., Structure, function, self-assembly, and applications of bottlebrush copolymers. Chem. Soc. Rev., 2015;44:2405-20.

Yuan et al., One-pot syntheses of amphiphilic centipede-like brush copolymers via combination of ring-opening polymerization and "click" chemistry. Macromol. Jan. 27, 2010;43(4):1739-46.

Zhao et al., Polystyrene-Polylactide Bottlebrush Block Copolymer at the Air/Water Interface. Macromol. Sep. 28, 2009;42(22):9027-33.

Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.

Zheng et al., Morphology of ABC triblock copolymers. Macromol. Oct. 1995;28(21):7215-23.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

3-Drug BASPs: CPT-OxPt-Dilute DOX (0.2 %)

Diameter (TEM) = 44.5 ± 13.5

1-Drug BASPs: CPT-AcetalXL

Diameter (TEM) = 47.9 ± 10.8 nm $D_H$ = 64 ± 41

1-Drug BASPs: DOX-AcetalXL

Diameter (TEM) = 38.7 ± 9.4 nm
$D_H$ = 44 ± 12

No-Drug BASPs: PEG-AcetalXL

Diameter (TEM) = 51.9 ± 9.3 nm
$D_H$ = 30 ± 12

Diameter (TEM) = 44.5 ± 13.5

Stained with $UO_2(OAc)_2$

DRUG DELIVERY POLYMERS AND USES THEREOF

RELATED APPLICATION

This application is a divisional of and claims priority under 35 U.S.C. § 120 to U.S. application, U.S. Ser. No. 15/616,498, filed Jun. 7, 2017, which claims priority under 35 U.S.C. § 119(e) to U.S. provisional application, U.S. Ser. No. 62/346,923, filed Jun. 7, 2016, each of which is incorporated herein by reference.

FIELD OF THE INVENTION

This invention relates to polymers and macromolecules for the delivery of therapeutic agents and methods of treating diseases.

BACKGROUND OF THE INVENTION

Platinum-based therapeutics form a cornerstone of treatment for solid tumor malignancies. Cisplatin is one of the most effective chemotherapeutic agents against many forms of cancer including testicular cancer, bladder cancer, head and neck cancers, ovarian cancer, breast cancer, lung cancer, prostate cancer, and refractory non-Hodgkin's lymphomas (Jamieson et al., Chem Rev., 1999, 99:2467-2498). Despite the extensive use of cisplatin in oncology, this drug is associated with significant dose-limiting toxicities including nephrotoxicity and neurotoxicity (Dhar et al., Proc. Nat. Acad. Sci., 2011, 1850-1855). Significant efforts have been devoted to developing new strategies for safer and more effective platinum-based therapeutics.

Targeting controlled release polymer systems (e.g., targeted to a particular tissue or cell type or targeted to a specific diseased tissue but not normal tissue) is desirable because it reduces the amount of a drug present in tissues of the body that are not targeted (e.g., healthy tissue). This is particularly important when treating cancer where it is desirable that a cytotoxic dose of the drug be delivered to cancer cells without killing the surrounding non-cancerous tissue. Effective drug targeting can reduce the undesirable and sometimes life threatening side effects common with many anti-cancer therapies. Controlled release polymer systems can be designed to provide a drug level in the optimum range over a longer period of time, thus increasing the efficacy of the drug and minimizing problems with patient compliance.

SUMMARY OF THE INVENTION

Platinum-based agents play an important role in the treatment of cancer. Significant adverse reactions related to platinum-based agents frequently hinders the use of higher doses to achieve their maximum antineoplastic effects. International Application No. PCT/US2014/033554 filed Apr. 9, 2014, describes cisplatin-based brush-arm star polymers (BASPs) using "brush-first" ring-opening metathesis polymerization (ROMP). The present invention provides oxaliplatin or a derivative thereof-based BASPs and their use in the delivery and controlled release of oxliplatin. In certain embodiments, the BASPs can be loaded with oxaliplatin or a derivative thereof and one or more therapeutic, diagnostic, or prophylactic agents for multi-agent delivery. In certain embodiments, the BASPs can be loaded with a bis-norbornene oxaliplatin derivative (e.g., oxPt-XL), irinotecan (IRT), and 5-fluorouracil (5FU).

In one aspect, the present invention provides platinum complexes of Formula (I):

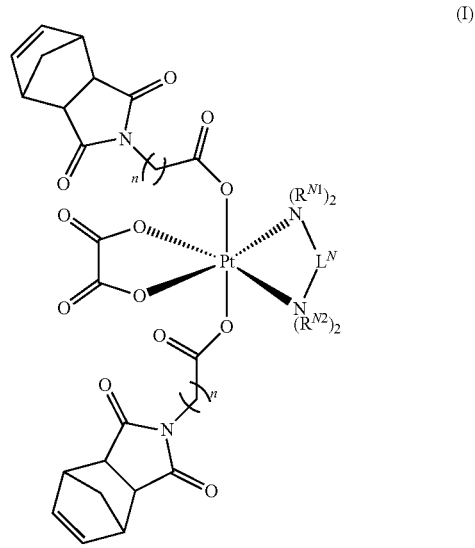

(I)

and salts thereof. In certain embodiments, the platinum complexes of Formula (I), and salts thereof, are prodrugs of a oxaliplatin-based therapeutic agent. In certain embodiments, the platinum complexes of Formula (I), and salts thereof, are used as crosslinkers to prepare Pt-BASPs for the delivery of oxaliplatin. In certain embodiments, an oxaliplatin-based platinum complex crosslinker is incorporated in BASPs. In certain embodiments, an oxaliplatin-based platinum complex crosslinker and a macromonomer containing a therapeutic agent are incorporated in the Pt-BASPs (see FIG. 1).

In another aspect, the present invention provides methods of preparing platinum complexes of Formula (I) and salts thereof. In certain embodiments, the platinum therapeutic agent (e.g., oxaliplatin or a derivative thereof) is oxidized with an oxidant such as hydrogen peroxide, followed by treatment with a norbornene anhydride derivative.

In another aspect, the present invention provides platinum-based brush-arm star polymers (Pt-BASP) using "brush-first" ring-opening metathesis polymerization (ROMP). In certain embodiments, the Pt-BASP described herein can be prepared by (a) reacting a macromonomer of Formula (III') (e.g., Formula (III)) with a metathesis catalyst to form a polymerization mixture; and (b) contacting the polymerization mixture from step (a) with a platinum complex of Formula (I) (e.g., a solution of a platinum complex of Formula (I)). In certain embodiments, the polymer is a brush-arm star polymer (BASP) with the covalently bound platinum-based agent as the core and poly(ethylene glycol) (PEG) as the coronas. In certain embodiments, the macromonomer can introduce one or more therapeutic, diagnostic, or prophylactic agents in addition to the platinum-based agent (e.g., oxaliplatin or a derivative thereof). In certain embodiments, the delivery of an agent (including a platinum-based agent such as oxaliplatin or a derivative thereof) included in a Pt-BASP described herein is ratiometric. In certain embodiments, the delivery of each agent included in a Pt-BASP described herein is ratiometric. In certain embodiments, the release of two or more agents (including oxaliplatin or a derivative thereof) included in a Pt-BASP described herein from the Pt-BASP is orthogonal. In certain embodiments, the delivery of two or more agents (including oxaliplatin or a derivative thereof) included in a Pt-BASP described herein is orthogonal. In certain embodiments, the macromonomer introduces one or more anti-cancer agents for combination delivery. In certain embodiments, the provided Pt-BASPs are loaded with more than one therapeutic, diagnostic, or prophylactic agents and can be prepared by (a) reacting a macromonomer of Formula (III') (e.g., Formula (III)) having one therapeutic, diagnostic, or prophylactic agent, with another macromonomer of Formula (III') (e.g., Formula (III)) having a different therapeutic, diagnostic, or prophylactic agent, in the presence of a metathesis catalyst to form a polymerization mixture; and (b) contacting the polymerization mixture from step (a) with a platinum complex of Formula (I) (e.g., a solution of a platinum complex of Formula (I)). In certain embodiments, the Pt-BASPs as described herein are loaded with oxaliplatin or a derivative thereof, IRT, and 5FU. In certain embodiments, the Pt-BASPs as described herein are loaded with oxaliplatin or a derivative thereof, SN-38, and 5FU.

In another aspect, the present invention provides pharmaceutical compositions comprising a polymer described herein and a pharmaceutically acceptable excipient. In certain embodiments, a polymer described herein is provided as a polymeric nanoparticle. The size of the polymeric nanoparticle may be determined by the molar ratio of all the macromonomers to the crosslinker employed in a method of preparing the polymeric nanoparticle (e.g., Method A' or B', such as Method A or B). In certain embodiments, the polymeric nanoparticle is of radius size of about 1 nm to about 1000 nm. In certain embodiments, the polymeric nanoparticle is of radius size of about 1 nm to about 200 nm. In certain embodiments, the polymeric nanoparticle is of radius size of about 1 nm to about 20 nm. In certain embodiments, the polymeric nanoparticle is of radius size of about 1 nm to about 10 nm. In certain embodiments, the pharmaceutical compositions described herein include a therapeutically effective amount of a polymer described herein. The pharmaceutical composition may be useful for treating a proliferative disease such as cancer.

In another aspect, the present invention provides methods for treating proliferative diseases. Exemplary proliferative diseases include cancers (e.g., leukemia, melanoma, multiple myeloma, solid tumors), benign neoplasms, angiogenesis, angiogenesis-associated diseases, inflammatory diseases, autoinflammatory diseases, and autoimmune diseases. In certain embodiments, the cancer is colorectal cancer. In certain embodiments, the cancer is pancreatic cancer. In certain embodiments, the cancer is metastatic pancreatic cancer.

In another aspect, the present invention provides kits comprising a platinum complex of Formula (I) and/or a polymer described herein. The kits of the invention may include a single dose or multiple doses of a platinum complex of Formula (I) and/or a polymer described herein. The provided kits may be useful for the treatment of proliferative diseases such as cancers. In certain embodiments, the kits described herein further include instructions for administering the platinum complex of Formula (I) and/or a polymer described herein. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ is a single bond where the stereochemistry of the moieties immediately attached thereto is not specified, - - - is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

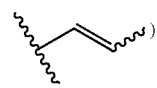

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkynyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-4}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, cycloalkylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_3$-10 carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N ($R^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{aa}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N$(R^{bb})_2$, —C(=$NR^{bb}$)$R^{aa}$, —C(=$NR^{bb}$)$OR^{aa}$, —C(=$NR^{bb}$)N$(R^{bb})_2$, —S(=O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(=O)$(R^{aa})_2$, —P(=O)$(OR^{cc})_2$, and —P(=O)$(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, o-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(=O)$SR^{aa}$, —C(=O)$R^{aa}$, —$CO_2R^{aa}$, —C(=O)$N(R^{bb})_2$, —C(=$NR^{bb}$)$R^{aa}$, —C(=$NR^{bb}$)$OR^{aa}$, —C(=$NR^{bb}$)$N(R^{bb})_2$, —S(=O)$R^{aa}$, —$SO_2R^{aa}$, —Si$(R^{aa})_3$, —P$(R^{cc})_2$, —P$(R^{cc})_3^+X^-$, —P$(OR^{cc})_2$, —P$(OR^{cc})_3^+X^-$, —P(=O)$(R^{aa})_2$, —P(=O)$(OR^{cc})_2$, and —P(=O)$(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HCO$_3^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4^-$, B(C$_6$F$_5$)$_4^-$, BPh$_4^-$, Al(OC(CF$_3$)$_3$)$_4^-$, and carborane anions (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$CCH$_3$)— includes one chain atom C$^A$, one hydrogen atom on C$^A$, and non-chain substituent —(C$^B$H$_2$CCH$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

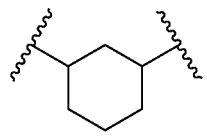 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C═C and/or C≡C bonds anywhere in the hydrocarbon chain. For instance, —CH═CH—(CH$_2$)$_2$—, —CH$_2$—C≡C—CH$_2$—, and —C≡C—CH═CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

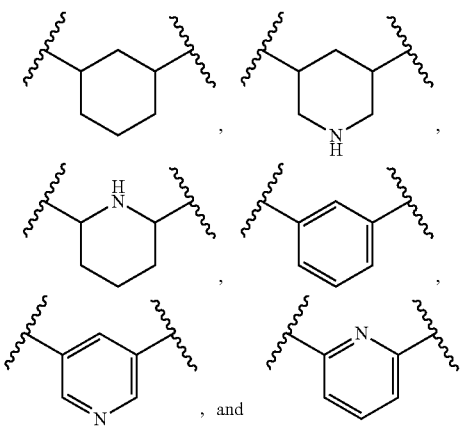

are all examples of a hydrocarbon chain. In contrast, in certain embodiments,

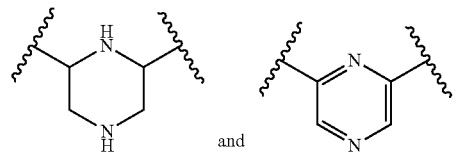 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

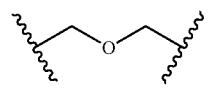 [SMILES: *COC*]

is a C$_3$ hydrocarbon chain wherein one chain atom is replaced with an oxygen atom.

These and other exemplary substituents are described in more detail in the Detailed Description, Examples, and Claims. The invention is not intended to be limited in any manner by the above exemplary listing of substituents.

The use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "derivative" of a compound refers to a compound derived from this compound by one or more chemical or physical transformations. In certain embodiments, a derivative of a compound is a salt, solvate, hydrate, polymorph, co-crystal, tautomer, stereoisomer, isotopically labeled derivatives or a prodrug of a compound. In certain embodiments, a derivative of a compound is compound from one or more steps of organic transformations. Exemplary organic transformations include, but are not limited to oxidation, reduction, halogenation, esterification, epoxidation, hydrolysis, deprotonation, etc.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent, such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "polymer" refers to a compound comprising eleven or more covalently connected repeating units. In certain embodiments, a polymer is naturally occurring. In certain embodiments, a polymer is synthetic (e.g., not naturally occurring). In certain embodiments, the $M_w$ of a polymer is between 1,000 and 2,000, between 2,000 and 10,000, between 10,000 and 30,000, between 30,000 and 100,000, between 100,000 and 300,000, between 300,000 and 1,000,000, g/mol, inclusive. In certain embodiments, the $M_w$ of a polymer is between 2,000 and 1,000,000, g/mol, inclusive.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non natural amino acids (i.e., compounds that do not occur in nature but that can be incorporated into a polypeptide chain) and/or amino acid analogs as are known in the art may alternatively be employed. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises between 2 and 10, between 10 and 30, between 30 and 100, between 100 and 300, or between 300 and 1,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad. Sci. U.S.A.* 85, 7448-7451, (1988)). A number of methods have been developed for delivering antisense DNA or RNA to cells, e.g., antisense molecules can be injected directly into the tissue site, or modified antisense molecules, designed to target the desired cells (antisense linked to peptides or antibodies that specifically bind receptors or antigens expressed on the target cell surface) can be administered systemically. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human, cells. Such promoters can be inducible or constitutive. Any type of plasmid, cosmid, yeast artificial chromosome, or viral vector can be used to prepare the recombinant DNA construct that can be introduced directly into the tissue site.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

A "polymer" is given its ordinary meaning as used in the art, i.e., a molecular structure comprising one or more repeat units (monomers), connected by covalent bonds. The repeat units may all be identical, or in some cases, there may be more than one type of repeat unit present within the polymer. In certain embodiments, the polymer has C=C. In certain embodiments, the polymer is prepared from ring opening metathesis polymerization.

The term "cross-linker" refers to compounds that link one polymer chain to another by covalent bonds or ionic bonds. "Polymer chains" can refer to synthetic polymers or natural polymers (such as proteins).

The term "macromonomer" refers to a macromolecule with one end-group that enables it to act as a monomer. Macromonomers will contribute a single monomeric unit to a chain of the completed macromolecule.

The term "prodrugs" refer to compounds and/or polymers, including compounds of Formula (I) and polymers of Formula (III') (e.g., Formula (III)), which have cleavable groups and become active by solvolysis, reduction, oxidation, or under physiological conditions, to provide the pharmaceutically active compounds in vivo. Prodrugs include polymeric derivatives conjugated with the pharmaceutical active compounds known to practitioners of the art, such as, for example, to form an ester by reaction of the acid, or acid anhydride, or mixed anhydrides moieties of the polymer of the polymer with the hydroxyl moiety of the pharmaceutical active compound, or to form an amide prepared by the acid, or acid anhydride, or mixed anhydrides moieties of the polymer with a substituted or unsubstituted amine of the pharmaceutically active compound. Simple aliphatic or aromatic esters, amides, and anhydrides derived from acidic groups pendant on the polymers of this invention are particular prodrugs. In some embodiments, the polymer incorporates one therapeutic agent. In some embodiments, the polymer incorporates more than one therapeutic agents.

A linker being "cleavable" refers to at least one bond in the linker being able to break. In certain embodiments, at least 10%, at least 30%, at least 50%, at least 90%, at least 95%, or at least 99% (e.g., at least 90%) of the at least one bond is able to break within 1 minute, 10 minutes, 1 hour, 3 hours, 8 hours, or 24 hours, under a condition (e.g., irradiation (e.g., irradiation with UV), presence of a reductant, physiological condition, or a combination thereof). In certain embodiments, the at least one bond is in the linker's backbone.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic or genetically engineered animal.

The terms "administer," "administering," or "administration" refer to implanting, absorbing, ingesting, injecting, inhaling, or otherwise introducing an inventive polymer, or a pharmaceutical composition thereof, or a device incorporating the inventive polymer.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" is an amount sufficient to provide a therapeutic benefit in the treatment of a condition or to delay or minimize one or more symptoms associated with the condition. A therapeutically effective amount of an inventive polymer means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis or diseases associated with angiogenesis, inflammatory diseases, autoinflammatory diseases, and autoimmune diseases.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An example of a pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT)

lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenstrim's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemiallymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and growth of new blood vessels. Normal angiogenesis occurs in the body of a healthy subject during wound healing and for restoring blood flow to tissues after injury. The body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal angiogenesis refers to angiogenesis greater than that in a normal body, especially angiogenesis in an adult not related to normal angiogenesis (e.g., menstruation or wound healing). Abnormal angiogenesis can result in new blood vessels that feed diseased tissues and/or destroy normal tissues, and in the case of cancer, the new vessels can allow tumor cells to escape into the circulation and lodge in other organs (tumor metastases).

The term "ratiometric" refers to the situation where $C_1^i$ is substantially equal to $C_0^i$, wherein $C_0^i$ refers to the ratio of the amount of a first agent before the first agent is delivered to a subject, tissue, or cell, to the total amount of two or more agents (including the first agent) before the two or more agents are delivered to the subject, tissue, or cell; and $C_1^i$ refers to the ratio of the amount of the first agent that is delivered to the subject, tissue, or cell, to the total amount of the two or more agents (including the first agent) that are delivered to the subject, tissue, or cell. In certain embodiments, the delivery of each one of the two or more agents is ratiometric.

The term "orthogonal" refers to the situation where a first agent and a second agent, each of which is included in a Pt-BASP described herein, is independently released from the Pt-BASP. In certain embodiments, under condition A, the first agent, but not the second agent, is released from the Pt-BASP. For example, an orthogonal release or orthogonal delivery of the first and second agents includes: under condition A, the first agent, but not the second agent, is released from the Pt-BASP; under condition B, the second agent, but not the first agent, is released from the Pt-BASP. The release or delivery of the first and second agents is not orthogonal when, for example, under condition C, both the first and second agents are released from the Pt-BASP.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The highlighted functional groups of CPT and DOX indicate where the drug is conjugated to the MM.

Figure 10:
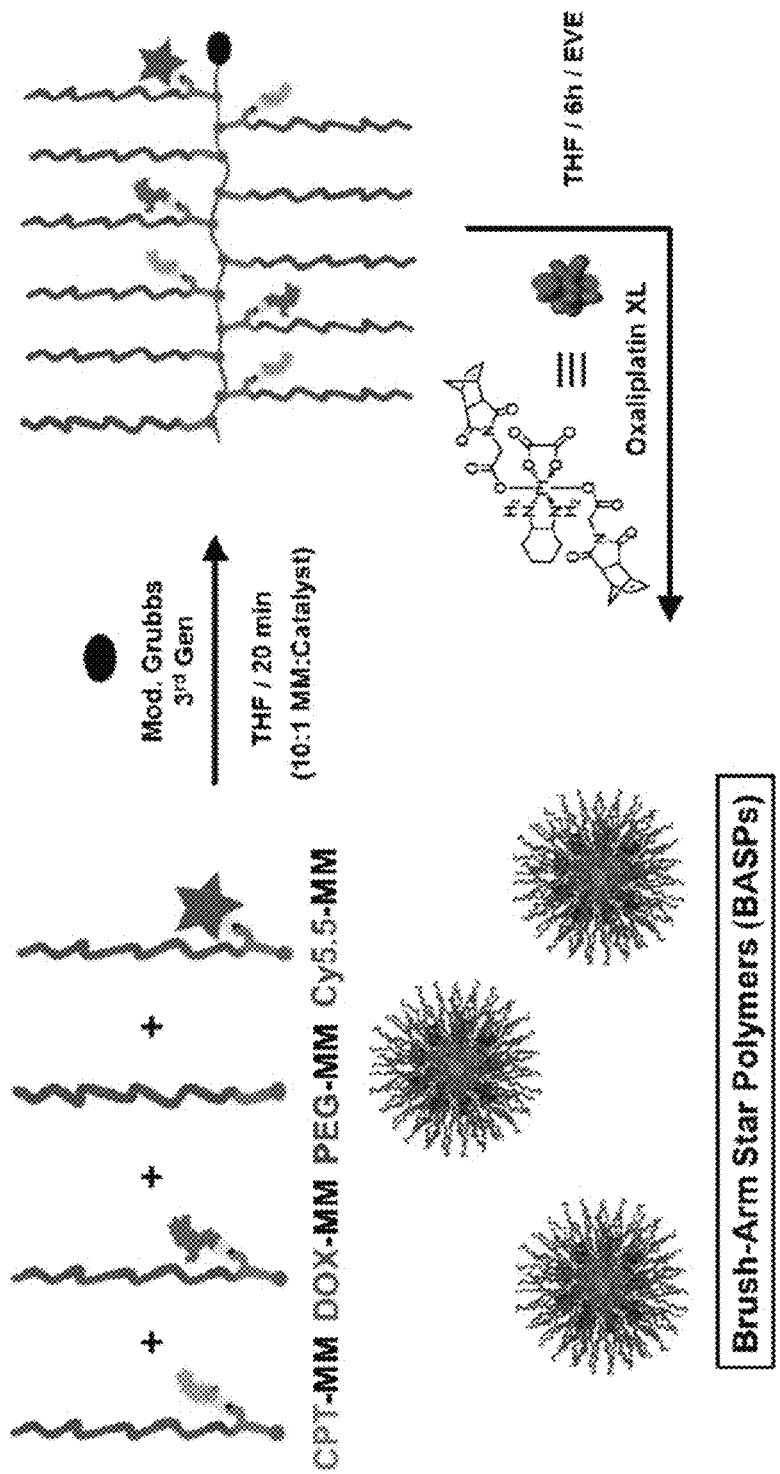

FIG. 10 shows the general scheme for the synthesis of the reported drug-loaded brush polymers, followed by cross-linking with the bis-norbornene functionalized Pt(IV) prodrug to afford brush-arm star polymers (BASPs) used for in vitro and in vivo efficacy studies.

Figure 11:
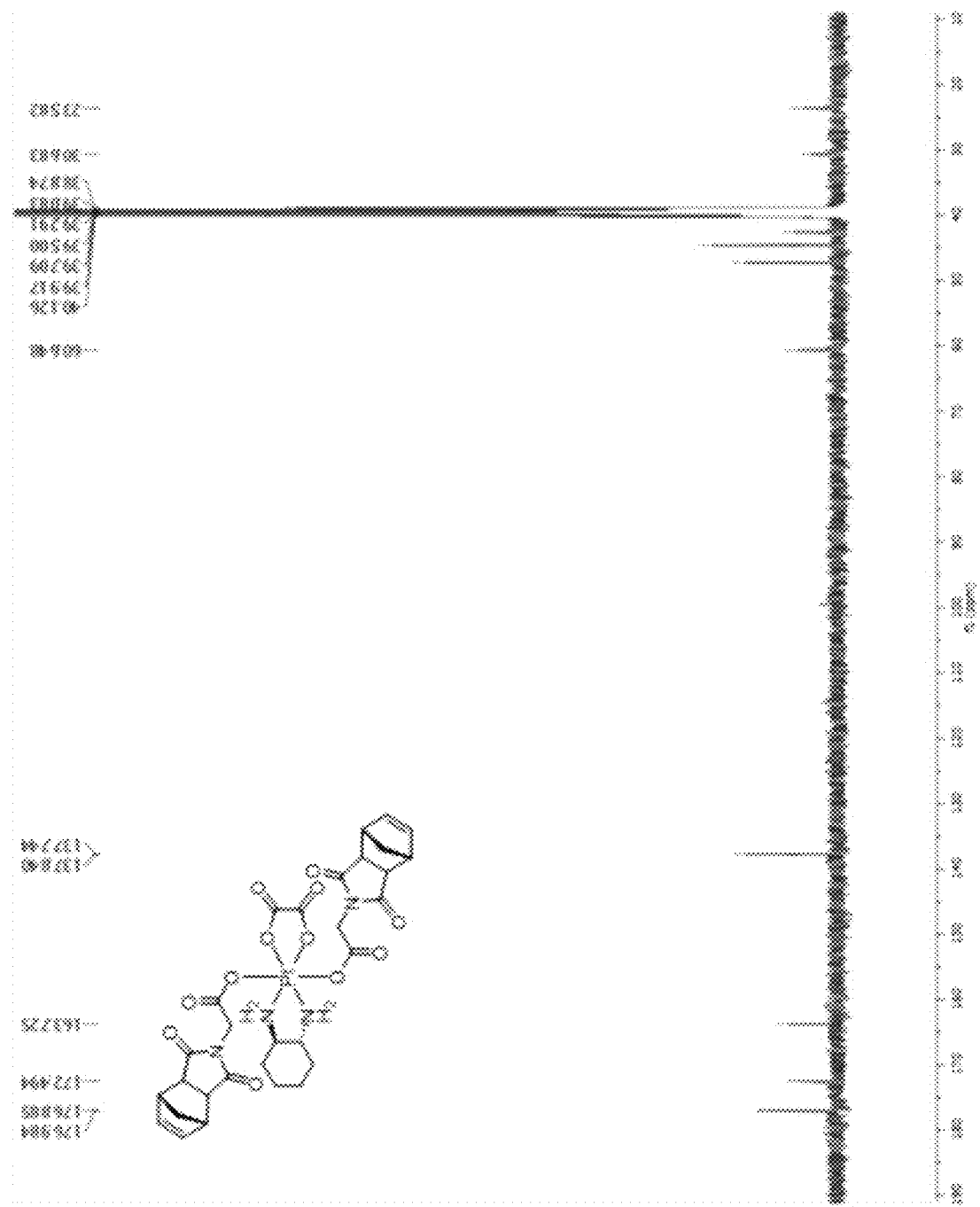

FIG. 11 shows the $^{13}$C nuclear magnetic resonance (NMR) of OxPtXL (100 MHz, DMSO-$d_6$, 298K).

Figure 12:
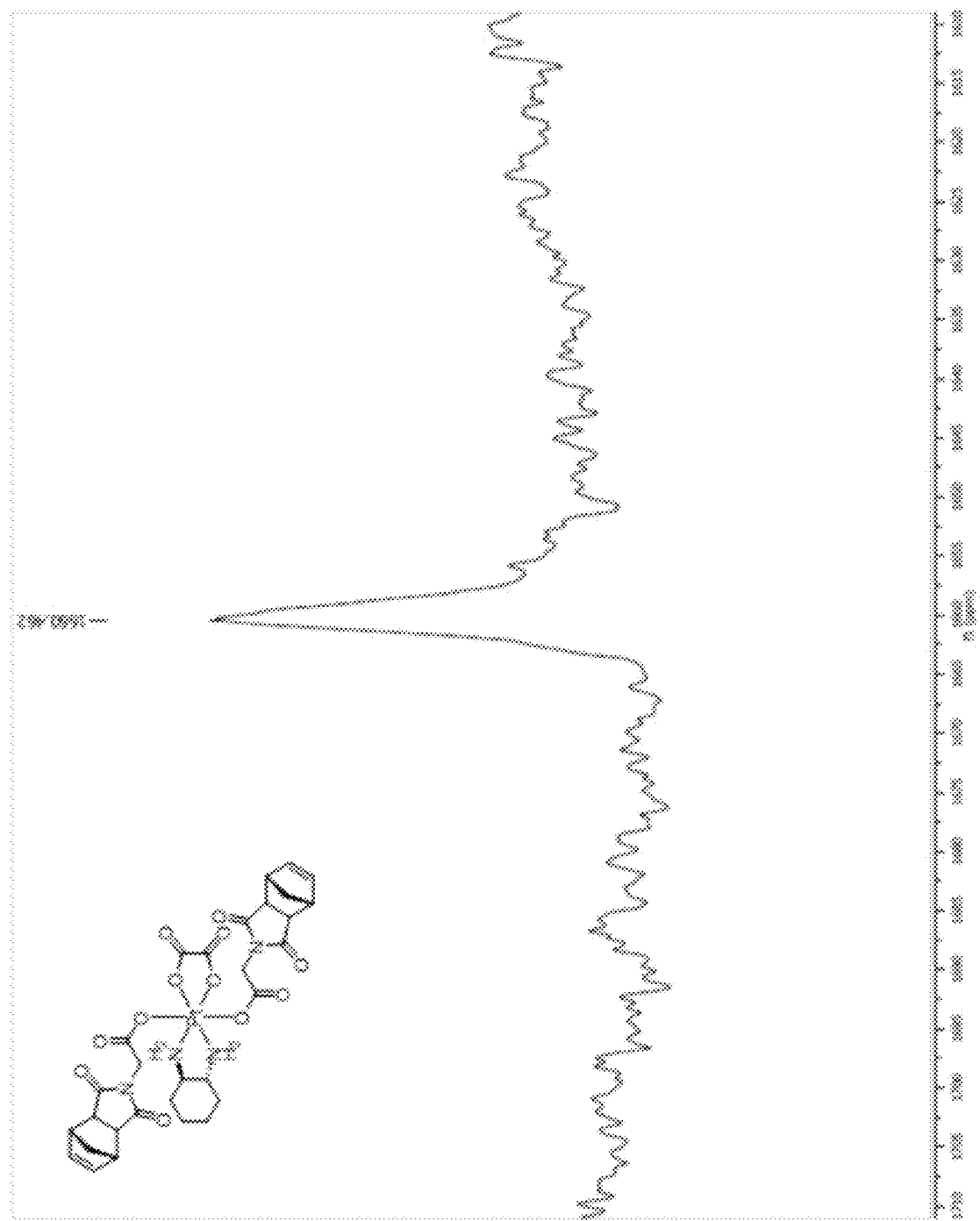

FIG. 12 shows the $^{195}$Pt NMR of OxPtXL (86 MHz, DMSO-$d_6$, 298K).

Figure 13A:
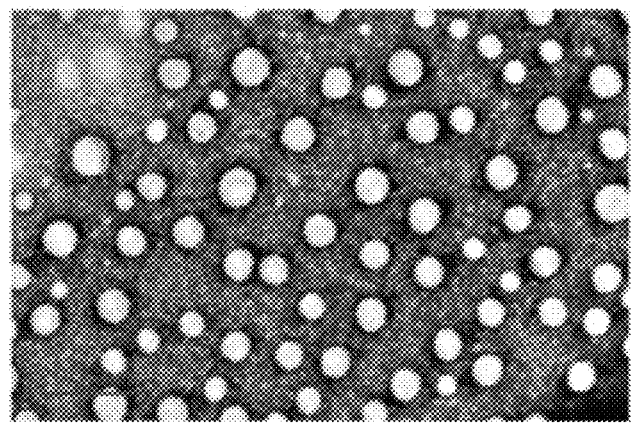
Figure 13B:
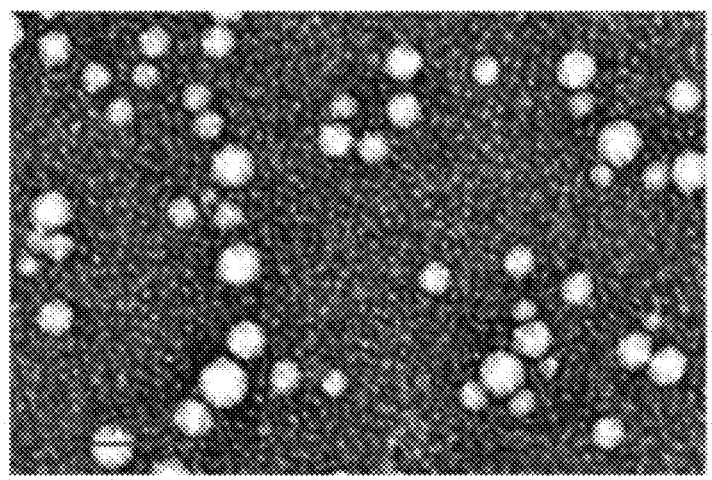
Figure 13C:
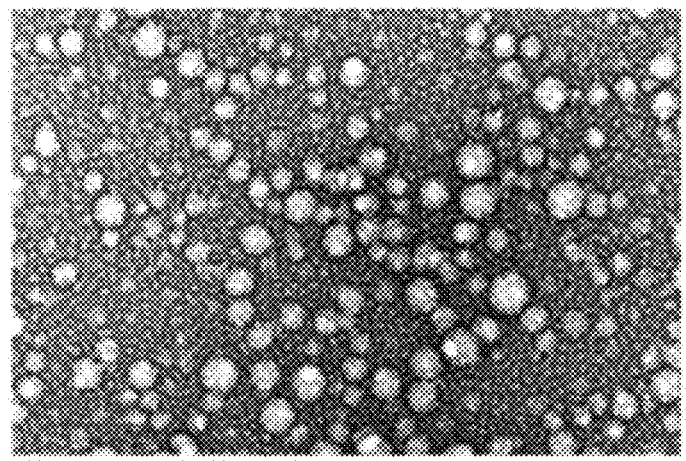
Figure 13D:
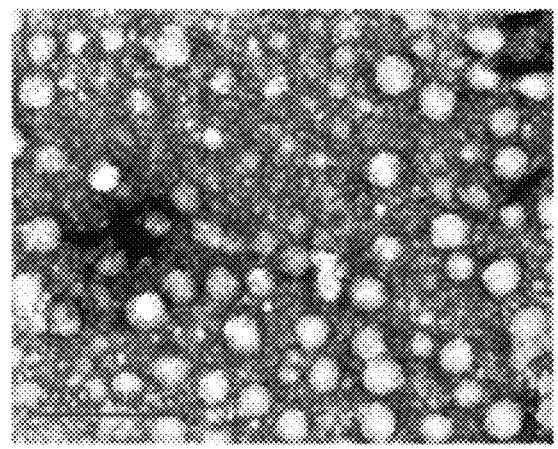

FIGS. 13A to 13D show TEM images of: i) CPT-oxPt-dilute DOX (0.2%) 3-drug BASP (FIG. 13A); ii) CPT-AcetalXL 1-drug BASP (FIG. 13B); iii) DOX-AcetalXL 1-drug BASP (FIG. 13C); and iv) PEG-AcetalXL no-drug BASP (FIG. 13D).

Figure 14A:
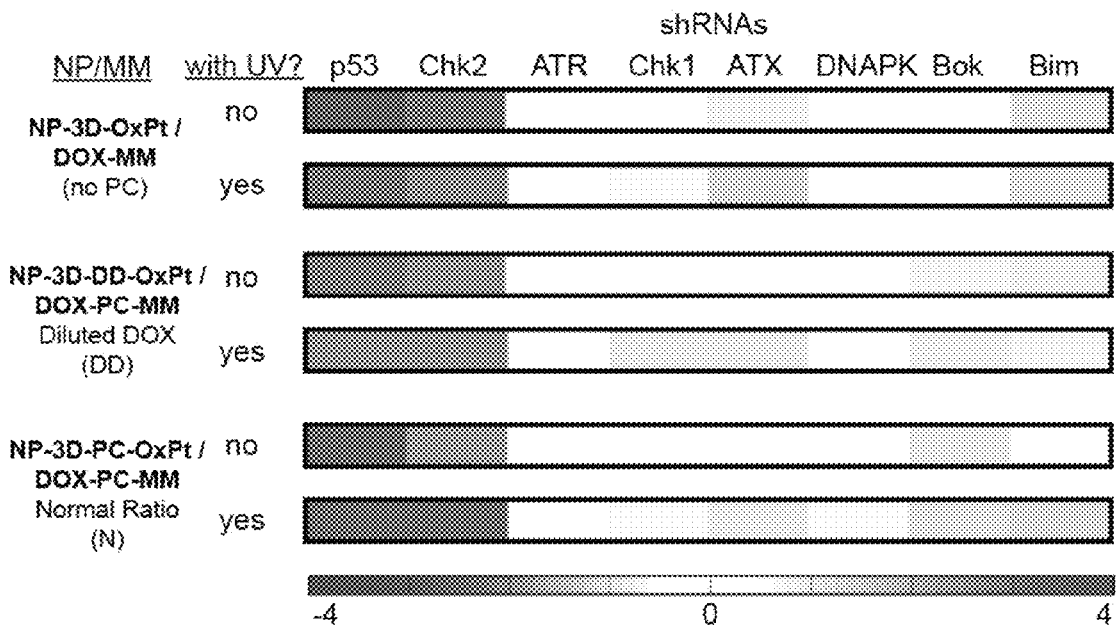
Figure 14B:
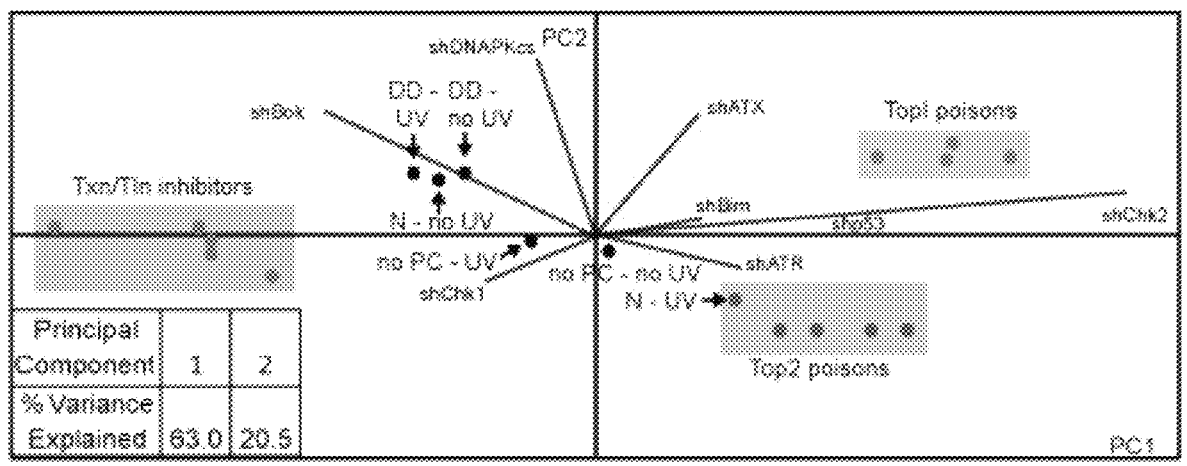

FIGS. 14A to 14B show a signature assay heat map (FIG. 14A) which illustrates the effect that UV-triggered release of DOX has on the mechanism of action of the three-drug-loaded nanoparticle and corresponding principal component analysis (FIG. 14B).

Figure 15:
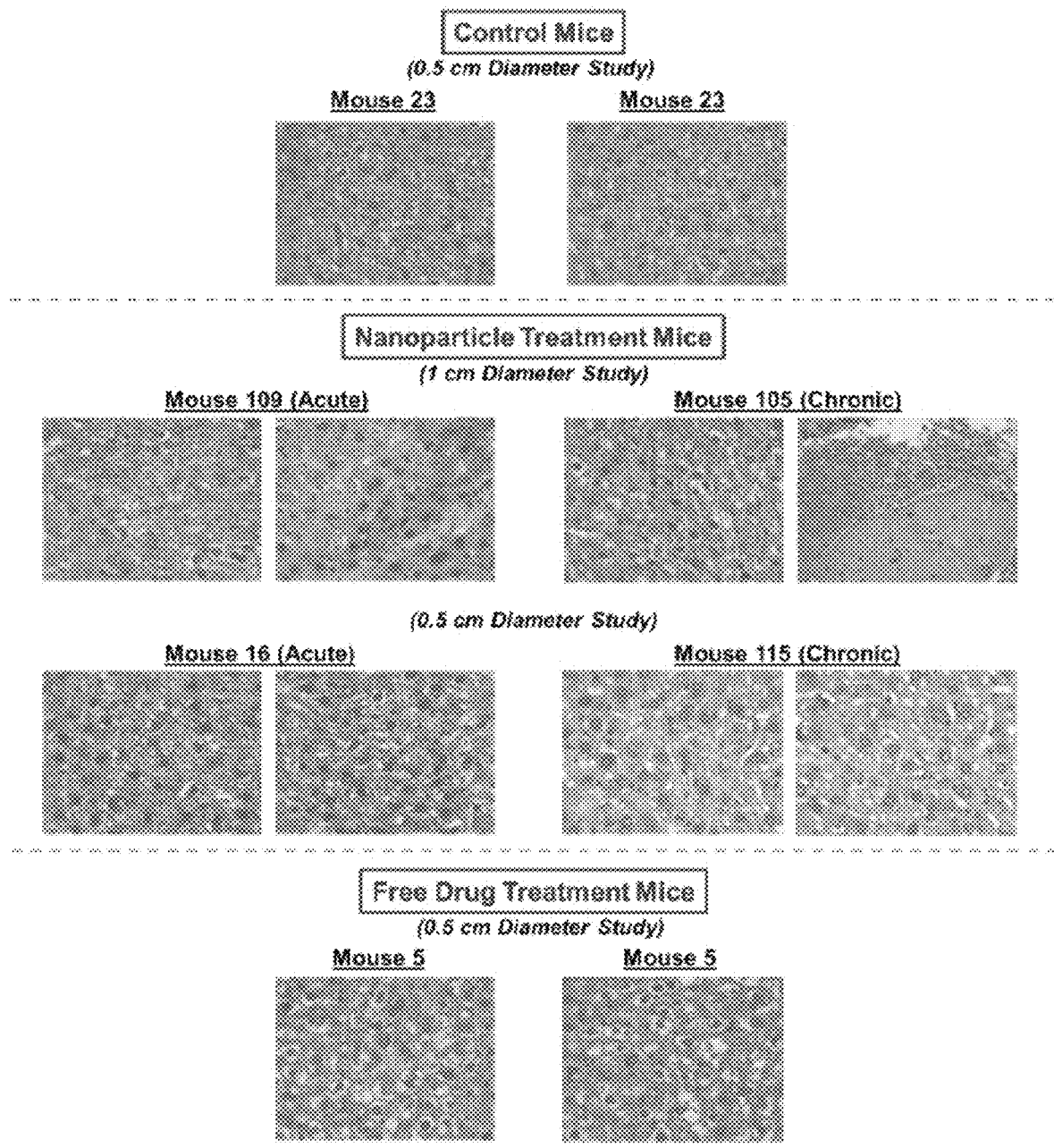

FIG. 15 shows different views of paraffin-embedded and H&E stained liver cross sections obtained from control mice (top panel), nanoparticle-treated mice with tumors possessing 1 cm and 0.5 cm diameters (middle panel), and free drug treated mice (bottom panel).

Figure 16:
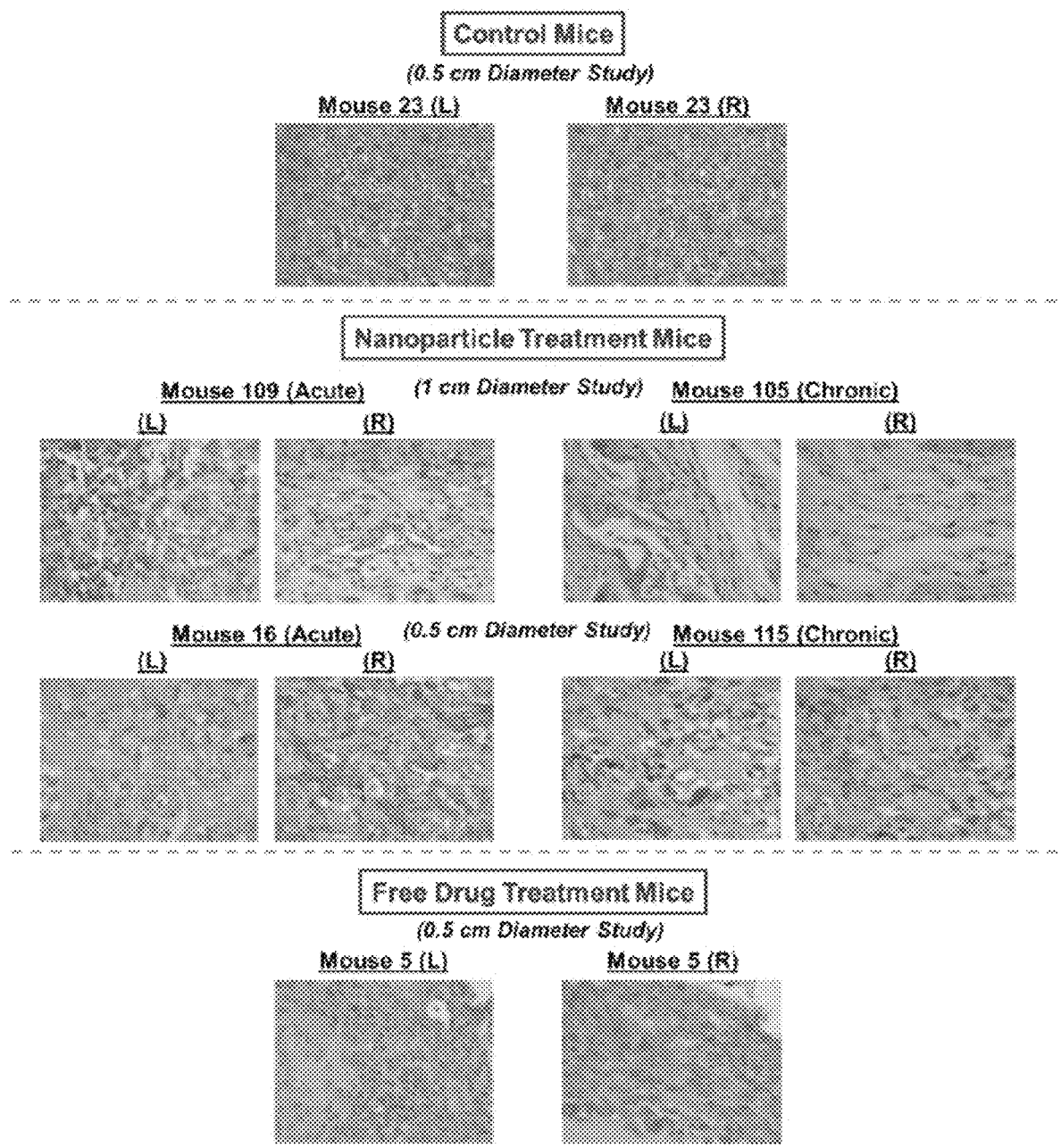

FIG. 16 shows different views of paraffin-embedded and H&E stained left (L) and right (R) tumor cross sections obtained from control mice (top panel), nanoparticle-treated mice with tumors possessing 1 cm and 0.5 cm diameters (middle panel), and free drug treated mice (bottom panel).

Figure 17A:
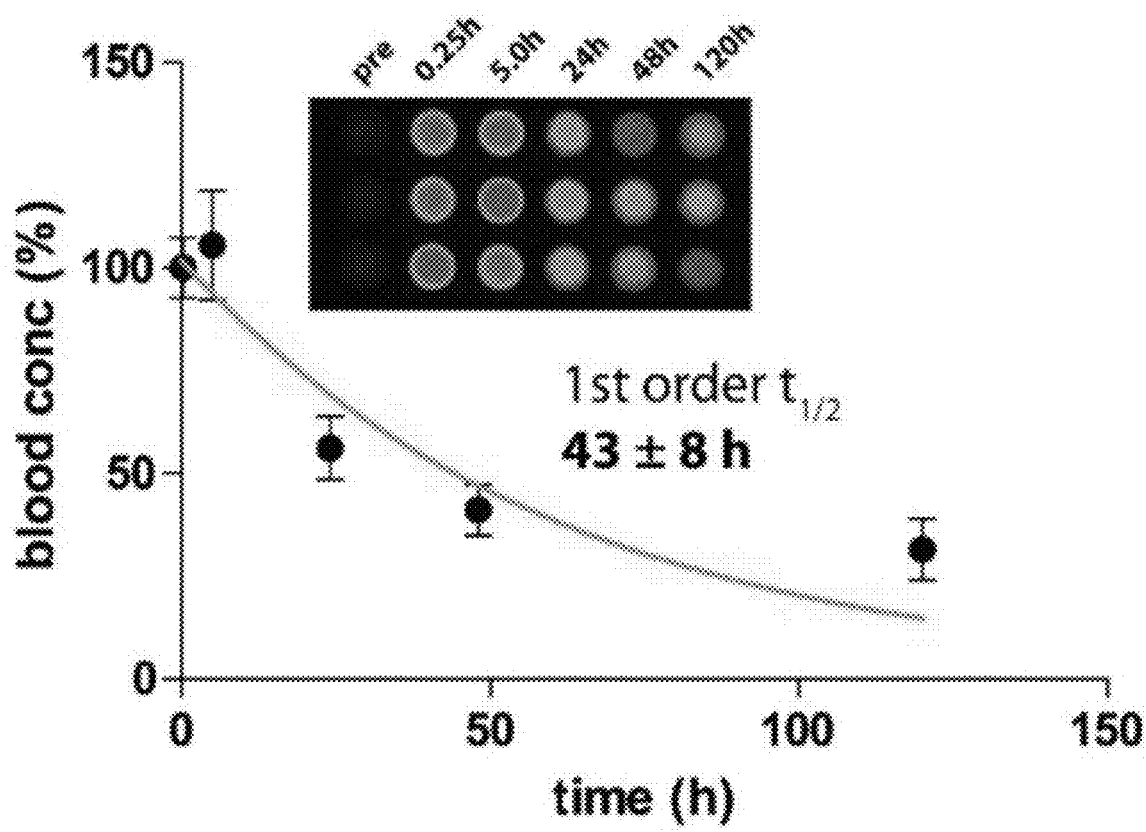
Figure 17B:
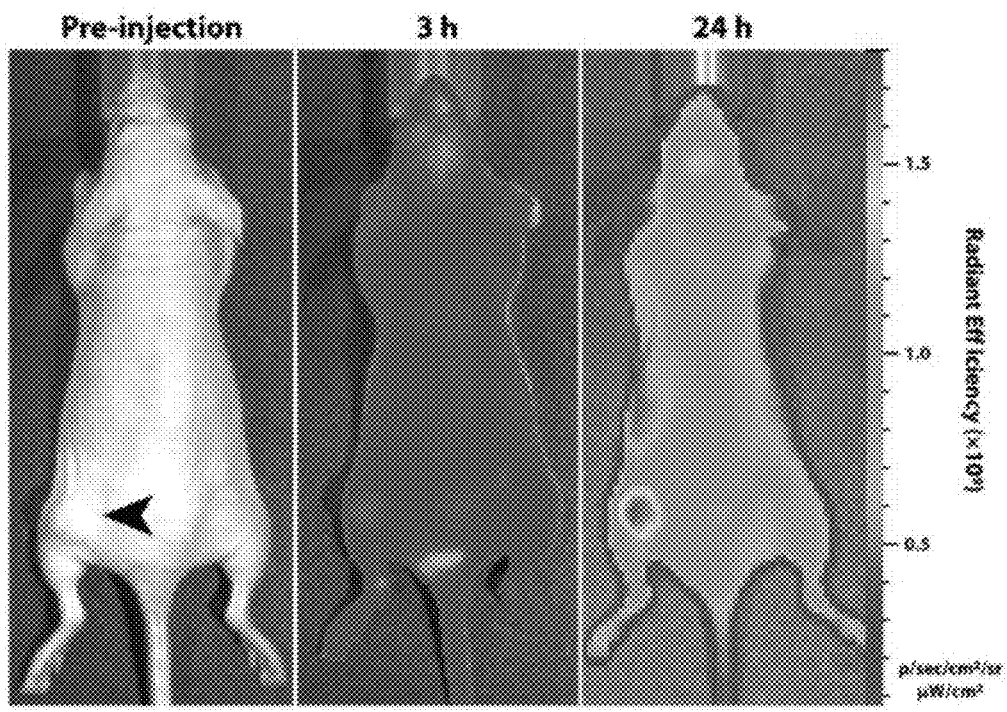

FIGS. 17A to 17B show the pharmacokinetics of NP-OxPt containing 1% Cy5.5-MM injected (4.5 mg/dose; 18 mg/kg) in BALB/c mice over a 126 h period (FIG. 17A) and tumor localization in NCR-NU mice injected with NP-OxPt containing 1% Cy5.5-MM (FIG. 17B).

Figure 18:
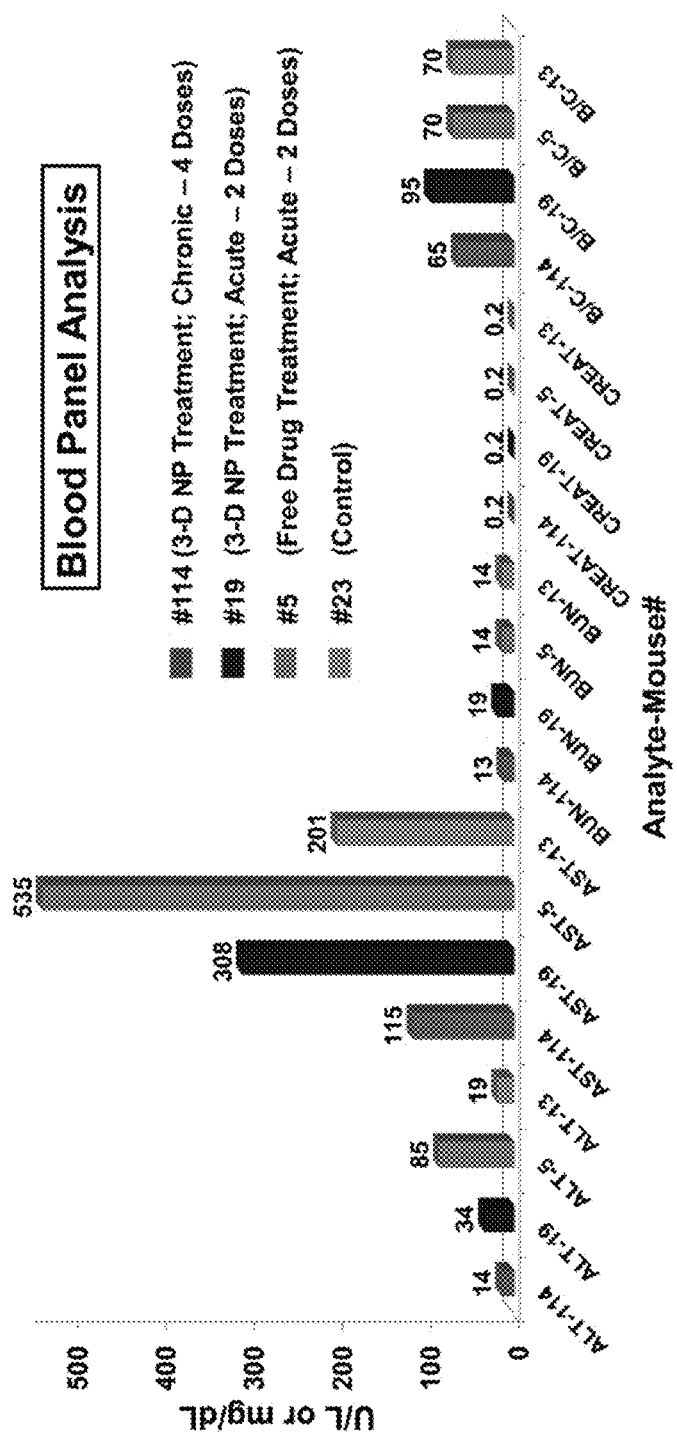

FIG. 18 shows the blood panel analysis of biomarkers associated with NCR-NU mice treated with NP-3D-OxPt (#114 bars: Chronic; #19 bars: Acute), the free drug combination (#5 bars: DOX-CPT-OxPt), or 5% glucose solutions. B/C=BUN/Creatinine.

Figure 19A:
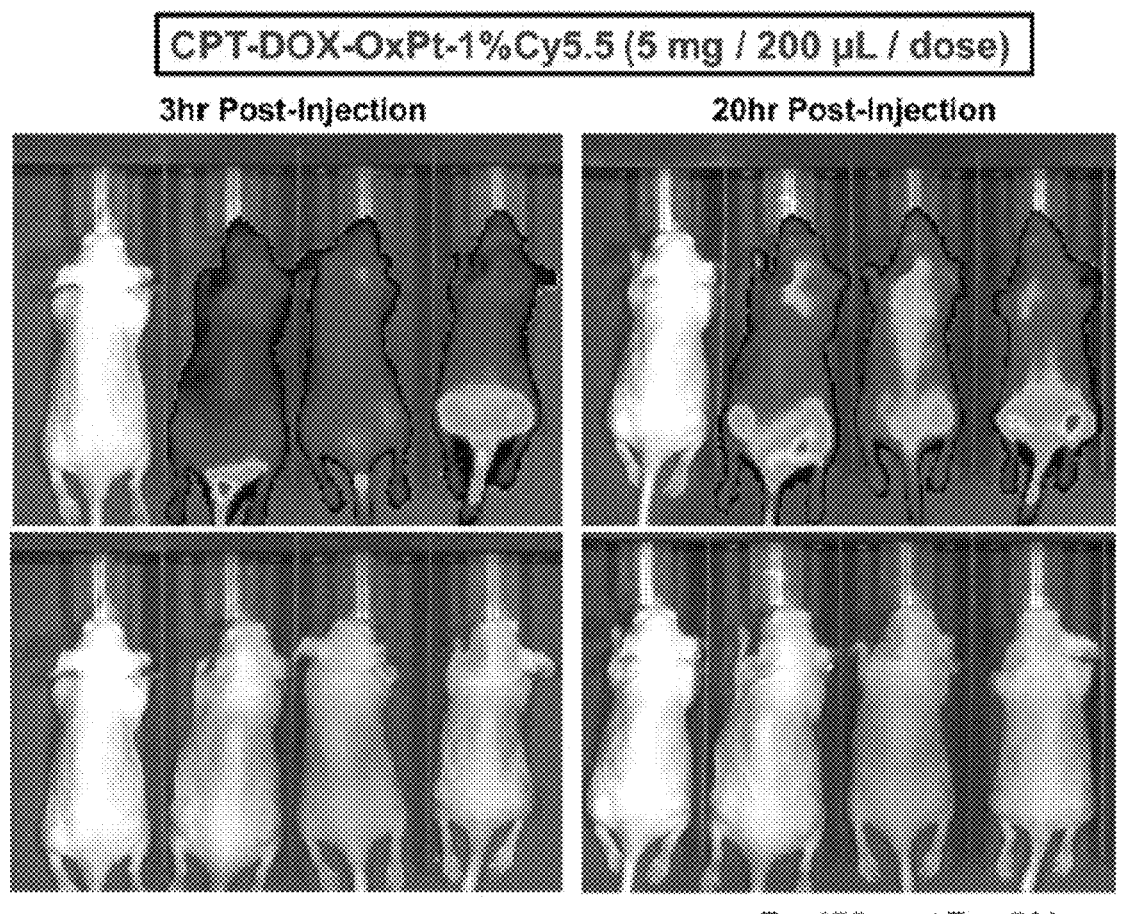
Figure 19B:
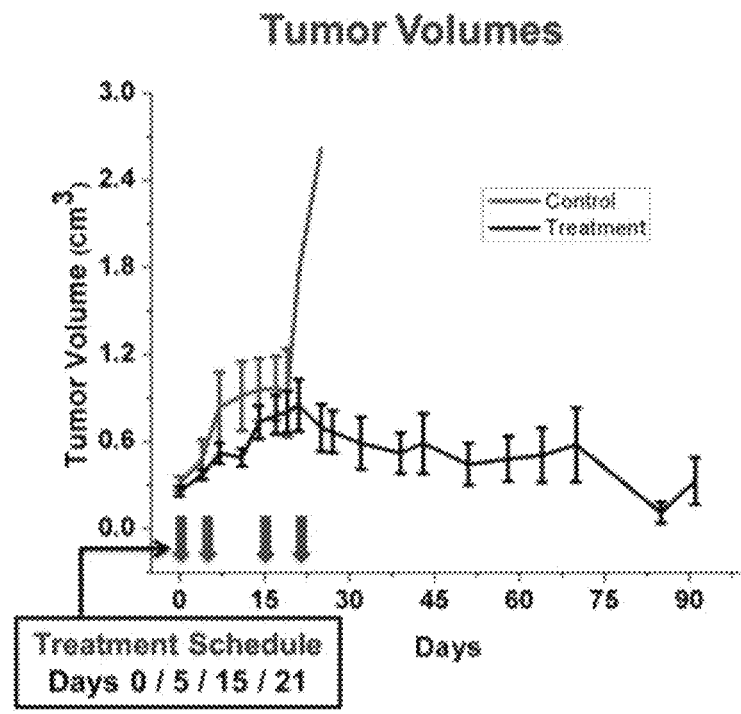
Figure 19C:
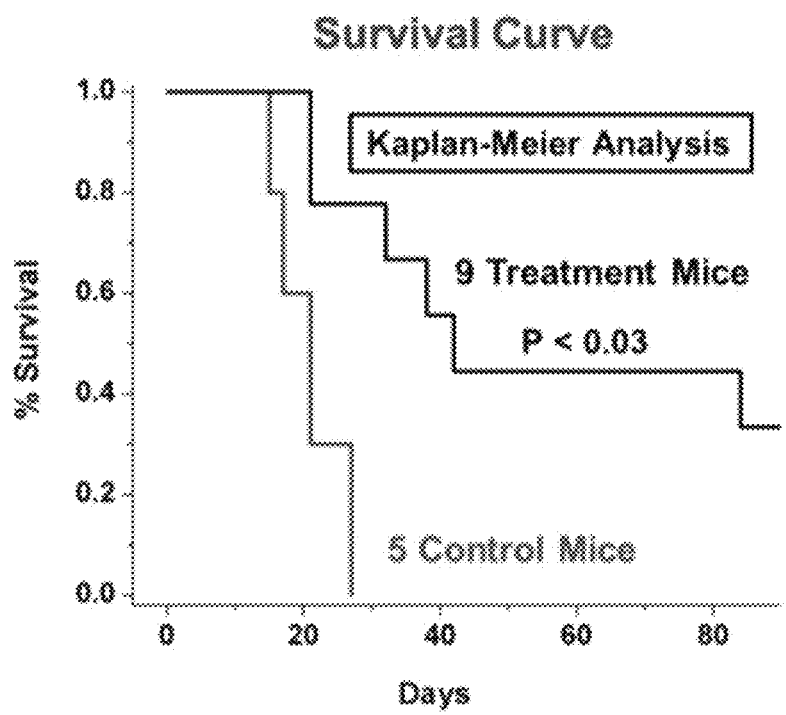

FIGS. 19A to 19C show: i) tumor localization of NP-3D-OxPt-Cy5.5 in NCR-NU mice injected with 5 mg of the three-drug-loaded nanoparticle and monitoring (excitation at 675 nm; emission at 720 nm) the epifluorescence at 3 and 20 h in an IVIS whole animal imaging system (FIG. 19A); ii) a tumor volume plot and treatment schedule for the in vivo efficacy evaluation of mice possessing 1 cm in diameter subcutaneous xenograft tumors (FIG. 19B); and iii) a survival curve illustrating the survival probability of the nanoparticle treated mice versus the control mice that were only injected with 5% glucose solutions (FIG. 19C).

Figure 20A:
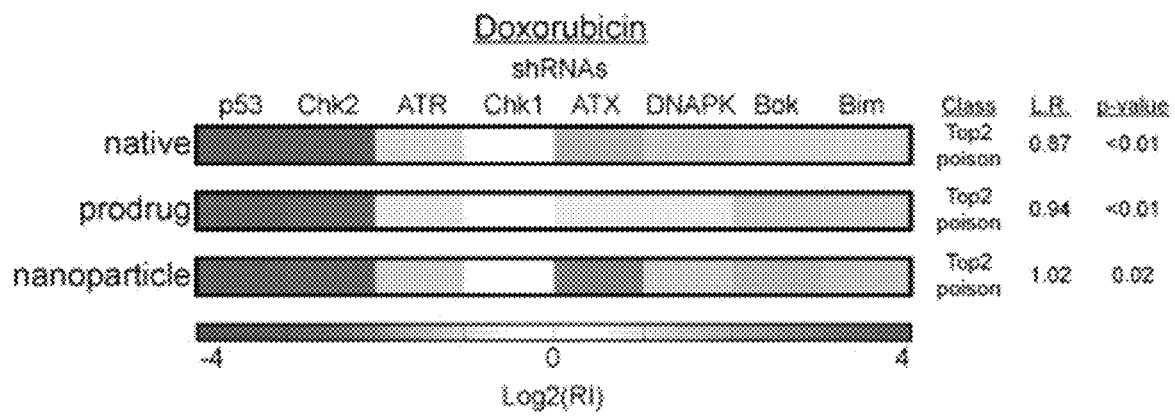
Figure 20B:
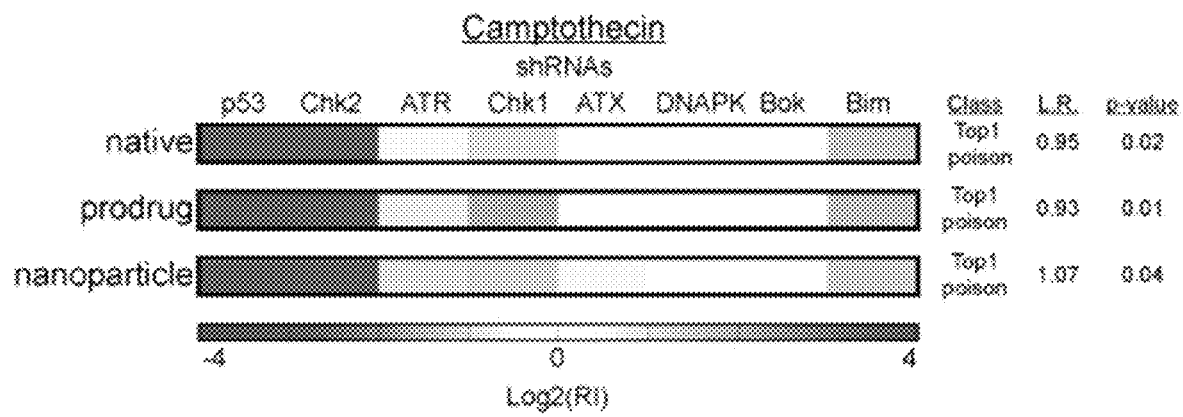
Figure 20C:
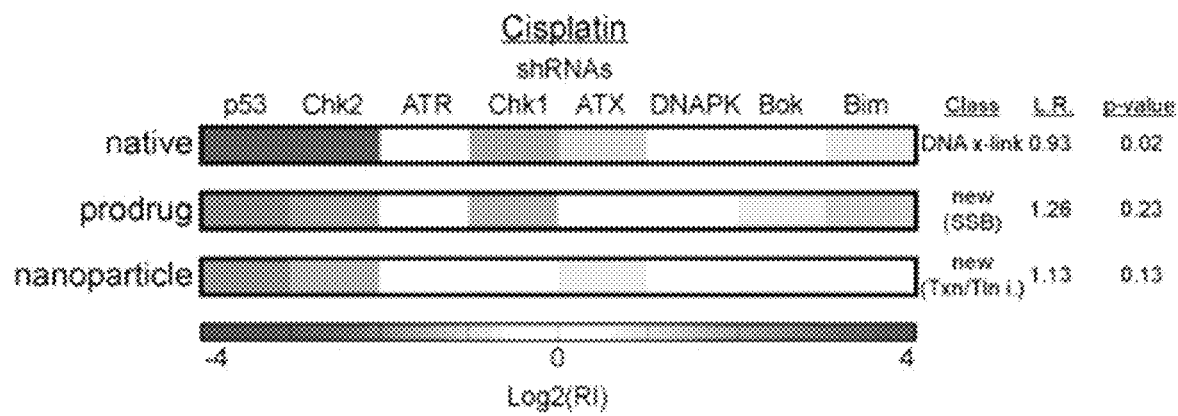
Figure 20D:
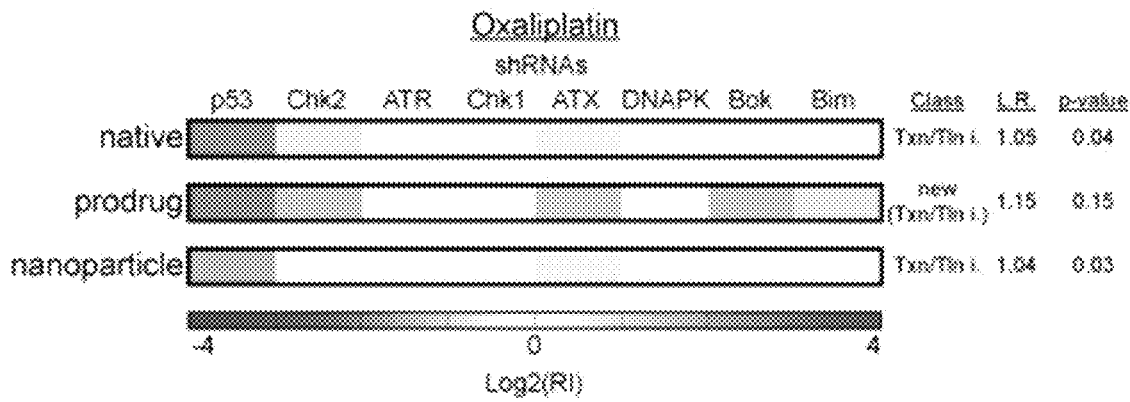
Figure 20E:
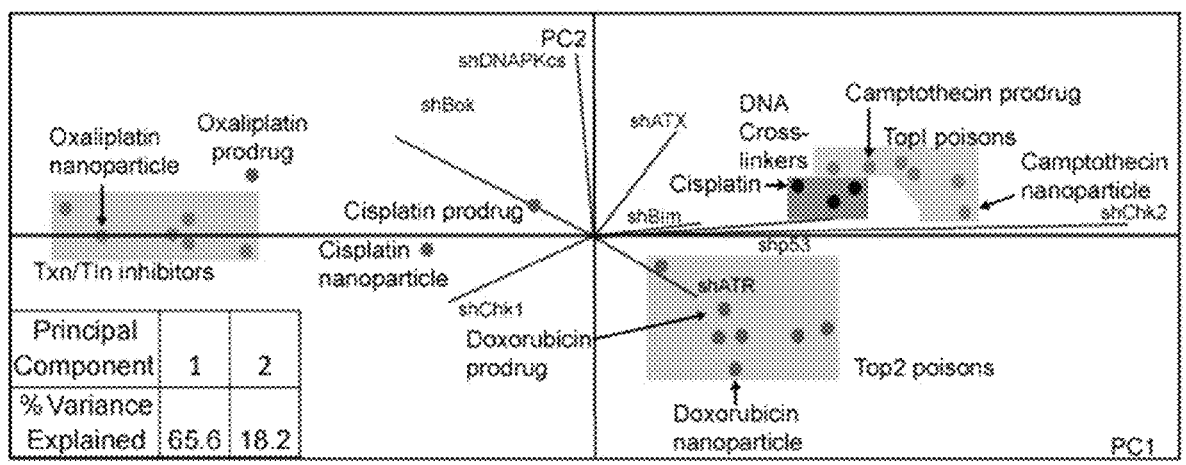
Figure 20F:
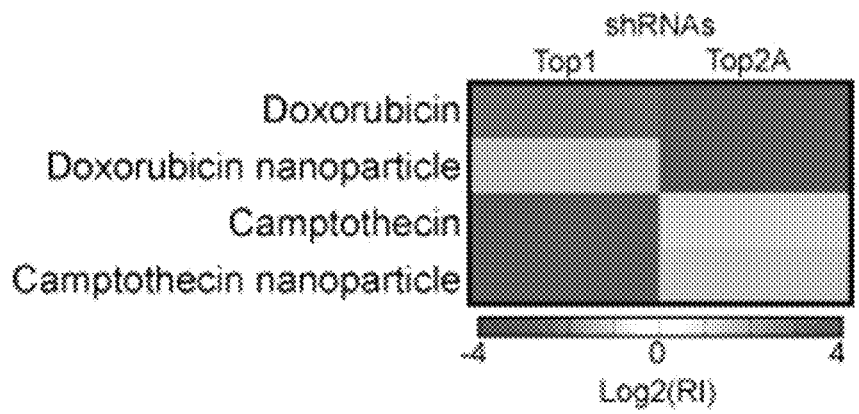

FIGS. 20A to 20F show heat maps and classification of: i) doxorubicin native, prodrug and nanoparticles (FIG. 20A); ii) camptothecin native, prodrug and nanoparticles (FIG. 20B); iii) cisplatin native, prodrug and nanoparticles (FIG. 20C); iv) oxaliplatin native, prodrug and nanoparticles (FIG. 20D); v) corresponding principal component analysis of the RNAi signatures from native, prodrug and nanoparticles of doxorubicin, camptothecin, cisplatin and oxaliplatin as well as representative drugs from transcription/translation (Txn/Tln) inhibitor, Top2 poison, Top1 poison, and DNA cross-linker reference set categories (FIG. 20E); and vi) a heat map depicting response of Top1 and Top2A shRNA bearing cells to treatment with doxorubicin or camptothecin free drug or nanoparticles (FIG. 20F).

Figure 21A:
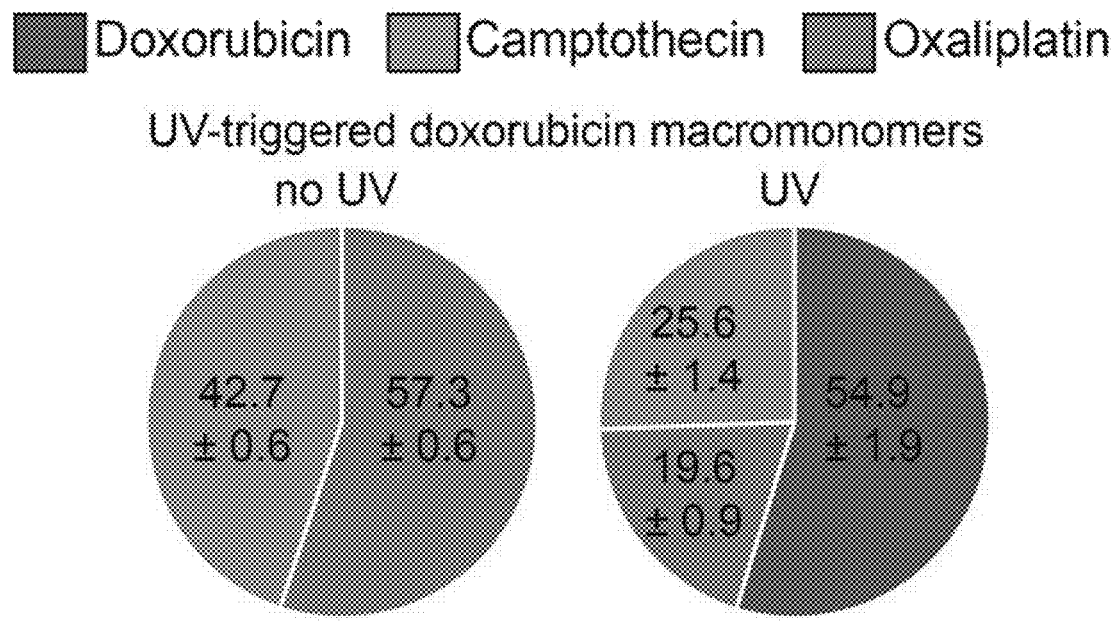
Figure 21B:
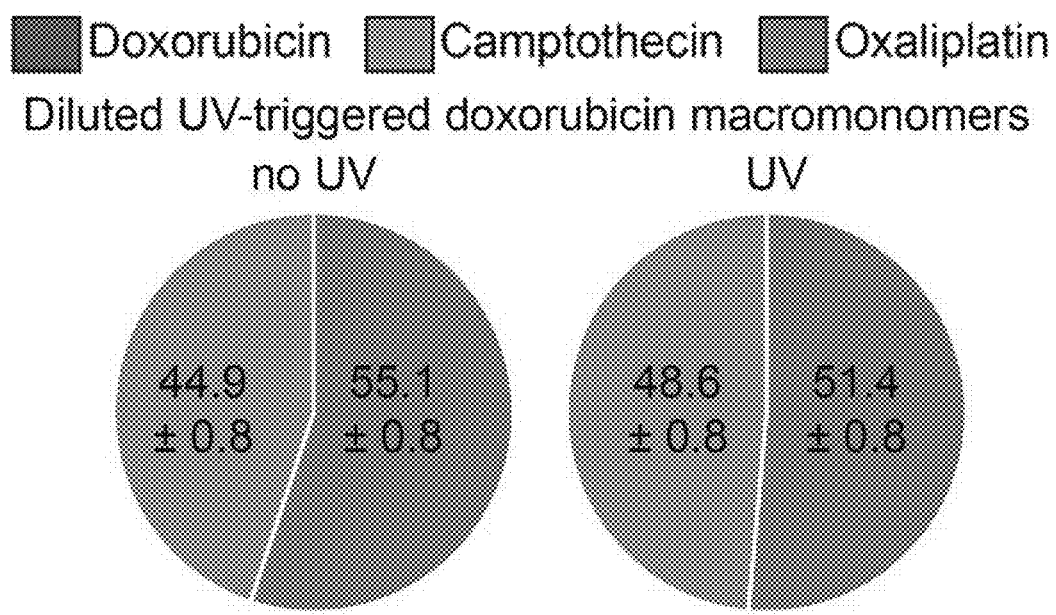
Figure 21C:
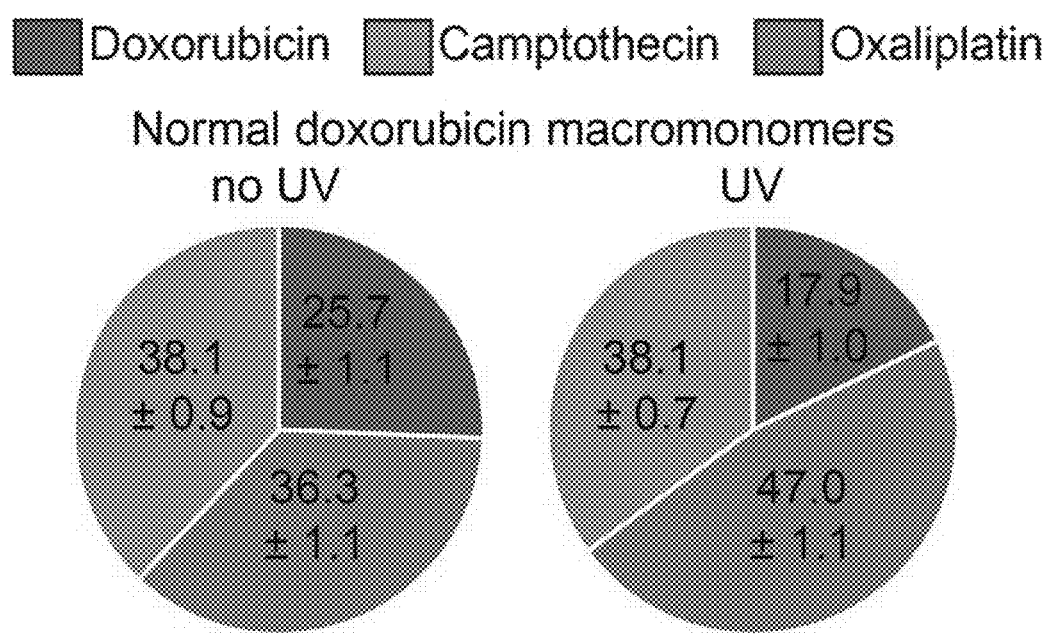

FIGS. 21A to 21C show the constrained linear regression prediction of the impact of the following combination nanoparticles on the mechanism of action: i) UV-triggered doxorubicin macromonomers with or without UV (FIG. 21A); ii) very diluted UV-triggered doxorubicin macromonomers with or without UV (FIG. 21B); and iii) normal doxorubicin macromonomers with or without UV (FIG. 21C).

Figure 22:
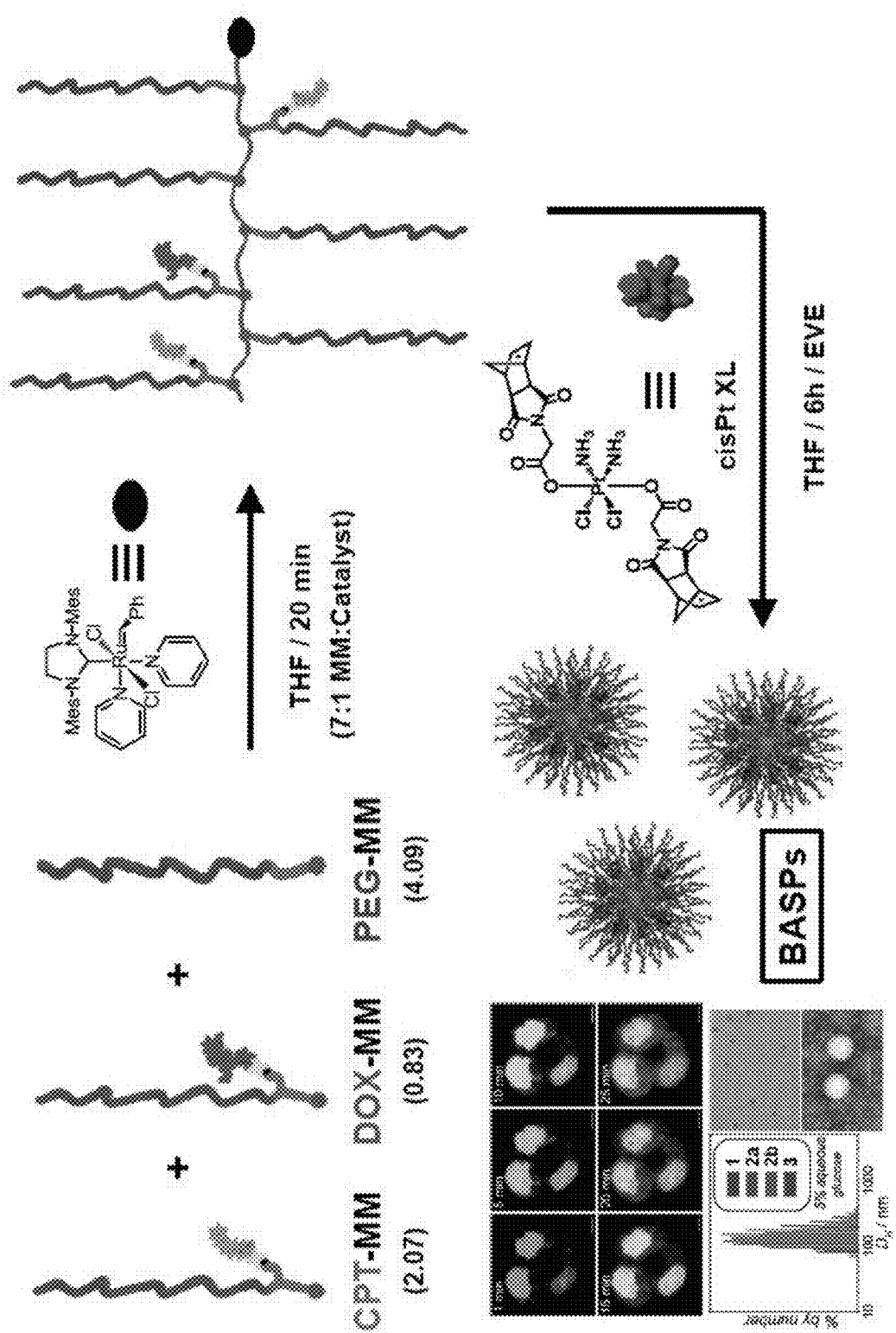

FIG. 22 shows the synthesis of cisplatin (cisPt)-Doxorubicin(DOX)-camptothecin (CPT) nanoparticles prepared by cross-linking with the bis-norbornene functionalized Pt(IV) prodrug to afford brush-arm star polymers (BASPs) used for in vitro and in vivo efficacy studies. The DLS histograms for drug-loaded BASPs are as follows: cisplatin only (1), cisplatin and CPT (2a), cisplatin and DOX (2b), and cisplatin and CPT and DOX (3). The TEM images are of positively (top panel) and negatively (bottom panel) stained cisPt-DOX-CPT nanoparticles.

Figure 23A:
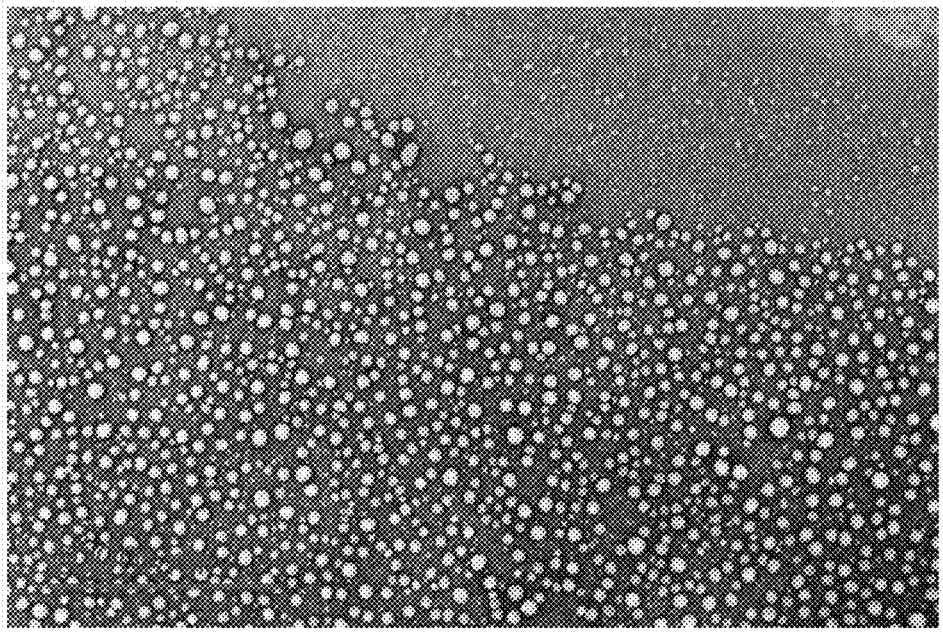
Figure 23B:
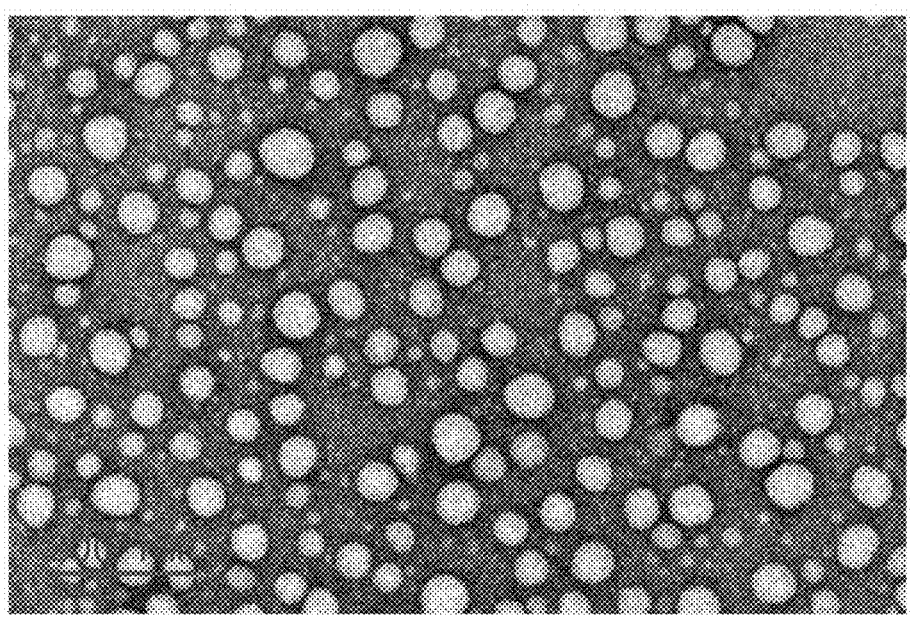
Figure 23C:
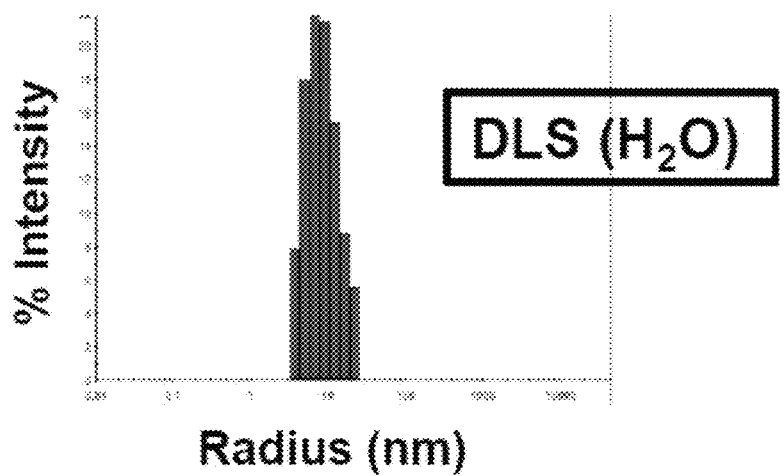
Figure 23D:
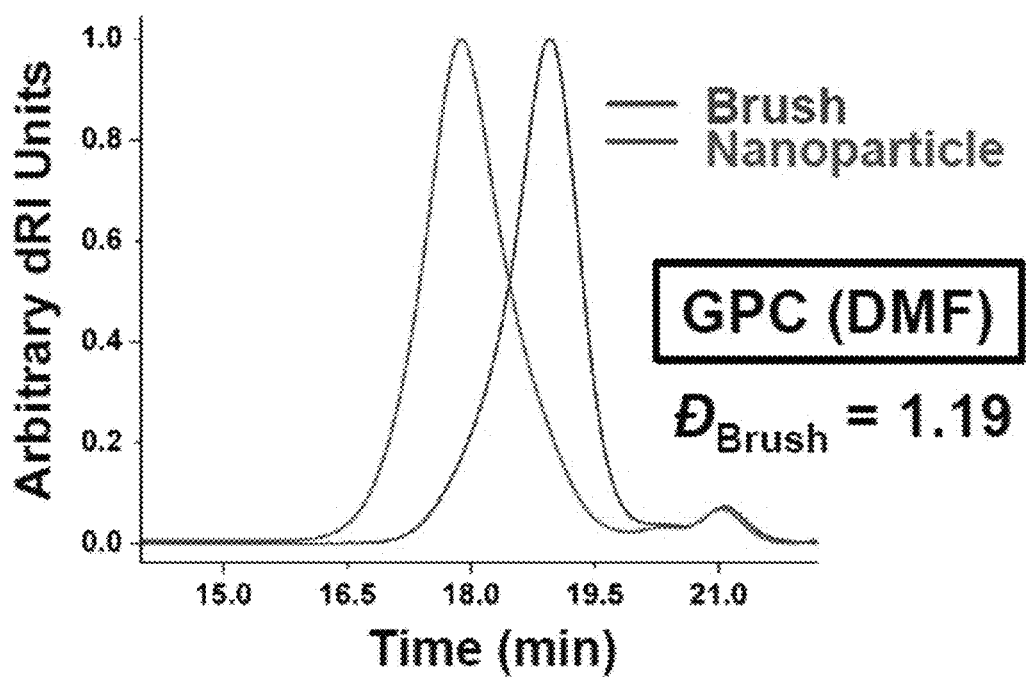

FIGS. 23A to 23D show characterization data for NP-3D-OxPt-Cy5.5 BASPs through TEM images (FIGS. 23A to 23B), and OxPt-CPT-DOX BASPs through digital light scattering (DLS) analysis (FIG. 23C) and gel permeation chromatography (GPC) analysis (FIG. 23D).

Figure 24A:
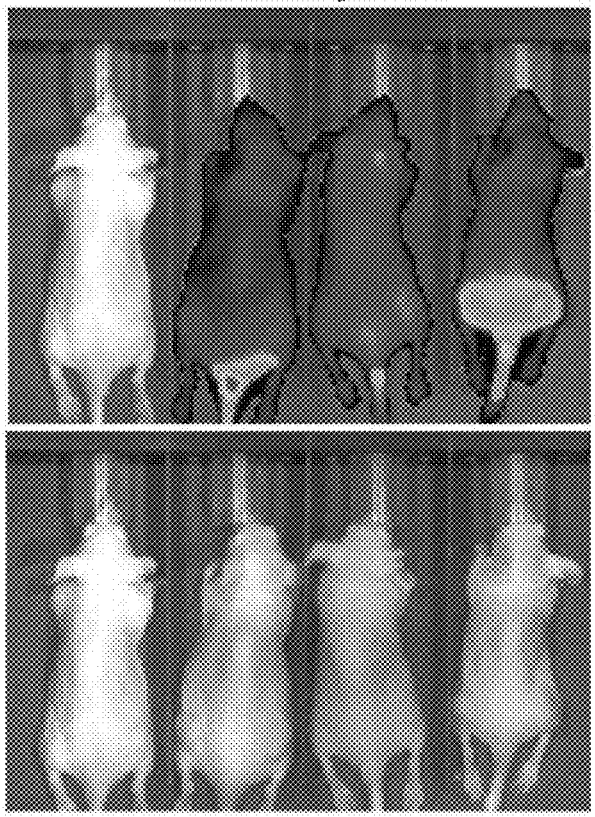
Figure 24A:
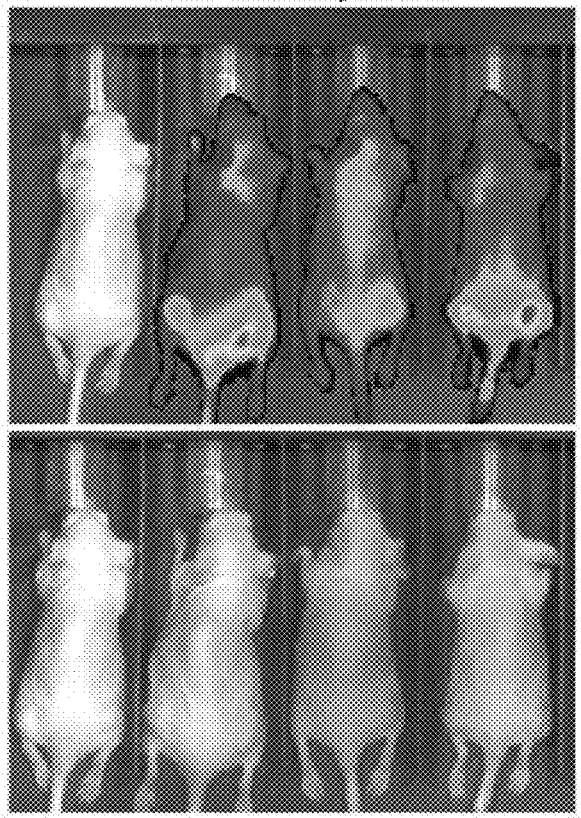
Figure 24B:
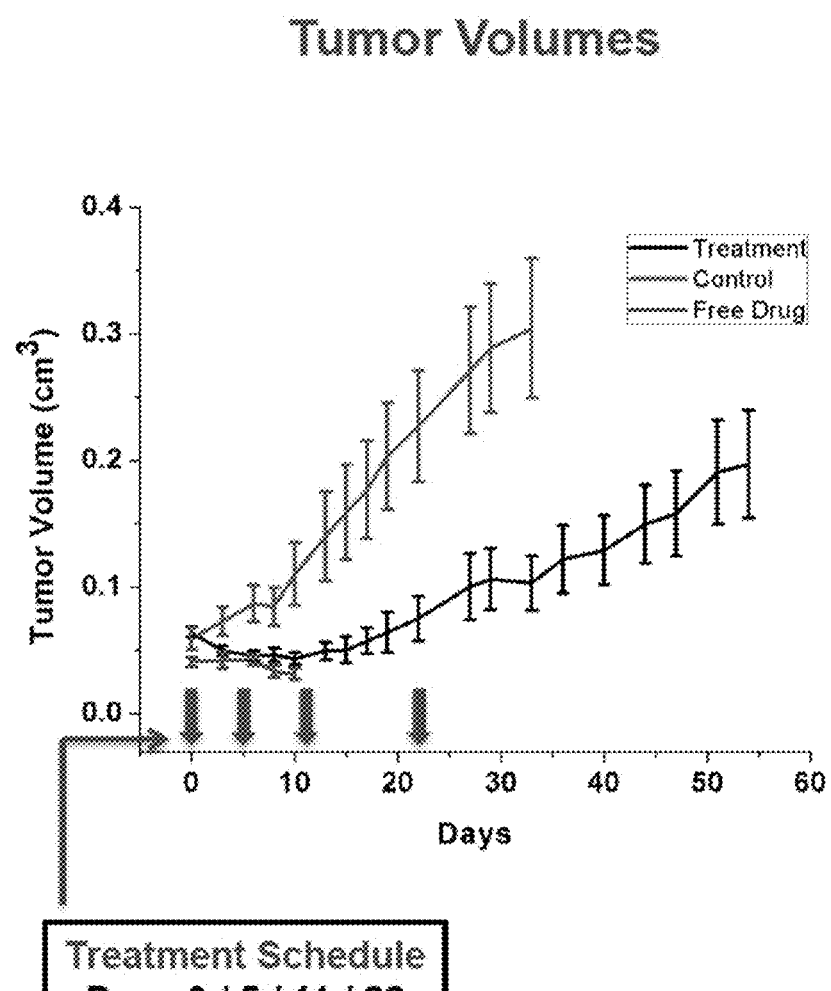
Figure 24C:
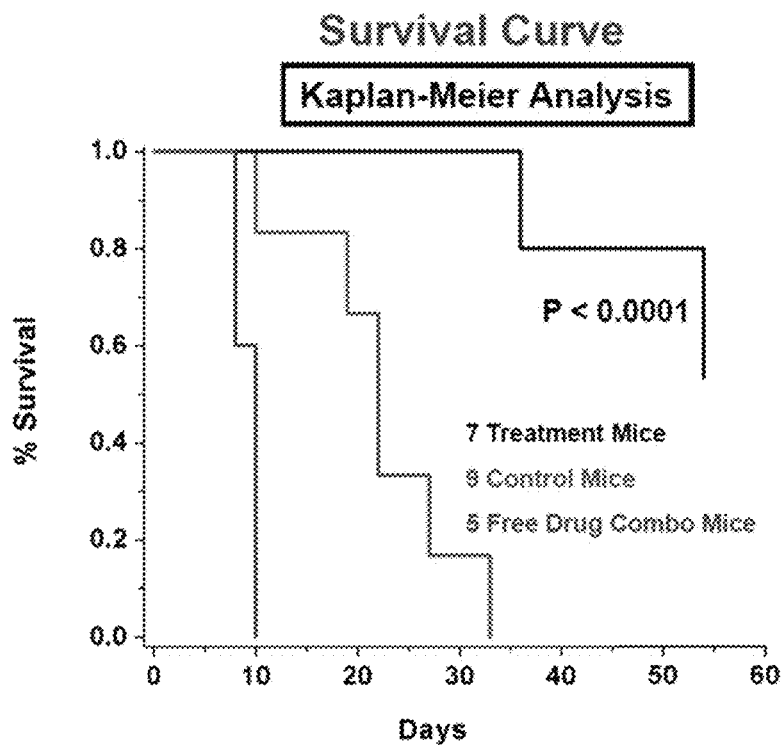
Figure 24D:
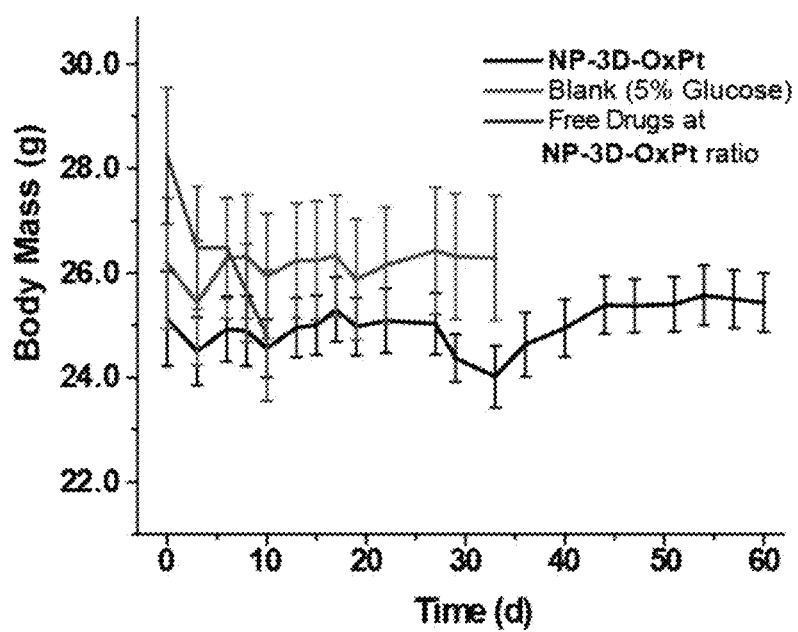

FIGS. 24A to 24D show tumor localization of NP-3D-OxPt-Cy5.5 in NCR-NU mice injected with 5 mg of the three-drug-loaded nanoparticle and monitoring (excitation at 675 nm; emission at 720 nm) the epifluorescence at 3 and 20 h in an IVIS whole animal imaging system (FIG. 24A), a tumor volume plot and treatment schedule for the in vivo evaluation of mice possessing 0.5 cm in diameter subcutaneous xenograft tumors (FIG. 24B), a survival curve illustrating the survival probability of the nanoparticle treated mice versus the control mice that were only injected with 5% glucose solutions (FIG. 24C), and the average body mass of the nanoparticle, control, and free drug treated groups monitored over the course of 60 days (FIG. 24D). Mice treated with the free drug formulation show significant (>10%) weight loss, whereas the NP treated and vehicle control mice demonstrate consistent body masses.

Figure 25:
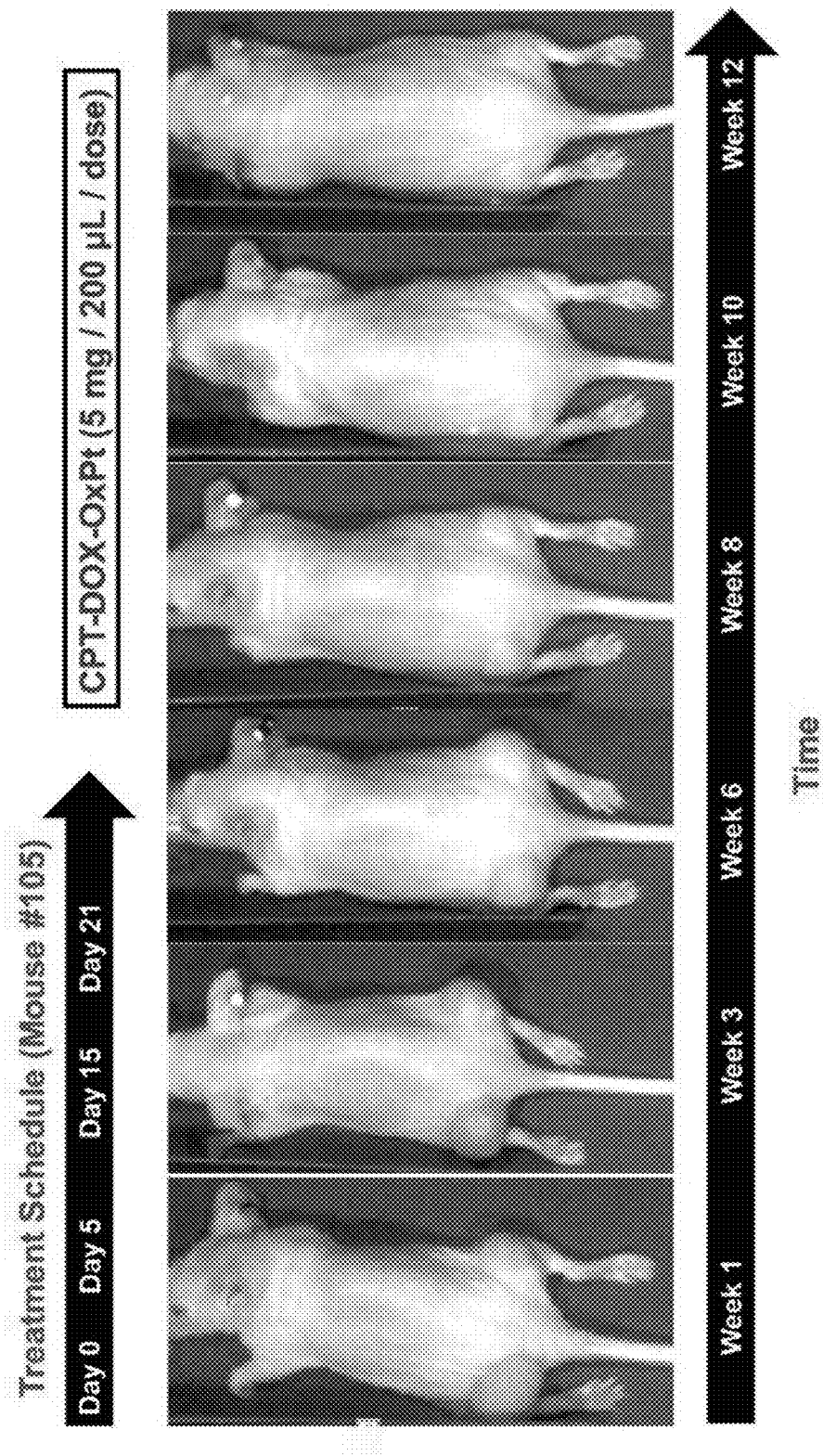

FIG. 25 shows the treatment schedule of Mouse #105 with CPT-DOX-OxPt over a 21 day period. After a 12 week period, nearly complete tumor reduction was observed.

Figure 26:
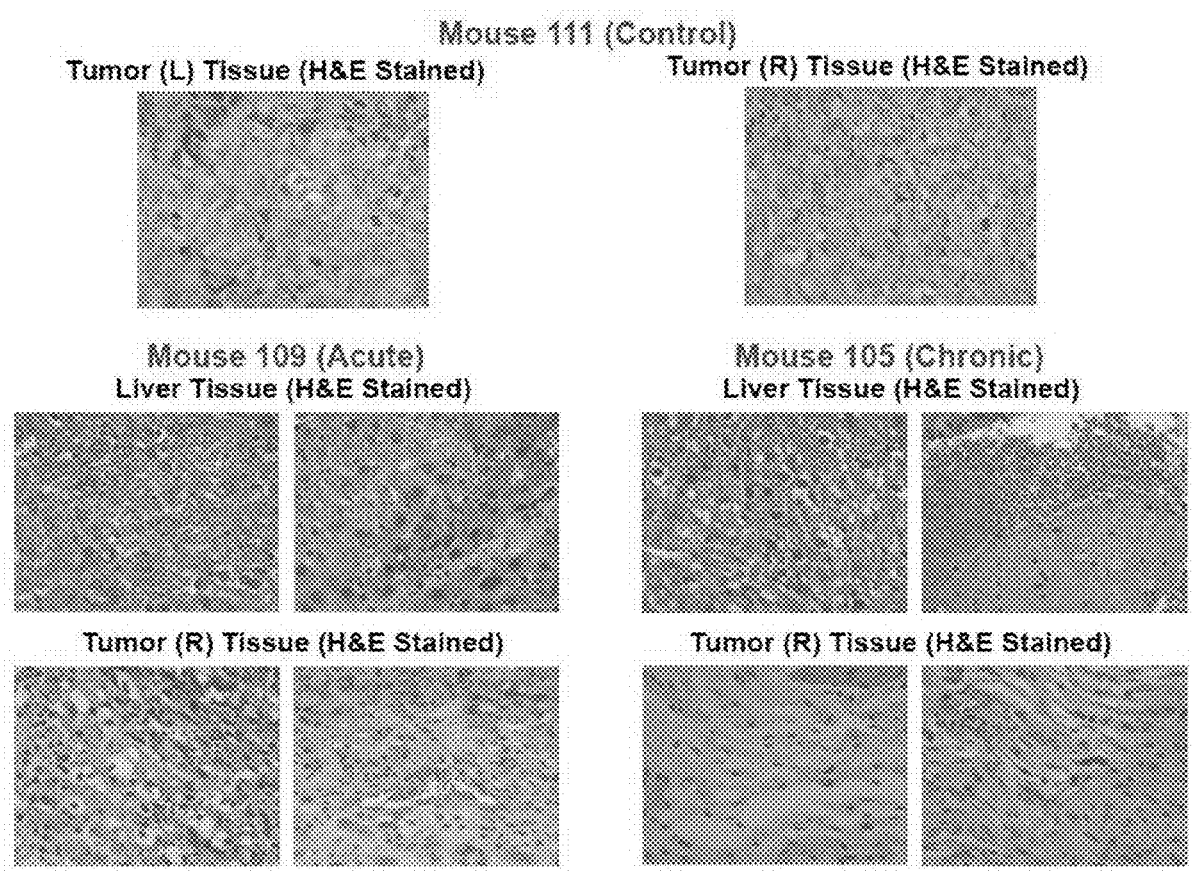

FIG. 26 shows different views of H&E stained left (L) and right (R) tumor cross sections obtained from a control mouse (FIG. 26, top panel), H&E stained liver cross sections obtained from acute and chronic mice (FIG. 26, middle panel), and H&E stained right (R) tumor cross sections obtained from acute and chronic mice (FIG. 26, bottom panel).

Figure 27:
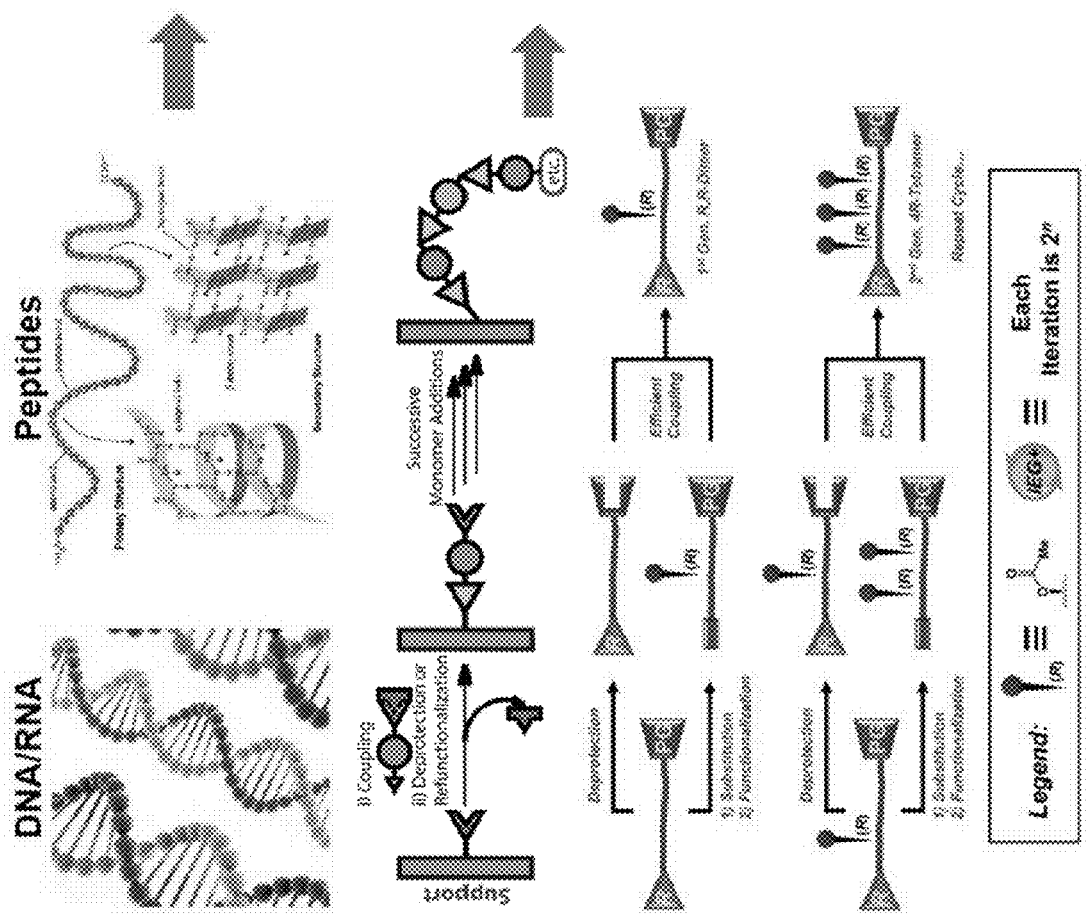

FIG. 27 shows the general scheme for iterative exponential growth (IEG+).

Figure 28A:
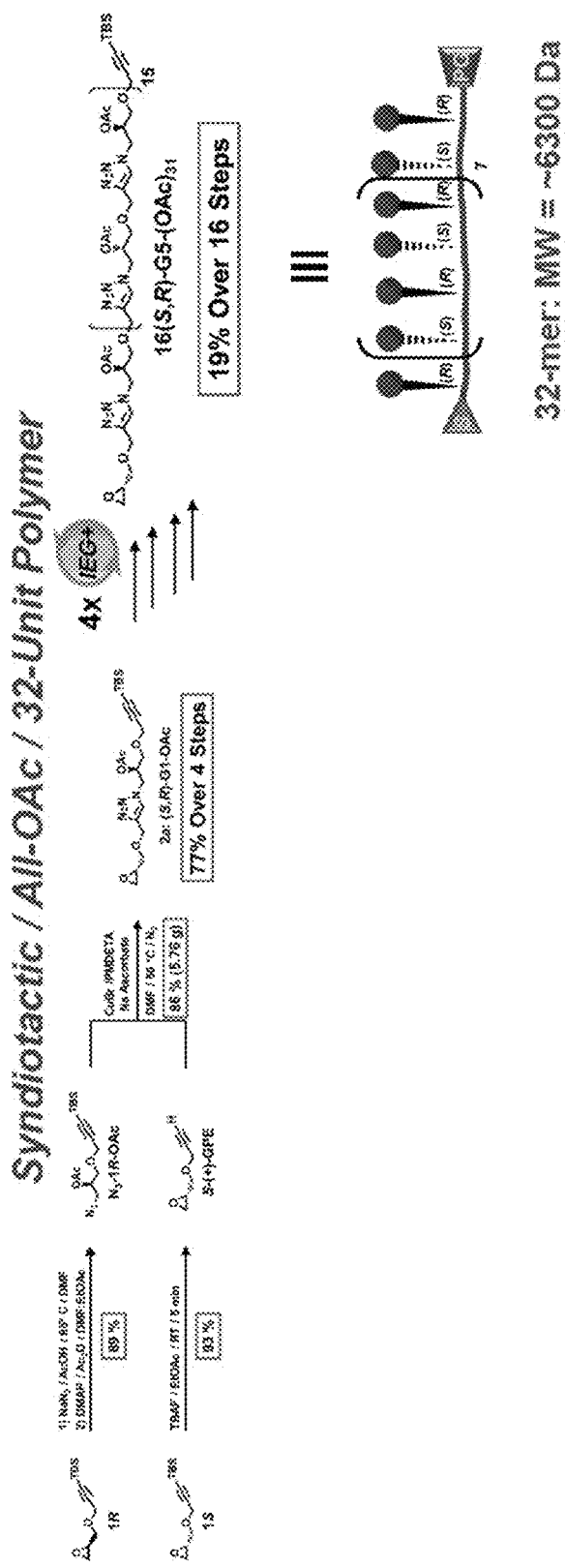
Figure 28B:
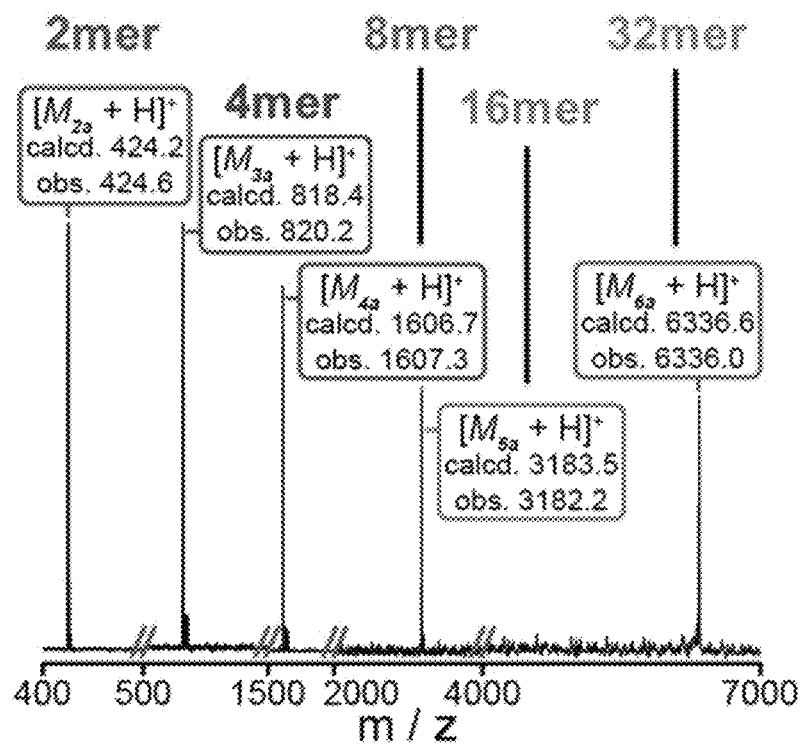
Figure 28C:
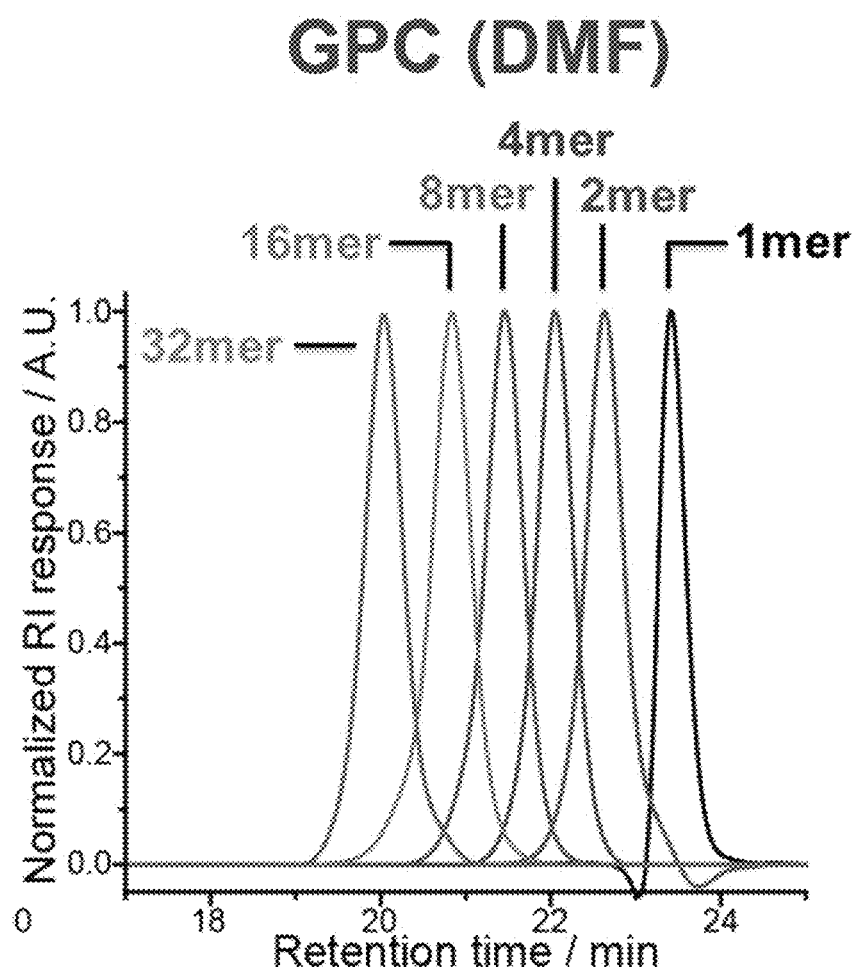
Figure 28D:
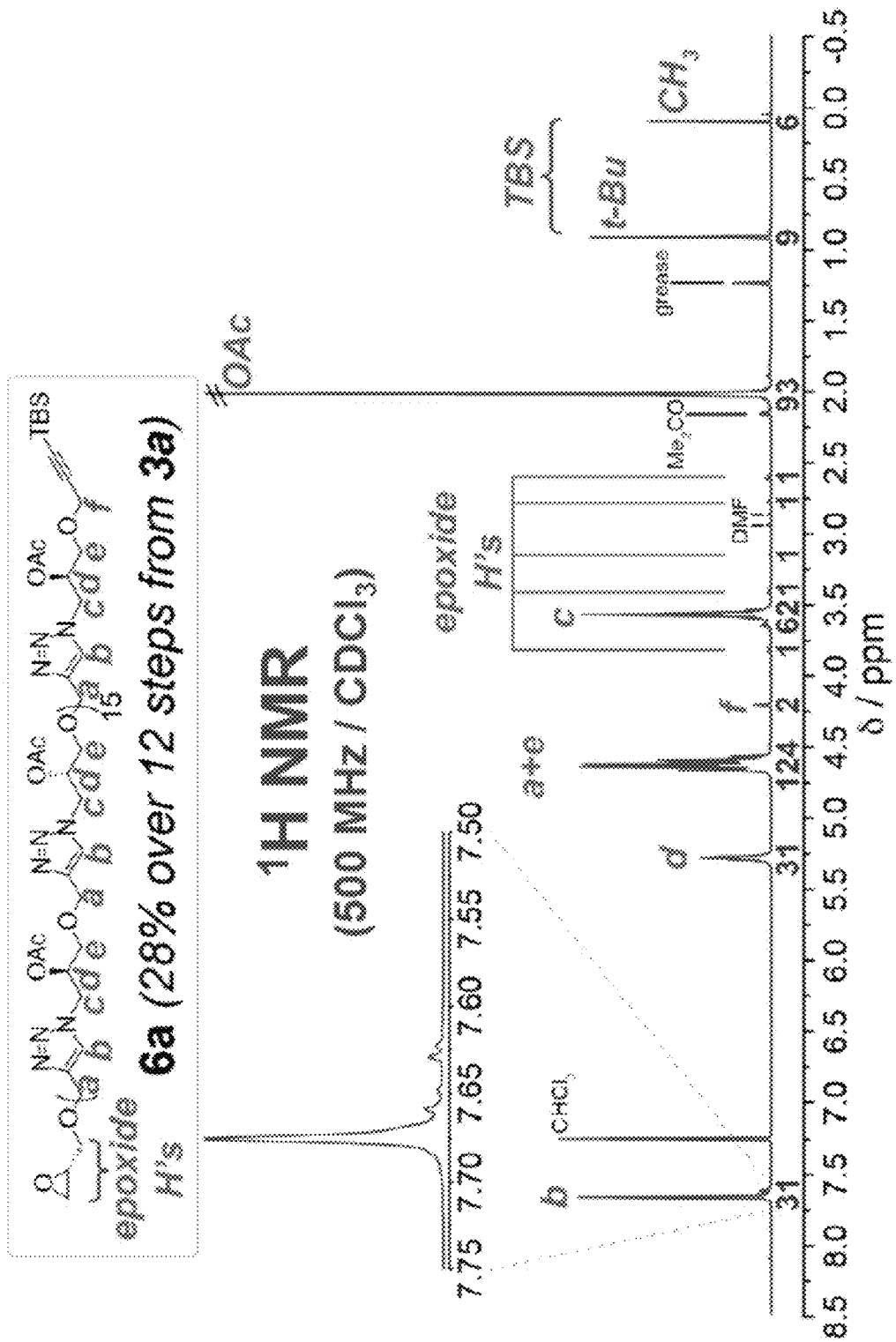

FIGS. 28A to 28D show the general synthesis of syndiotactic 32-unit homopolymer blocks (FIG. 28A) and further analysis using matrix-assisted laser desorption/ionization (MALDI) (FIG. 28B), GPC (FIG. 28C), and $^1$H NMR (FIG. 28D).

Figure 29:
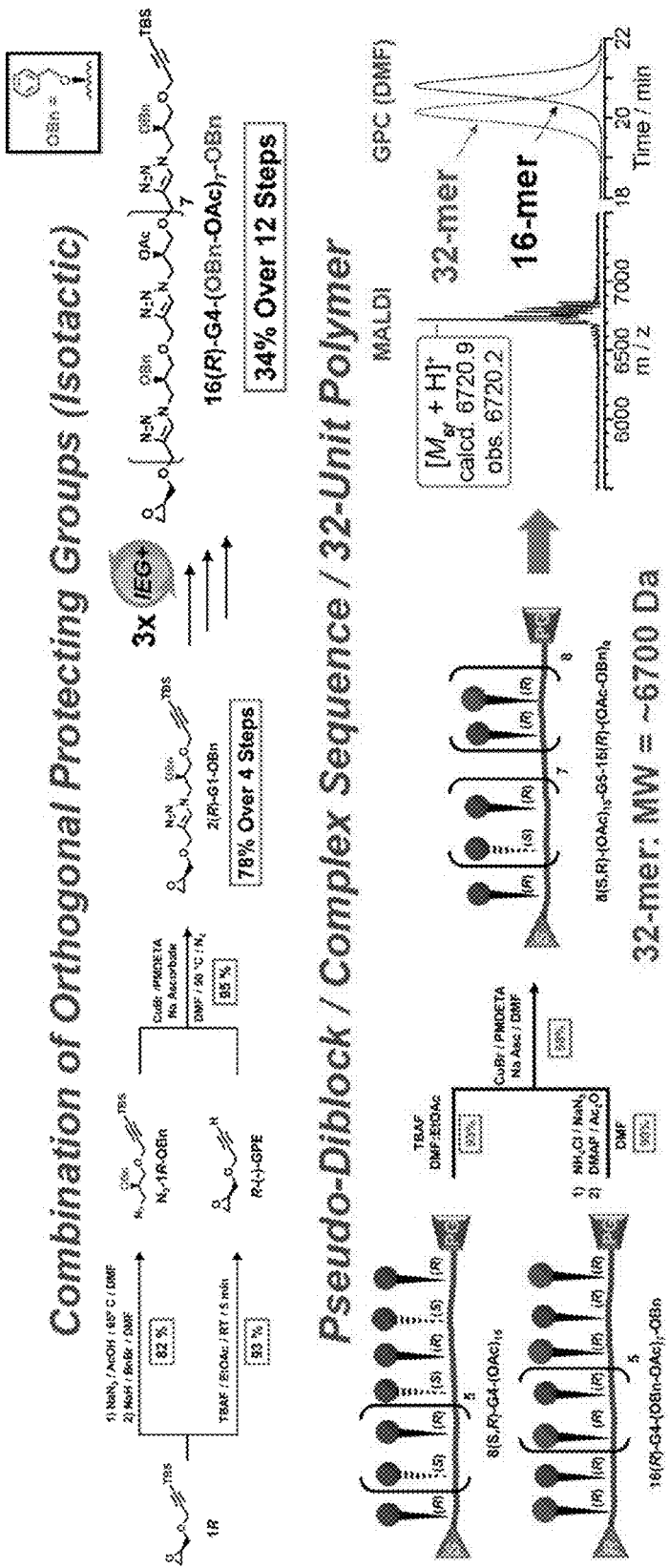

FIG. 29 shows the general synthesis of pseudo-diblock 32-unit alternating copolymer blocks and further analysis using MALDI and GPC.

DETAILED DESCRIPTION OF CERTAIN EMBODIMENTS OF THE INVENTION

Oxaliplatin and related derivatives are widely used in cancer chemotherapy. Significant adverse reactions related to oxaliplatin and related derivatives frequently limits the use of higher doses to achieve their maximum antineoplastic effects. The present invention provides platinum-based brush-arm star polymers (Pt-BASPs) and methods for the controlled delivery of oxaliplatin and related compounds. In certain embodiments, the Pt-BASPs are loaded with a bis-norbornene oxaliplatin crosslinker (oxPt-XL). In certain embodiments, the Pt-BASPs are loaded with oxPt-XL and one or more therapeutic, diagnostic, or prophylactic agents for multi-agent delivery.

Oxaliplatin or its Derivative Crosslinkers

In one aspect, the present invention provides a platinum complex of Formula (I):

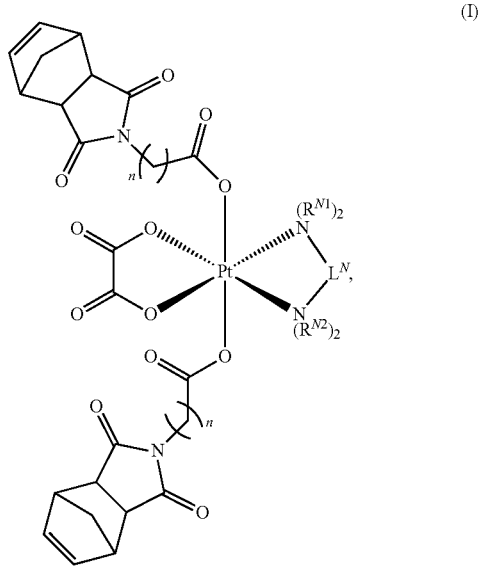

(I)

or salts thereof,
wherein:

each instance of $R^{N1}$ is independently hydrogen, substituted or unsubstituted $C_{1-6}$ alkyl, a nitrogen protecting group, or two $R^{N1}$ are taken with the intervening atoms to form a heterocyclic ring;

each instance of $R^{N2}$ is independently hydrogen, substituted or unsubstituted $C_{1-6}$ alkyl, or a nitrogen protecting group, or two $R^{N2}$ are taken with the intervening atoms to form a heterocyclic ring;

$L^N$ is a linker selected from the group consisting of substituted or unsubstituted alkylene, substituted or unsubstituted heteroalkylene, substituted or unsubstituted arylene, substituted or unsubstituted heterarylene, substituted or unsubstituted cycloalkylene, substituted or unsubstituted heterocyclylene, and combinations thereof; and each instance of n is 1, 2, 3, 4, 5, or 6.

As generally defined herein, each instance of $R^{N1}$ is independently hydrogen, optionally substituted $C_{1-6}$ alkyl, or a nitrogen protecting group, or two $R^{N1}$ are taken with the intervening atoms to form a heterocyclic ring. In certain embodiments, at least one instance of $R^{N1}$ is hydrogen. In certain embodiments, each instance of $R^{N1}$ is hydrogen. In certain embodiments, at least one instance of $R^{N1}$ is optionally substituted $C_{1-6}$ alkyl. In certain embodiments, each instance of $R^{N1}$ is optionally substituted $C_{1-6}$ alkyl. In certain embodiments, $R^{N1}$ is substituted $C_{1-6}$ alkyl. In certain embodiments, $R^{N1}$ is unsubstituted $C_{1-6}$ alkyl. In certain embodiments, $R^{N1}$ is methyl. In certain embodiments, $R^{N1}$ is ethyl. In certain embodiments, $R^{N1}$ is a nitrogen protecting group. In certain embodiments, two $R^{N1}$ are taken with the intervening atoms to form a heterocyclic ring.

As generally defined herein, each instance of $R^{N2}$ is independently hydrogen, optionally substituted $C_{1-6}$ alkyl, or a nitrogen protecting group, or two $R^{N2}$ are taken with the intervening atoms to form a heterocyclic ring, or $R^{N1}$ and $R^{N2}$ are taken with the intervening atoms to form a heterocyclic ring. In certain embodiments, at least one instance of $R^{N2}$ is hydrogen. In certain embodiments, each instance of $R^{N2}$ is hydrogen. In certain embodiments, at least one instance of $R^{N2}$ is optionally substituted $C_{1-6}$ alkyl. In certain embodiments, each instance of $R^{N2}$ is optionally substituted $C_{1-6}$ alkyl. In certain embodiments, $R^{N2}$ is substituted $C_{1-6}$ alkyl. In certain embodiments, $R^{N2}$ is unsubstituted $C_{1-6}$ alkyl. In certain embodiments, $R^{N2}$ is methyl. In certain embodiments, $R^{N2}$ is ethyl. In certain embodiments, $R^{N2}$ is a nitrogen protecting group. In certain embodiments, two $R^{N2}$ are taken with the intervening atoms to form a heterocyclic ring. In certain embodiments, $R^{N1}$ and $R^{N2}$ are taken with the intervening atoms to form a heterocyclic ring.

In certain embodiments, $R^{N1}$ and $R^{N2}$ are the same. In certain embodiments, $R^{N1}$ and $R^{N2}$ are different. In certain embodiments, all instances of $R^{N1}$ and $R^{N2}$ are hydrogen. In certain embodiments, at least one instance of $R^{N1}$ is hydrogen and at least one instance of $R^{N2}$ is not hydrogen. In certain embodiments, at least one instance of $R^{N1}$ is hydrogen and at least one instance of $R^{N2}$ is optionally substituted $C_{1-6}$ alkyl. In certain embodiments, at least one instance of $R^{N1}$ is hydrogen and at least one instance of $R^{N2}$ is substituted $C_{1-6}$ alkyl. In certain embodiments, at least one instance of $R^{N1}$ is hydrogen and at least one instance of $R^{N2}$ is unsubstituted $C_{1-6}$ alkyl. In certain embodiments, at least one instance of $R^{N1}$ is hydrogen and at least one instance of $R^{N2}$ is methyl, ethyl, or propyl. In certain embodiments, at least one instance of $R^{N1}$ and at least one instance of $R^{N2}$ are each independently optionally substituted $C_{1-6}$ alkyl. In certain embodiments, at least one instance of $R^{N1}$ and at least one instance of $R^{N2}$ are each independently substituted $C_{1-6}$ alkyl. In certain embodiments, at least one instance of $R^{N1}$ and at least one instance of $R^{N2}$ are each independently unsubstituted $C_{1-6}$ alkyl. In certain embodiments, at least one instance of $R^{N1}$ and at least one instance of $R^{N2}$ are each independently is methyl, ethyl, or propyl. In certain embodiments, at least one instance of $R^{N1}$ and at least one instance of $R^{N2}$ are each independently a nitrogen protecting group.

As generally defined herein, $L^N$ is a linker selected from the group consisting of substituted or unsubstituted alkylene, substituted or unsubstituted heteroalkylene, substituted or unsubstituted arylene, substituted or unsubstituted heterarylene, substituted or unsubstituted cycloalkylene, substituted or unsubstituted heterocyclylene, and combinations (e.g., combination of two, three, or four) thereof. In certain embodiments, $L^N$ is substituted or unsubstituted alkylene. In certain embodiments, $L^N$ is substituted alkylene. In certain embodiments, $L^N$ is unsubstituted alkylene (e.g., methylene, ethylene, or propylene). In certain embodiments, $L^N$ is substituted or unsubstituted heteroalkylene. In certain embodiments, $L^N$ is substituted or unsubstituted arylene. In certain embodiments, $L^N$ is substituted or unsubstituted phenylene. In certain embodiments, $L^N$ is substituted or unsubstituted heterarylene. In certain embodiments, $L^N$ is substituted or unsubstituted 5-membered or 6-membered heterarylene. In certain embodiments, $L^N$ is substituted or unsubstituted cycloalkylene. In certain embodiments, $L^N$ is substituted or unsubstituted cyclohexylene. In certain embodiments, $L^N$ is substituted or unsubstituted cyclohexylene, wherein the point of attachments are 1- and 4-positions. In certain embodiments, $L^N$ is substituted or unsubstituted cyclohexylene, wherein the point of attachments are 1- and 3-positions. In certain embodiments, $L^N$ is substituted or unsubstituted cyclohexylene, wherein the point of attachments are 1- and 2-positions.

In certain embodiments, $L^N$ is substituted or unsubstituted cycloalkylene and $R^{N1}$ and $R^{N2}$ are the same. In certain embodiments, $L^N$ is substituted or unsubstituted cyclohexylene and $R^{N1}$ and $R^{N2}$ are hydrogen. In certain embodiments, $L^N$ is substituted or unsubstituted cyclohexylene, wherein the point of attachments are 1- and 4-positions, and $R^{N1}$ and $R^{N2}$ are hydrogen.

In certain embodiments, the number of atoms in the shortest backbone of $L^N$ is 1. In certain embodiments, the number of atoms in the shortest backbone of $L^N$ is 2. In certain embodiments, the number of atoms in the shortest backbone of $L^N$ is 3. In certain embodiments, the number of atoms in the shortest backbone of $L^N$ is 4.

As generally defined herein, n is 1, 2, 3, 4, 5, or 6. In certain embodiments, n is 1. In certain embodiments, n is 2. In certain embodiments, n is 3. In certain embodiments, n is 4. In certain embodiments, n is 5. In certain embodiments, n is 6.

In certain embodiments, the platinum complexes of Formula (I) are prodrugs of the oxaliplatin. The Pt—O bond can be cleaved by a reducing agent in vivo to release oxaliplatin. In certain embodiments, the platinum complex of Formula (I) is used as a crosslinker to prepare polymers for the controlled release of oxaliplatin. In certain embodiments, the platinum complex of Formula (I) is used as a crosslinker to prepare Pt-BASP.

In certain embodiments, the platinum complex of Formula (I) is of Formula (I-a):

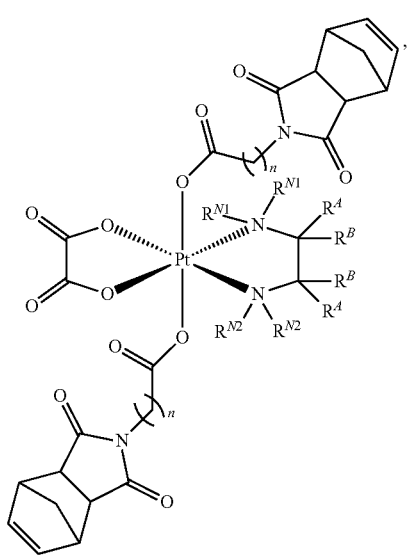

(I-a)

or a salt thereof,
wherein:
each instance of $R^A$ is independently hydrogen, halogen, substituted or unsubstituted alkyl, substituted or unsubstituted carbocyclyl, substituted or unsubstituted heterocyclyl, substituted or unsubstituted aryl, substituted or unsubstituted heteroaryl; and each instance of RB is independently hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl;

or two instances of $R^B$ are joined to form a substituted or unsubstituted, carbocyclic ring, or substituted or unsubstituted, heterocyclic ring.

In certain embodiments, the platinum complex of Formula (I) is of Formula (I-b):

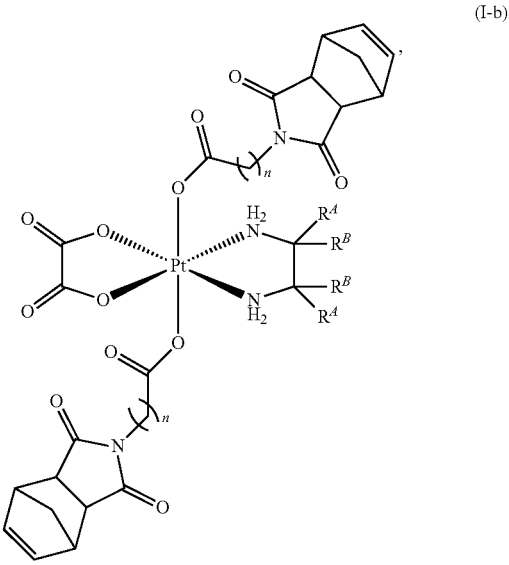

(I-b)

or a salt thereof.

In certain embodiments, at least one instance of $R^A$ is hydrogen. In certain embodiments, each instance of $R^A$ is hydrogen. In certain embodiments, at least one instance of $R^A$ is substituted or unsubstituted alkyl (e.g., substituted or unsubstituted $C_{1-6}$ alkyl). In certain embodiments, at least one instance of $R^A$ is unsubstituted alkyl (e.g., unsubstituted $C_{1-6}$ alkyl, such as methyl, ethyl, or propyl). In certain embodiments, at least one instance of $R^A$ is substituted alkyl (e.g., substituted $C_{1-6}$ alkyl). In certain embodiments, at least one instance of $R^A$ is halogen (e.g., F).

In certain embodiments of Formulae (I-a)-(I-b), at least one instance of $R^A$ is hydrogen. In certain embodiments of Formulae (I-a)-(I-b), both instances of $R^A$ are hydrogen. In certain embodiments of Formulae (I-a)-(I-b), at least one instance of $R^A$ is substituted or unsubstituted alkyl. In certain embodiments of Formulae (I-a)-(I-b), at least one instance of $R^A$ is unsubstituted alkyl. In certain embodiments of Formulae (I-a)-(I-b), at least one instance of $R^A$ is substituted alkyl.

In certain embodiments, at least one instance of $R^B$ is hydrogen. In certain embodiments, each instance of $R^B$ is hydrogen. In certain embodiments, at least one instance of $R^B$ is substituted or unsubstituted alkyl (e.g., substituted or unsubstituted $C_{1-6}$ alkyl). In certain embodiments, at least one instance of $R^B$ is unsubstituted alkyl (e.g., unsubstituted $C_{1-6}$ alkyl, such as methyl, ethyl, or propyl). In certain embodiments, at least one instance of $R^B$ is substituted alkyl (e.g., substituted $C_{1-6}$ alkyl). In certain embodiments, at least one instance of $R^B$ is halogen (e.g., F).

In certain embodiments of Formulae (I-a)-(I-b), at least one instance of $R^B$ is hydrogen. In certain embodiments of Formulae (I-a)-(I-b), both instances of $R^B$ are hydrogen. In certain embodiments of Formulae (I-a)-(I-b), at least one instance of $R^B$ is substituted or unsubstituted alkyl. In certain embodiments of Formulae (I-a)-(I-b), at least one instance of $R^B$ is unsubstituted alkyl. In certain embodiments of Formulae (I-a)-(I-b), at least one instance of $R^B$ is substituted alkyl. In certain embodiments of Formulae (I-a)-(I-b), two $R^B$ are joined to form a substituted or unsubstituted, carbocyclic ring, or substituted or unsubstituted, heterocyclic ring. In certain embodiments of Formulae (I-a)-(I-b), two $R^B$ are joined to form a substituted or unsubstituted carbocyclic ring. In certain embodiments of Formulae (I-a)-(I-b), two $R^B$ are joined to form a substituted or unsubstituted cyclohexyl ring.

In certain embodiments, the platinum complex of Formula (I) is of Formula (I-c):

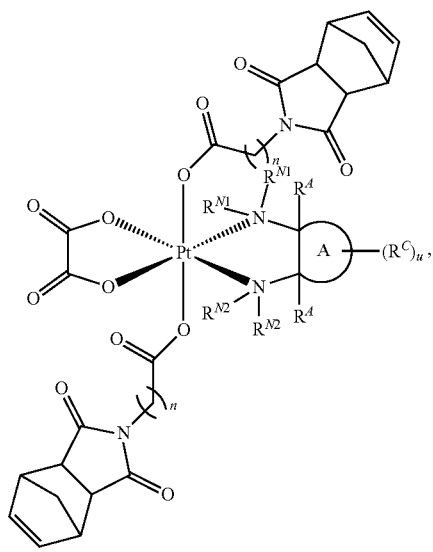

(I-c)

or a salt thereof,
wherein:

Ring A is a substituted or unsubstituted, monocyclic, 3- to 7-membered carbocyclic ring;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^a$, $-N(R^a)_2$, $-SR^a$, $-CN$, $-SCN$, $-C(=NR^a)R^a$, $-C(=NR^a)OR^a$, $-C(=NR^a)N(R^a)_2$, $-C(=O)R^a$, $-C(=O)OR^a$, $-C(=O)N(R^a)_2$, $-NO_2$, $-N(R^a)C(=O)R^a$, $-N(R^a)C(=O)OR^a$, $-N(R^a)C(=O)N(R^a)_2$, $-N(R^a)S(=O)R^a$, $-N(R^a)S(=O)OR^a$, $-N(R^a)S(=O)N(R^a)_2$, $-N(R^a)S(=O)_2R^a$, $-N(R^a)S(=O)_2OR^a$, $-N(R^a)S(=O)_2N(R^a)_2$, $-OC(=O)R^a$, $-OC(=O)OR^a$, or $-OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring; and u is an integer between 0 and 8, inclusive.

In certain embodiments, the platinum complex of Formula (I) is of Formula (I-d):

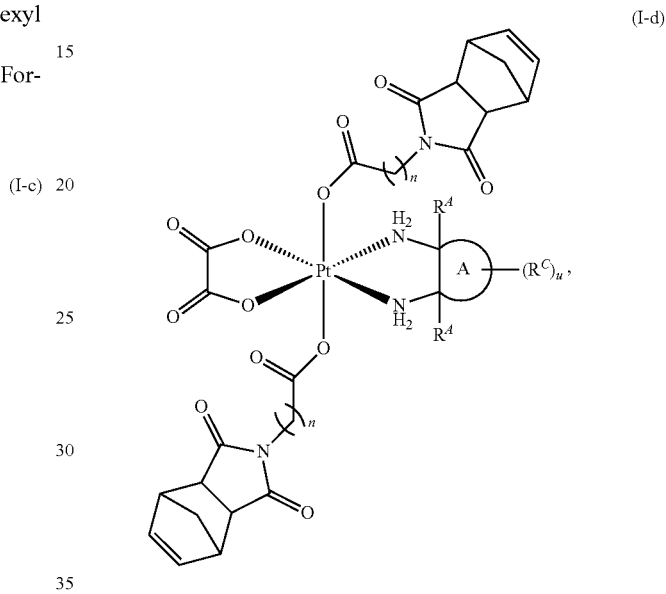

(I-d)

or a salt thereof.

In certain embodiments of Formulae (I-c) and (I-d), Ring A is a substituted or unsubstituted cyclopropyl ring. In certain embodiments of Formulae (I-c) and (I-d), Ring A is a substituted or unsubstituted cyclobutyl ring. In certain embodiments of Formulae (I-c) and (I-d), Ring A is a substituted or unsubstituted cyclopentyl ring. In certain embodiments of Formulae (I-c) and (I-d), Ring A is a substituted or unsubstituted cyclohexyl ring. In certain embodiments of Formulae (I-c) and (I-d), Ring A is a substituted or unsubstituted cycloheptyl ring.

In certain embodiments of Formula (I-d), $R^A$ is hydrogen. In certain embodiments of Formula (I-d), $R^A$ is substituted or unsubstituted alkyl. In certain embodiments of Formula (I-d), $R^A$ is unsubstituted alkyl (e.g., methyl, ethyl, or propyl). In certain embodiments of Formula (I-d), $R^A$ is substituted alkyl.

In certain embodiments, at least one instance of $R^C$ is hydrogen. In certain embodiments, each instance of $R^C$ is hydrogen. In certain embodiments, at least one instance of $R^C$ is substituted or unsubstituted alkyl (e.g., substituted or unsubstituted $C_{1-6}$ alkyl). In certain embodiments, at least one instance of $R^C$ is unsubstituted alkyl (e.g., unsubstituted $C_{1-6}$ alkyl, such as methyl, ethyl, or propyl). In certain embodiments, at least one instance of $R^C$ is substituted alkyl (e.g., substituted $C_{1-6}$ alkyl). In certain embodiments, at least one instance of $R^C$ is halogen (e.g., F). In certain embodiments, each instance of $R^C$ is the same.

In certain embodiments, the platinum complex of Formula (I) is of Formula (I-e):

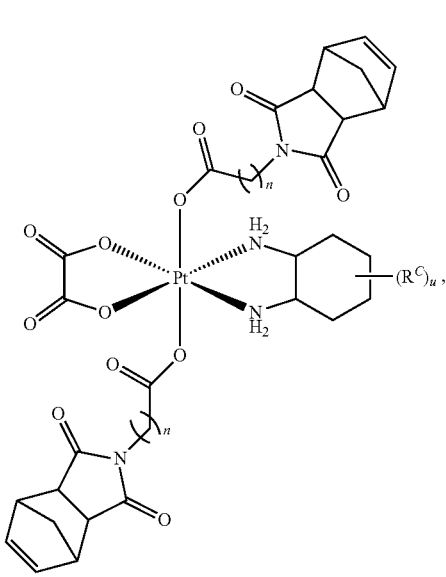
(I-e)

or a salt thereof.

In certain embodiments of Formulae (I-c)-(I-e), u is 0. In certain embodiments of Formulae (I-c)-(I-e), u is 2. In certain embodiments of Formulae (I-c)-(I-e), u is 3. In certain embodiments of Formulae (I-c)-(I-e), u is 4. In certain embodiments of Formulae (I-c)-(I-e), u is 5. In certain embodiments of Formulae (I-c)-(I-e), u is 6. In certain embodiments of Formulae (I-c)-(I-e), u is 7. In certain embodiments of Formulae (I-c)-(I-e), u is 8.

In certain embodiments, the platinum complex of Formula (I) is of Formula (I-f):

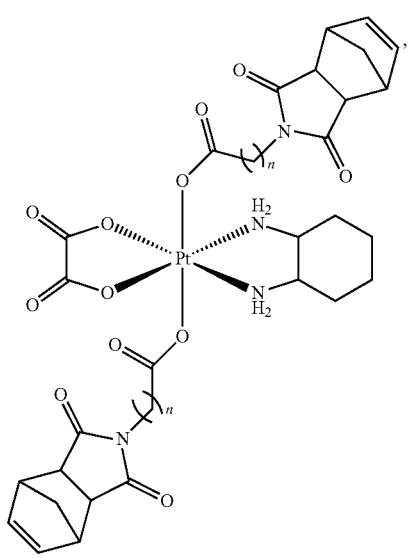
(I-f)

or a salt thereof.

As generally used herein,

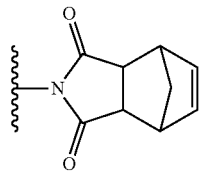 [SMILES: *N1C(=O)C2C3C=CC(C3)C2C1=O]

encompasses a racemic moiety or any stereoisomer thereof. In certain embodiments, at least one instance of

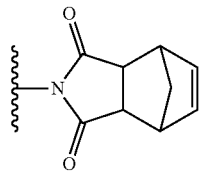 [SMILES: *N1C(=O)C2C3C=CC(C3)C2C1=O]

is of one of the following formulae:

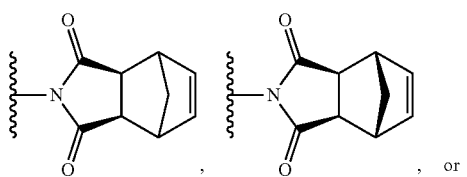, or

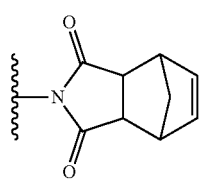 [SMILES: *N1C(=O)C2C3C=CC(C3)C2C1=O]

In certain embodiments, each instance of

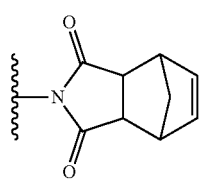 [SMILES: *N1C(=O)C2C3C=CC(C3)C2C1=O]

is of one of the following formulae:

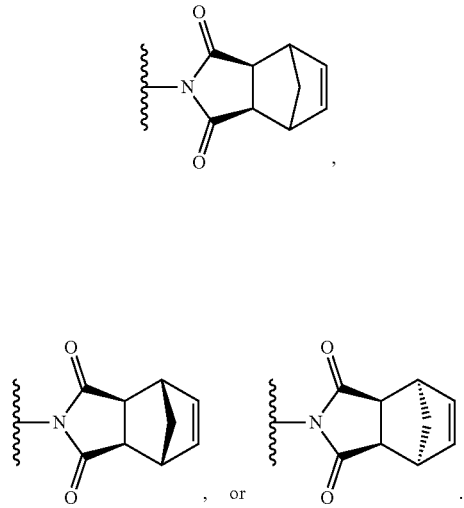

In certain embodiments, each instance of is of the formula:

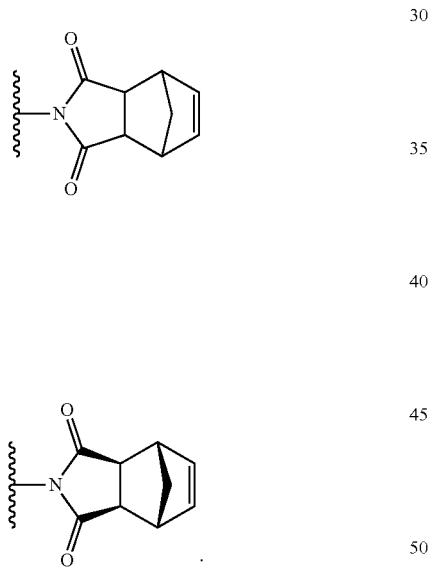

In certain embodiments, the provided platinum complex is of the formula:

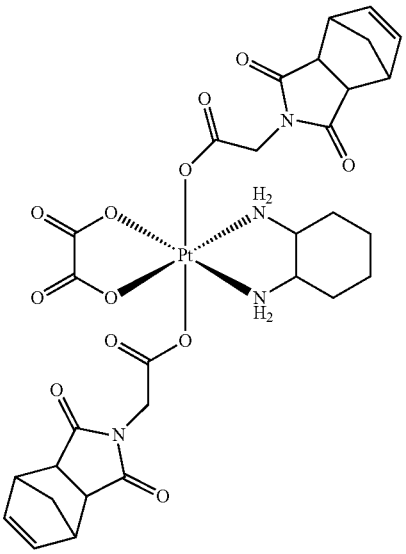

In certain embodiments, the provided platinum complex is of the formula:

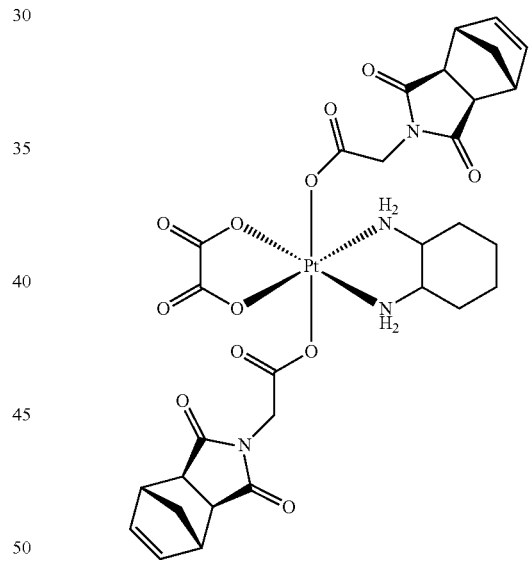

The platinum complex of Formula (I) can be prepared using the general methodology shown in Scheme 1. Details of the synthetic procedures are described in the Examples below.

Scheme 1

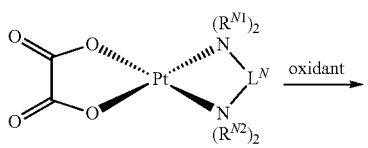

-continued

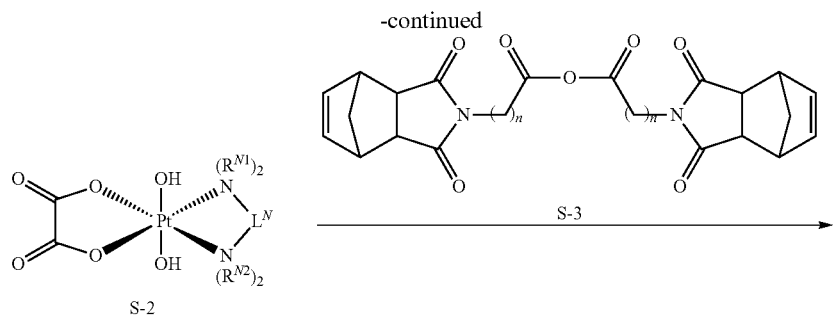

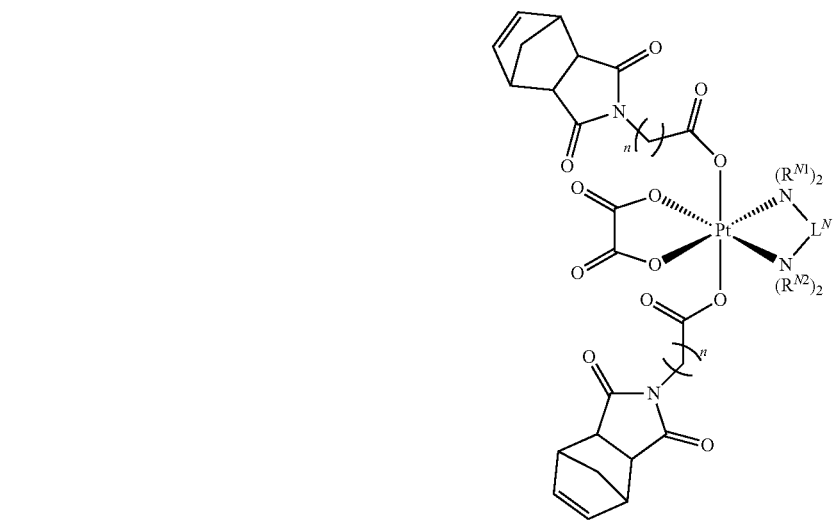

In one embodiments, the invention provides methods of preparing a platinum complex of Formula (I), the method comprising steps of:

(a) oxidizing a compound of Formula (S-I) with an oxidant

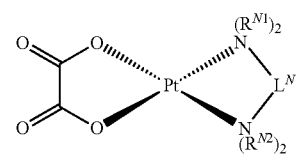

to yield a compound of Formula (S-2):

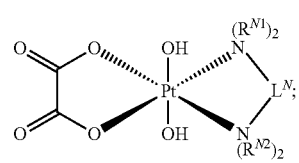

wherein $R^{N1}$, $R^{N2}$, $L^N$, and n are as defined herein; and (b) coupling the compound of Formula (S-2) with a compound of Formula (S-3):

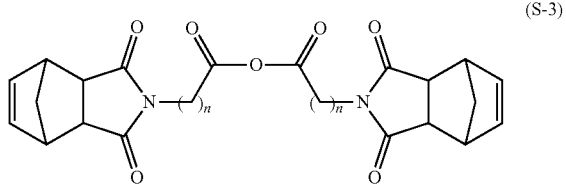

to yield a platinum complex of Formula (I).

In certain embodiments, the oxidant used in step (a) can oxidize Pt (II) to Pt (IV) with two hydroxyl groups under suitable oxidization condition (Hall et al., *J. Biol. Inorg. Chem.* 2003, 8, 726). In certain embodiments, the oxidant is $H_2O_2$.

In certain embodiments, an activator is present in the coupling reaction in step (b). The activator converts the compound of Formula (S-3) to an activated ester for the coupling reaction. Examples of useful activators are dicyclohexylcarbodiimide (DCC), 1-ethyl-3-(3-dimethylaminopropyl)carbodiimide hydrochloride (WSC/HCl), diphenylphosphorylazide (DPPA), carbonyldiimidazole (CDI), diethylcyanophosphonate (DEPC), benzotriazole-1-yloxytrispyrrolidinophosphonium (DIPCI), benzotriazole-1-yloxy-trispyrrolidinophosphonium hexafluorophosphate (PyBOP), 1-hydroxybenzotriazole (HOBt), hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 2-(1H-benzotriazole-1-yl)-1,1,3,3-tetramethyluronium hexafluorophosphate (HBTU), O-(7-azabenzotriazole-1-yl)-1,1,3,3-tetramethyluronium hexafluorophosphonate (HATU), O-benzotriazole-1-yl-1,1,3,3-tetramethyluronium tetrafluoroborate (TBTU), 3,4-dihydro-3-hydrodi-4-oxa-1,2,3-benzotriazine (Dhbt). In certain embodiments, the activator is DCC.

The activator is used in an amount of about 1 to 20 equivalents of the compound of Formula (S-2). In certain embodiments, the activator is used in an amount of about 1 to 10 equivalents. In certain embodiments, the activator is used in an amount of about 1 to 5 equivalents.

Examples of useful solvents in the coupling reaction are DMSO, DMF, methylene chloride. The coupling reaction can be conducted at 0 to 50° C. In certain embodiments, the coupling reaction is conducted at room temperature for about 10 min to about 30 hours. In certain embodiments, the coupling reaction is conducted for about 15 minutes to about 24 hours.

Platinum-Based Brush-Arm Star Polymers (Pt-BASPs)

The present invention provides platinum-based brush-arm star polymers (Pt-BASP) using the "brush-first" ring-opening metathesis polymerization (ROMP). The brush-first method involves sequential copolymerization of two functional monomers, a polymeric macromonomer (MM) followed by a multifunctional crosslinker, to generate a unimolecular micelle-like nanostructure with a core comprised of oxaliplatin or a derivative thereof crosslinker and a corona comprised of the MM. Synthesis of Pt-BASPs is generally described in International Application No. PCT/US2014/033554 filed Apr. 9, 2014, which is incorporated by reference in its entirety herein.

A Pt-BASP described herein includes oxaliplatin or a derivative thereof attached to the rest of the Pt-BASP through ester bonds. Oxaliplatin is a clinically approved chemotherapeutic agent that includes a platinum(II) core, the bidentate ligand, 1,2-diaminocyclohexane, and a bidentate oxalate group.

In addition to oxaliplatin or a derivative thereof, a Pt-BASP described herein may include one or more additional agents that are not oxaliplatin or a derivative thereof to form multi-agent-loaded (e.g., multi-drug-loaded) Pt-BASPs. The described Pt-BASPs are advantageous over known nanoparticle (NP)-based delivery systems. NP-based combination cancer therapy has the potential to overcome the toxicity and poorly controlled dosing of traditional systemic combination therapies (Hu, C. M. J.; Zhang, L. F. *Biochem. Pharmacol.* 2012, 83, 1104; Yan, Y.; Bjornmalm, M.; Caruso, F. *ACS Nano* 2013, 7, 9512; Ma, L.; Kohli, M.; Smith, A. *ACS Nano* 2013, 7, 9518). Though NP-based therapeutics for cancer therapy have been the subject of numerous investigations over the past several decades (Duncan, R. *Nat. Rev. Drug Discovery* 2003, 2, 347; Peer et al. *Nat. Nanotechnol.* 2007, 2, 751; Wolinsky, J. B.; Grinstaff, M. W. *Adv. Drug Delivery Rev.* 2008, 60, 1037; Davis, M. E.; Chen, Z.; Shin, D. M. *Nat. Rev. Drug Discovery* 2008, 7, 771; Kwon, G. S.; Kataoka, K. *Adv. Drug Delivery Rev.* 2012, 64, 237), ratiometric, synchronized release of multiple drugs from single NP scaffolds remains a challenge (Sengupta et al. Nature 2005, 436, 568; Lammers et al. Biomaterials 2009, 30, 3466; Kolishetti, N.; Dhar, S.; Valencia, P. M.; Lin, L. Q.; Karnik, R.; Lippard, S. J.; Langer, R.; Farokhzad, O. C. *Proc. Natl. Acad. Sci. U.S.A* 2010, 107, 17939; Aryal, S.; Hu, C. M. J.; Zhang, L. F. *Mol. Pharm.* 2011, 8, 1401). Many reported nanoparticle architectures for delivery, e.g., liposomes, micelles, and dendrimers, are not readily amenable to controlled incorporation and release of multiple drugs.

In contrast, the Pt-BASPs described herein are able to deliver multiple agents (e.g., cisplatin and one or more other agents) ratiometrically. The agents included in a Pt-BASP may show different therapeutic, diagnostic, and/or prophylactic effects on a subject, tissue, or cell. For example, a Pt-BASP may include two or more therapeutic agents (including oxaliplatin or a derivative thereof), and the therapeutic agents may show different anti-proliferative activities (e.g., anti-cancer activities) at each therapeutic agent's maximum tolerated dose (MTD). A key benefit of single nanoparticle combination therapy is the ability to deliver multiple drugs at a precise ratio to a subject, tissue, or cell, while minimizing undesired effects (e.g., toxicity) associated with multiple drug combinations. To achieve the maximum therapeutic index in a multi-drug combination therapy, simultaneous dosing of each drug at or near each drug's MTD would be ideal. A Pt-BASP described herein may include multiple drugs at or near each drug's MTD before the Pt-BASP is delivered to a subject, tissue, or cell, release the multiple drugs at or near each drug's MTD into the subject, tissue, or cell after delivery, and therefore achieve the maximum therapeutic index. In certain embodiments, Pt-BASPs described herein include camptothecin (CPT) and oxaliplatin or a derivative thereof (e.g., oxPt-XL). In certain embodiments, Pt-BASPs described herein include irinotecan (IRT) and oxaliplatin or a derivative thereof (e.g., oxPt-XL). In certain embodiments, Pt-BASP described herein include SN-38 and oxaliplatin or a derivative thereof (e.g. oxPt-XL). In certain embodiments, Pt-BASPs described herein include 5-FU and oxaliplatin or a derivative thereof (e.g., oxPt-XL). In certain embodiments, Pt-BASPs described herein include IRT, 5-FU, and oxaliplatin or a derivative thereof. In certain embodiments, Pt-BASPs described herein include CPT, 5-FU, and oxaliplatin or a derivative thereof. In certain embodiments, Pt-BASPs described herein include SN-38, 5-FU, and oxaliplatin or a derivative thereof.

The Pt-BASPs described herein are also able to deliver multiple agents orthogonally. Different chemical and/or physical conditions may be employed to individually release the multiple agents upon delivery. The convergent synthesis of Pt-BASPs allow the attachment of different agents to the Pt-BASPs through different linkers (e.g., linkers cleavable by reduction, such as Pt—O bonds; hydrolysable linkers, such as ester bonds; and photo-cleavable linkers, such as the moiety

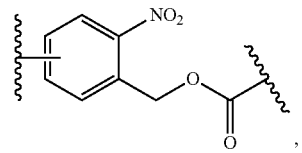

wherein the moiety may be further substituted). For example, oxaliplatin may be released from a Pt-BASP by a reduction reaction of the Pt—O bonds; and other agents included in the Pt-BASP may be released from the Pt-BASP under chemical and/or physical conditions that are different from the reduction reaction. In certain embodiments, an agent, other than oxaliplatin or a derivative thereof, included in a Pt-BASP is released from the Pt-BASP by hydrolysis (e.g., hydrolysis under acidic conditions). In certain embodiments, an agent, other than oxaliplatin or a derivative thereof, included in a Pt-BASP is released from the Pt-BASP by irradiation with ultraviolet light (UV).

The Pt-BASPs described herein can be directly constructed using carefully designed drug-conjugates as building blocks, and no self-assembly is required for preparing the Pt-BASPs. The methods for preparing the Pt-BASPs described herein involves ring-opening metathesis polymerization (ROMP) (Liu et al. *J. Am. Chem. Soc.* 2012, 134, 16337; Liu, J.; Gao, A. X.; Johnson, J. A. *J Vis Exp* 2013, e50874). In certain embodiments, the Pt-BASPs described herein are prepared by polymerization of norbornene-terminated macromonomers (MMs) followed by in situ crosslinking with bis-norbornene crosslinkers. The preparation methods described herein are versatile and have little limitations, e.g., in terms of the different agents that can be built into the Pt-BASPs. In certain embodiments, an agent that can be built into the Pt-BASPs includes addressable functional groups that are compatible with ROMP. In certain embodiments, the invention provides Pt-BASPs prepared by Method A' including the steps of:

(a) reacting a macromonomer of Formula (III'):

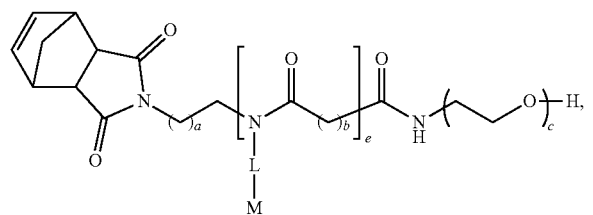

(III')

or a salt thereof, with a metathesis catalyst to form a polymerization mixture, wherein:

a is an integer from 1 to 10, inclusive;
each instance of b is independently an integer from 1 to 10, inclusive;
c is an integer from 1 to 200, inclusive;
e is 0, 1, 2, 3, 4, 5, or 6;
each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a cleavable linker, a polymer, or a substituted or unsubstituted C$_{1-10}$ hydrocarbon chain, optionally wherein one or more carbon units of the hydrocarbon chain is independently replaced with substituted or unsubstituted phenyl, substituted or unsubstituted triazolyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, substituted or unsubstituted C$_{1-10}$ alkyl, or a nitrogen protecting group, and wherein each occurrence of R$^{Lb}$ is independently selected from the group consisting of hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{Lb}$ groups are joined to form a substituted or unsubstituted carbocyclic or substituted or unsubstituted heterocyclic ring, or R$^{La}$ and R$^{Lb}$ are joined to form a substituted or unsubstituted heterocyclic ring;

each instance of M is independently hydrogen or an agent (e.g., pharmaceutical agent (e.g., therapeutic, diagnostic, or prophylactic agent)); and (b) contacting the polymerization mixture from step (a) with a platinum complex of Formula (I) (e.g., a solution of a platinum complex of Formula (I)).

In certain embodiments, the invention provides Pt-BASPs prepared by Method A including the steps of:

(a) reacting a macromonomer of Formula (III)

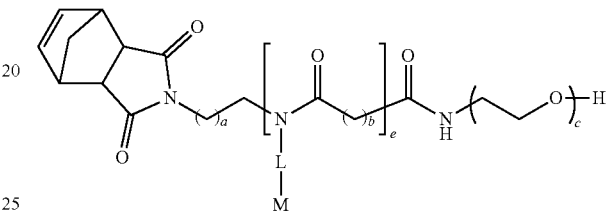

(III)

with a metathesis catalyst to form a polymerization mixture; wherein:

a is an integer from 1 to 10, inclusive;
each instance of b is independently an integer from 1 to 5 inclusive;
c is an integer from 30 to 100 inclusive;
e is 0, 1, 2, 3, or 4;
each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a cleavable linker, or an optionally substituted C$_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, optionally substituted C$_{1-10}$ alkyl, or a nitrogen protecting group, and wherein each occurrence of R$^{Lb}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{Lb}$ groups are joined to form an optionally substituted carbocyclic or optionally substituted heterocyclic ring, or R$^{La}$ and R$^{Lb}$ are joined to form an optionally substituted heterocyclic ring; and each instance of M is independently hydrogen or a pharmaceutical agent (e.g., therapeutic, diagnostic, or prophylactic agent); and (b) contacting the polymerization mixture from step (a) with a platinum complex of Formula (I) (e.g., a solution of a platinum complex of Formula (I)).

In certain embodiments, M in the macromonomer is oxaliplatin or a derivative thereof. In certain embodiments, M in the macromonomer is oxPt-XL. In Method A' (e.g., Method A), step (a) may be performed in the presence of a non-agent-loaded MM, such as a macromonomer of Formula (IV):

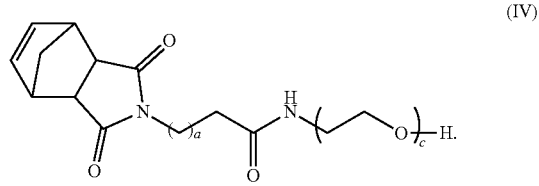

(IV)

In certain embodiments, the molar ratio of a non-agent-loaded MM to the combined agents (including oxPt-XL) is about 0.01:1, about 0.3:1, about 0.67:1, about 1:1, about 1.5:1, about 3:1, about 10:1, about 30:1, or about 100:1, inclusive. In certain embodiments, the molar ratio of a non-agent-loaded macromonomer to the combined agents (including cisplatin) is about 0.67:1, inclusive.

In certain embodiments, the provided Pt-BASPs are prepared by Method B' including the steps of:

(a) reacting a first macromonomer of Formula (III'), or a salt thereof, with a second macromonomer of Formula (III'), or a salt thereof:

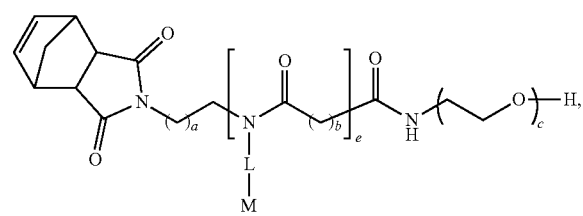

(III')

in the presence of a metathesis catalyst to form a polymerization mixture, wherein a, L, M, b, e, and c are as described herein, provided that M in the first macromonomer is different from M in the second macromonomer; and (b) contacting the polymerization mixture from step (a) with a platinum complex of Formula (I) (e.g., a solution of a platinum complex of Formula (I)).

In certain embodiments, the provided Pt-BASPs are loaded with more than one therapeutic, diagnostic, or prophylactic agents other than oxaliplatin or a derivative thereof and can be prepared by Method B including the steps of:

(a) reacting a first macromonomer of Formula (III) with a second macromonomer of Formula (III)

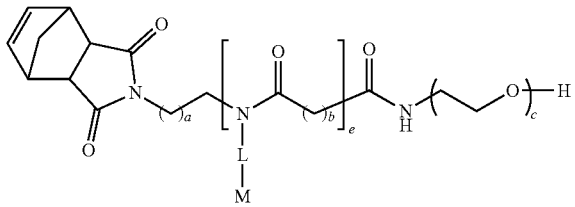

(III)

in the presence of a metathesis catalyst to form a polymerization mixture,
wherein:
a is an integer from 1 to 10, inclusive;
each instance of b is independently an integer from 1 to 5 inclusive;
c is an integer from 1 to 100 inclusive;
e is 0, 1, 2, 3, or 4;
each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a cleavable linker, or an optionally substituted C$_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, optionally substituted C$_{1-10}$ alkyl, or a nitrogen protecting group, and wherein each occurrence of R$^{Lb}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{Lb}$ groups are joined to form an optionally substituted carbocyclic or optionally substituted heterocyclic ring, or R$^{La}$ and R$^{Lb}$ are joined to form an optionally substituted heterocyclic ring; each instance of M is independently hydrogen or a pharmaceutical agent (e.g., therapeutic, diagnostic, or prophylactic agent); and M in the first macromonomer is different from M in the second macromonomer; and (b) contacting the polymerization mixture from step (a) with a platinum complex of Formula (I) (e.g., a solution of a platinum complex of Formula (I)).

In Method B' (e.g., Method B), step (a) may be performed in the presence of a non-agent-loaded MM, such as a macromonomer of Formula (IV):

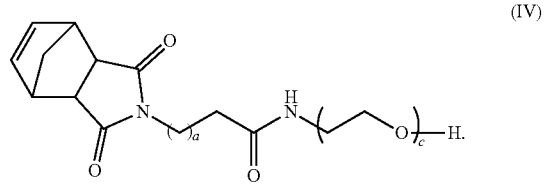

(IV)

In certain embodiments, the non-agent-loaded MM is macromonomer PEG-MM. In certain embodiments of the Pt-BASPs loaded with more than one therapeutic, diagnostic, or prophylactic agents, Ms in the first and second macromonomers are different. In certain embodiments of the Pt-BASPs loaded with more than one therapeutic, diagnostic, or prophylactic agents, Ms in the first and second macromonomers are the same. In certain embodiments of the Pt-BASPs loaded with more than one therapeutic, diagnostic, or prophylactic agents, at one instance of Ms in the first MM and at least one instance of Ms in the second MM are different from each other. In certain embodiments, Ms in the first and second macromonomers are not oxaliplatin or a derivative thereof (e.g., oxPt-XL). In certain embodiments of the Pt-BASPs loaded with more than one therapeutic, diagnostic, or prophylactic agents, Ms in the first and second macromonomers are different therapeutic agents. In certain embodiments, M in the first macromonomer is camptothecin, and M in the second macromonomer is 5-FU. In certain embodiments, M in the first macromonomer is IRT, and M in the second macromonomer is 5-FU. In certain embodiments, M in the first macromonomer is SN-38, and M in the second macromonomer is 5-FU.

As generally defined herein, a is an integer from 1 to 10, inclusive. In certain embodiments, a is 1. In certain embodiments, a is 2. In certain embodiments, a is 3. In certain embodiments, a is 4. In certain embodiments, a is 5. In certain embodiments, a is 6. In certain embodiments, a is 7. In certain embodiments, a is 8. In certain embodiments, a is 9. In certain embodiments, a is 10.

As generally defined herein, each instance of b is independently an integer from 1 to 10, inclusive. In certain embodiments, b is an integer from 1 to 5, inclusive. In certain embodiments, b is 1. In certain embodiments, b is 2. In certain embodiments, b is 3. In certain embodiments, b is 4. In certain embodiments, b is 5. In certain embodiments, b is 6. In certain embodiments, b is 7. In certain embodiments, b is 8. In certain embodiments, b is 9. In certain embodiments, b is 10.

As generally defined herein, c is an integer from 1 to 200, inclusive. In certain embodiments, c is an integer from 1 to 100, inclusive. In certain embodiments, c is an integer from 1 to 29, inclusive. In certain embodiments, c is an integer from 30 to 100, inclusive. In certain embodiments, c is an integer from 40 to 90, inclusive. In certain embodiments, c is an integer from 50 to 80, inclusive. In certain embodiments, c is an integer from 60 to 70, inclusive. In certain embodiments, c is about 65. In certain embodiments, c is about 66. In certain embodiments, c is about 67. In certain embodiments, c is about 68. In certain embodiments, c is about 69. In certain embodiments, c is about 70. In certain embodiments, c is an integer from 101 to 200, inclusive.

As generally defined herein, e is 0, 1, 2, 3, 4, 5, or 6. In certain embodiments, e is 0, 1, 2, 3, or 4. In certain embodiments, e is 0. In certain embodiments, e is 1. In certain embodiments, e is 2. In certain embodiments, e is 3. In certain embodiments, e is 4. In certain embodiments, e is 5. In certain embodiments, e is 6.

As generally defined herein, each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a cleavable linker, a polymer, or a substituted or unsubstituted $C_{1-30}$ hydrocarbon chain, optionally wherein one or more carbon units of the hydrocarbon chain is independently replaced with substituted or unsubstituted phenyl, substituted or unsubstituted triazolyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, substituted or unsubstituted $C_{1-10}$ alkyl, or a nitrogen protecting group, and wherein each occurrence of R$^{Lb}$ is independently selected from the group consisting of hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{Lb}$ groups are joined to form a substituted or unsubstituted carbocyclic or substituted or unsubstituted heterocyclic ring, or R$^{La}$ and R$^{Lb}$ are joined to form a substituted or unsubstituted heterocyclic ring.

In certain embodiments, linker L is —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a cleavable linker, or an optionally substituted $C_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, optionally substituted $C_{1-10}$ alkyl, or a nitrogen protecting group, and wherein each occurrence of R$^{Lb}$ is independently selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, and optionally substituted heteroaryl, or two R$^{Lb}$ groups are joined to form an optionally substituted carbocyclic or optionally substituted heterocyclic ring, or R$^{La}$ and R$^{Lb}$ are joined to form an optionally substituted heterocyclic ring.

In certain embodiments, L is an optionally substituted $C_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—. In certain embodiments, at least one instance of L is a peptide. In certain embodiments, L is a peptide consisting of between 2 and 50, between 2 and 30, between 2 and 20, between 2 and 10, between 2 and 5, between 5 and 50, between 5 and 30, between 5 and 20, between 5 and 10, between 10 and 50, between 10 and 30, between 10 and 20, between 20 and 50, between 20 and 30, or between 30 and 50, inclusive, amino acids (e.g., natural amino acids). In certain embodiments, at least one instance of L is cleavable linker. In certain embodiments, L is a photo-cleavable linker. In certain embodiments, L is not a photo-cleavable linker. In certain embodiments, L is not a photo-cleavable linker. In certain embodiments, L is a linker cleavable by hydrolysis (e.g., under physiological conditions). In certain embodiments, L is a linker cleavable by reduction. In certain embodiments, at least one instance of L is a polymer (e.g., a polymer whose $M_w$ is between 2,000 and 1,000,000, g/mol, inclusive).

In certain embodiments, at least one instance of L is a substituted or unsubstituted $C_{1-30}$ hydrocarbon chain (e.g., substituted or unsubstituted $C_{6-20}$ hydrocarbon chain), wherein one or more (e.g., two, three, four, five, or six) carbon units of the hydrocarbon chain is independently replaced with substituted or unsubstituted phenyl, substituted or unsubstituted triazolyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—.

In certain embodiments, at least one instance of L is a substituted or unsubstituted $C_{1-30}$ hydrocarbon chain (e.g., substituted or unsubstituted $C_{6-20}$ hydrocarbon chain), wherein:

one or more (e.g., two) carbon units of the hydrocarbon chain is replaced with substituted or unsubstituted triazolyl (e.g.,

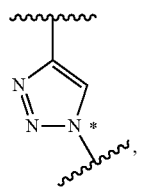 [SMILES: *c1cn(*)nn1]

wherein the nitrogen atom labelled with "*" is attached (e.g., directly or indirectly) to M); and optionally one or more (e.g., two, three, four, or five) carbon units of the hydrocarbon chain is independently replaced with substituted or unsubstituted phenyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—.

In certain embodiments, at least one instance of L is a substituted or unsubstituted $C_{1-30}$ hydrocarbon chain (e.g., substituted or unsubstituted $C_{6-20}$ hydrocarbon chain), wherein:

one or more (e.g., two) carbon units of the hydrocarbon chain is replaced with substituted or unsubstituted triazolyl (e.g.,

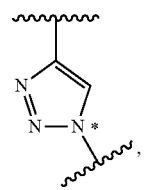 [SMILES: *c1cn(*)nn1]

wherein the nitrogen atom labelled with "*" is attached (e.g., directly or indirectly) to M);

one or more (e.g., two) carbon units of the hydrocarbon chain is replaced with substituted or unsubstituted phenyl; and optionally one or more (e.g., two, three, or four) carbon units of the hydrocarbon chain is independently replaced with —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—.

In certain embodiments, when at least one instance of L is a substituted $C_{1-30}$ hydrocarbon chain (e.g., substituted $C_{1-10}$ hydrocarbon chain), optionally wherein one or more carbon units of the hydrocarbon chain is independently replaced as described herein, the substituents on the $C_{1-30}$ hydrocarbon chain (e.g., $C_{1-10}$ hydrocarbon chain) are independently halogen or substituted or unsubstituted $C_{1-6}$ alkyl. In certain embodiments, when at least one instance of L is a substituted $C_{1-30}$ hydrocarbon chain (e.g., substituted $C_{1-10}$ hydrocarbon chain), optionally wherein one or more carbon units of the hydrocarbon chain is independently replaced as described herein, the substituents on the $C_{1-30}$ hydrocarbon chain (e.g., $C_{1-10}$ hydrocarbon chain) are independently halogen or unsubstituted $C_{1-6}$ alkyl.

In certain embodiments, L is of one of the following formulae:

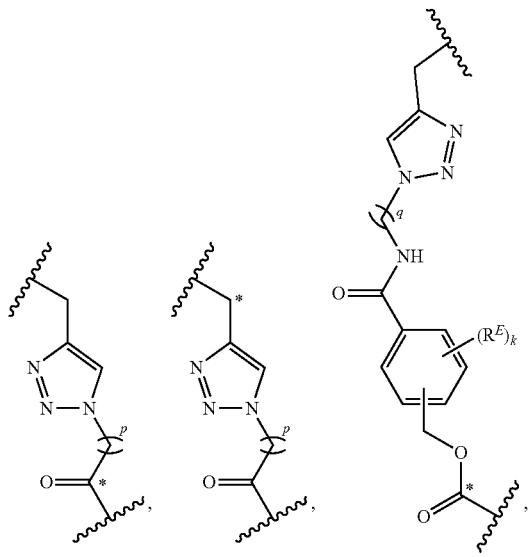

-continued

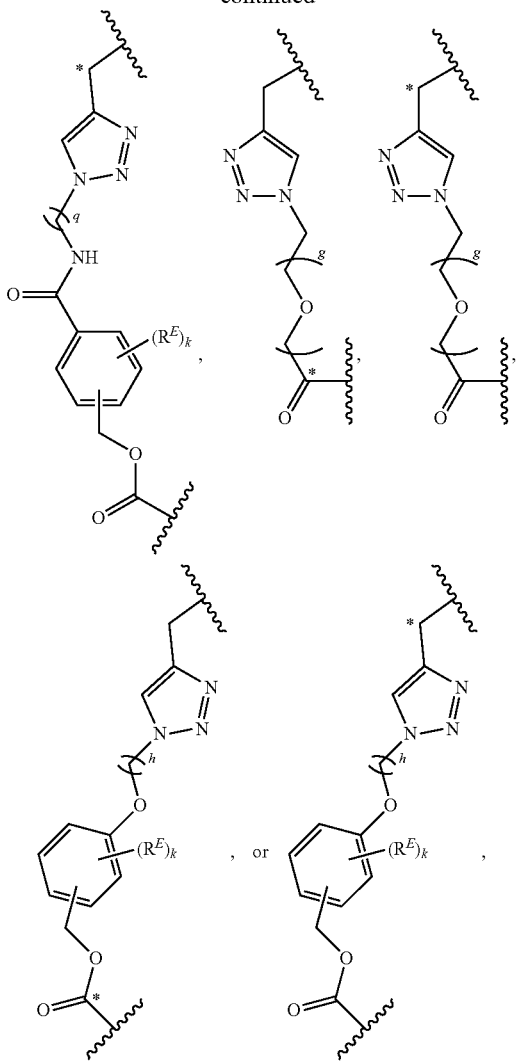

wherein:

each instance of the carbon atom labeled with "*" is attached to M;

each instance of $R^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C($=NR^a$)$R^a$, —C($=NR^a$)$OR^a$, —C($=NR^a$)N($R^a$)$_2$, —C($=O$)$R^a$, —C($=O$)$OR^a$, —C($=O$)$N(R^a)_2$, —$NO_2$, —$N(R^a)C(=O)R^a$, —$N(R^a)C(=O)OR^a$, —$N(R^a)C(=O)N(R^a)_2$, —$N(R^a)S(=O)R^a$, —$N(R^a)S(=O)OR^a$, —$N(R^a)S(=O)N(R^a)_2$, —$N(R^a)S(=O)_2R^a$, —$N(R^a)S(=O)_2OR^a$, —$N(R^a)S(=O)_2N(R^a)_2$, —$OC(=O)R^a$, —$OC(=O)OR^a$, or —$OC(=O)N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring;

each instance of k is independently 0, 1, 2, 3, or 4;

each instance of p is independently an integer from 1 to 10, inclusive;

each instance of q is independently an integer from 1 to 10, inclusive;

each instance of g is independently an integer from 1 to 10, inclusive; and each instance of h is independently an integer from 1 to 10, inclusive.

In certain embodiments, each instance of L is the same. In certain embodiments, at least two instances of L are different from each other.

In certain embodiments, the macromonomer of Formula (III) is of Formula (III-a):

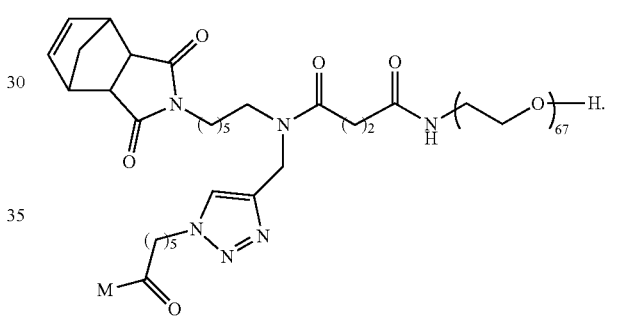

(III-a)

In certain embodiments, the macromonomer of Formula (III) is of Formula (III-b):

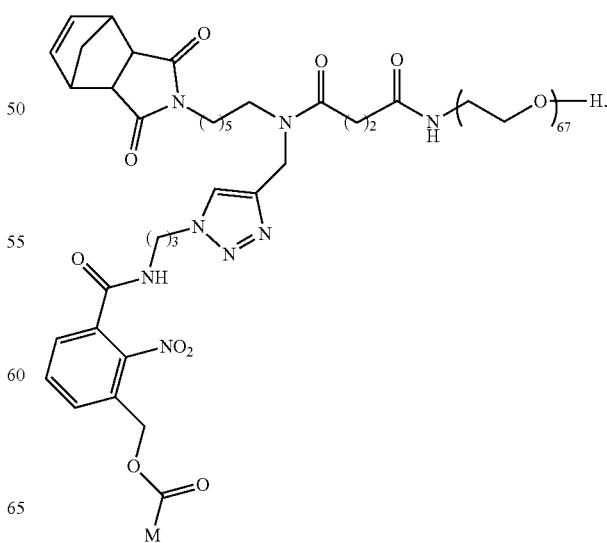

(III-b)

In certain embodiments, the macromonomer of Formula (III) is of Formula (III-c):
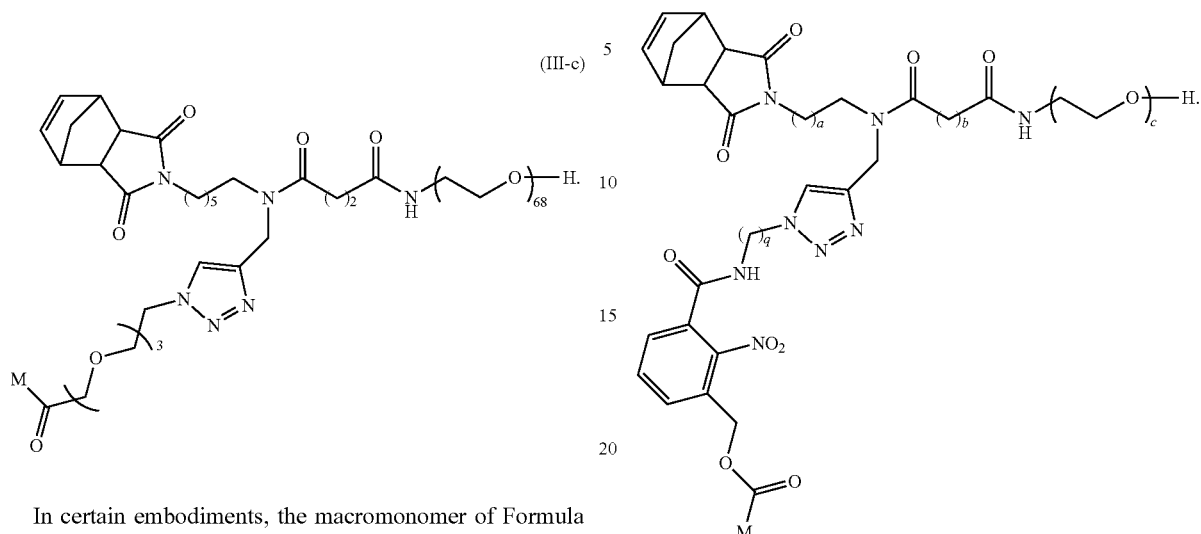
In certain embodiments, the macromonomer of Formula (III) is of Formula (III-d):
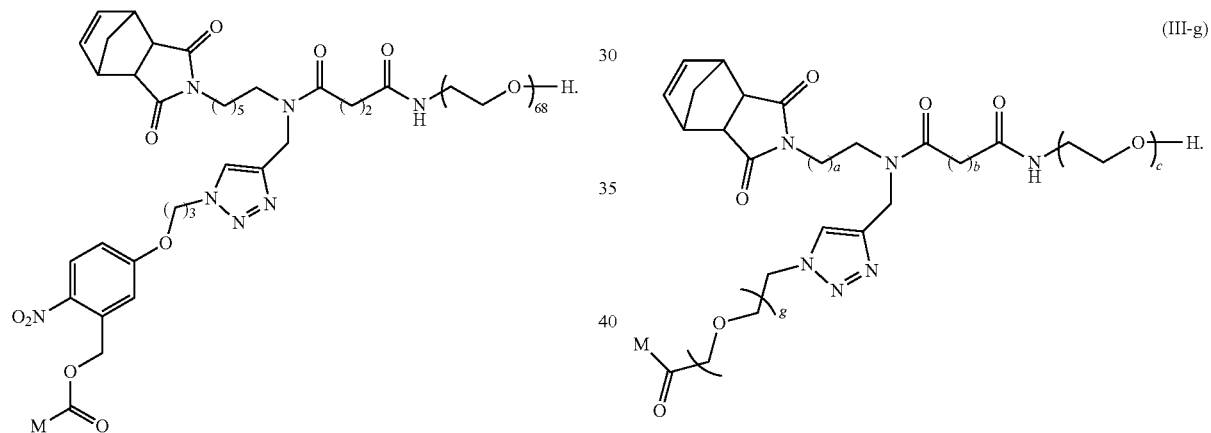
In certain embodiments, the macromonomer of Formula (III) is of Formula (III-e):
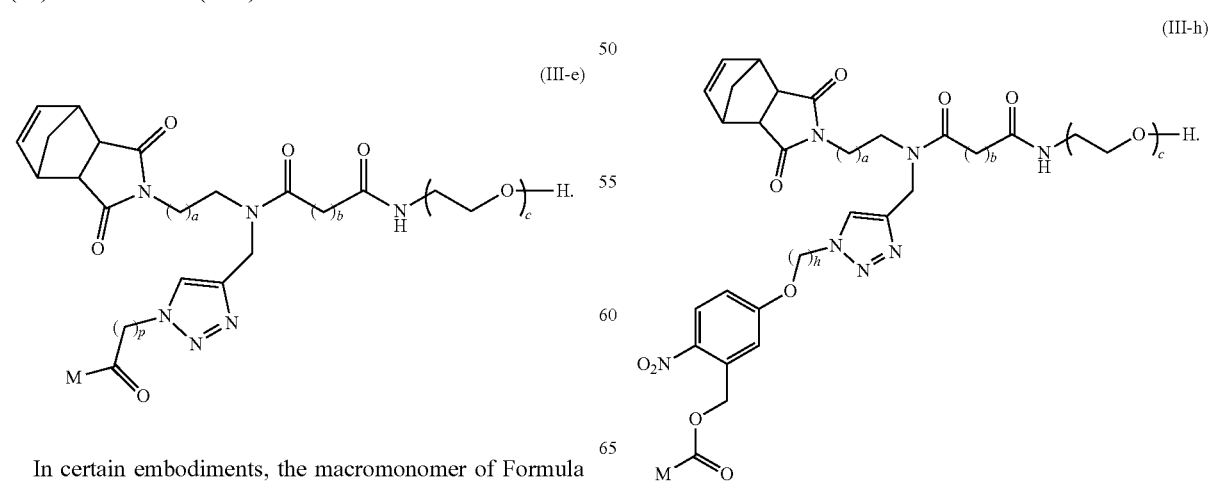
In certain embodiments, the macromonomer of Formula (III) is of Formula (III-f):

As generally defined herein, each instance of M is independently hydrogen or an agent. In certain embodiments, the agent is a small molecule (optionally wherein the molecular weight of the small molecule is not more than 2,000 g/mol). In certain embodiments, the agent is a protein or peptide. In certain embodiments, the agent is a polynucleotide. In certain embodiments, each instance of M is independently hydrogen or a pharmaceutical agent. In certain embodiments, M is hydrogen or a therapeutic, diagnostic, or prophylactic agent. In certain embodiments, M is hydrogen. In certain embodiments, M is not hydrogen. In certain embodiments, at least one instance of M is a pharmaceutical agent. In certain embodiments, M is a therapeutic, diagnostic, or prophylactic agent. In certain embodiments, M is a therapeutic agent. Examples of therapeutic moieties include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, parasympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic moieties include contraceptives and vitamins as well as micro- and macronutrients. Still other examples include antiinfectives such as antibiotics and antiviral agents; analgesics and analgesic combinations; anorexics; antiheimintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins. In certain embodiments, at least one instance of M is an anti-cancer agent. In certain embodiments, M is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkyl-sulphonates (e.g., busulfan and treosulfan), triazenes (e.g., dacarbazine, temozolomide), platinum containing compounds (e.g., cisplatin, carboplatin, oxaliplatin), *vinca* alkaloids (e.g., vincristine, vinblastine, vindesine, and vinorelbine), taxoids (e.g., paclitaxel or a paclitaxel equivalent) docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g. hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (Astra- Zeneca), BEZ235 (Novartis), BGT226 (Norvartis), XL765 (Sanofi Aventis), PF-4691502 (Pfizer), GDC0980 (Genetech), SF1126 (Semafoe), and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, at least one instance of M is camptothecin. In certain embodiments, at least one instance of M is IRT. In certain embodiments, at least one instance of M is SN-38. In certain embodiments, at least one instance of M is 5-FU. In certain embodiments, at least two instances of M are camptothecin and 5-FU. In certain embodiments, at least two instances of M are IRT and 5-FU. In certain embodiments, at least two instances M are SN-38 and 5-FU. In certain embodiments, at least three instances of M are IRT, 5-FU, and oxaliplatin or a derivative thereof. In certain embodiments, at least three instances of M are CPT, 5-FU, and oxaliplatin or a derivative thereof. In certain embodiments, at least three instances of M are SN-38, 5-FU, and oxaliplatin or a derivative thereof.

In certain embodiments, M is a diagnostic agent. Exemplary diagnostic agents include, but are not limited to, fluorescent molecules; gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, M is a prophylactic agent. Prophylactic agents that can be included in the conjugates of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, each instance of M is the same. In certain embodiments, at least two instances of M are different from each other. In certain embodiments, at least three instances of M are different from each other. In certain embodiments, at least four instances of M are different from each other.

M can be conjugated to the macromonomer using any suitable conjugation technique. For instance, EDC-NHS chemistry (1-ethyl-3-(3-dimethylaminopropyl) carbodiimide hydrochloride and N-hydroxysuccinimide), or a reaction involving a maleimide or a carboxylic acid, which can be conjugated to one end of a thiol, an amine, or a similarly functionalized polyether. The conjugation can be performed in an organic solvent, such as, but not limited to, methylene chloride, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting the agent that includes a hydroxyl, thiol, or amino group with a polymer comprising a carboxylic acid functional group. Such a reaction may occur as a single-step reaction, i.e., the conjugation is performed with or without using intermediates such as N-hydroxysuccinimide or a maleimide. The conjugation reaction between the amine-containing, thiol-containing, or hydroxyl-containing moiety and the carboxylic acid-terminated polymer may be achieved in one embodiment, by adding the amine-containing, thiol-containing, or hydroxyl-containing moiety, solubilized in an organic solvent such as, but not limited to, dichloromethane, acetonitrile, chloroform, tetrahydrofuran, acetone, formamide, dimethylformamide, pyridines, dioxane, or dimethysulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously in some cases. Unconjugated macromonomers may be washed away after such reactions, and the polymer may be precipitated in solvents such as, for instance, ethyl ether, hexane, methanol, or ethanol.

The synthesis of Pt-BASPs involves ROMP of MM in step (a) and ROMP of the platinum complex in step (b). In certain embodiments, the ROMP catalyst is a tungsten (W), molybdenum (Mo), or ruthenium (Ru) catalyst. In certain embodiments, the ROMP catalyst is a ruthenuim catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the ROMP catalyst is a Grubbs catalyst. In certain embodiments, the Grubbs catalyst is selected from the group consisting of:

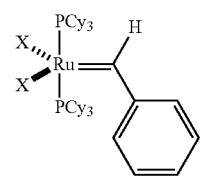

X = Cl; Br; I
Cy = cyclohexyl

Benzylidenebis-(tricyclohexylphosphine)-dichlororuthenium (X=Cl);

Benzylidenebis-(tricyclohexylphosphine)-dibromoruthenium (X=Br);

Benzylidenebis-(tricyclohexylphosphine)-diiodoruthenium (X=I);

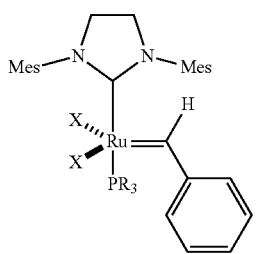

X = Cl; Br; I
R = cyclohexyl (Cy); phenyl (Ph); benzyl (Bn)

1,3-(Bis(mesityl)-2-imidazolidinylidene)dichloro-(phenyl-methylene) (tricyclohexyl-phosphine)ruthenium (X=Cl; R=cyclohexyl);

1,3-(Bis(mesityl)-2-imidazolidinylidene)dibromo-(phenyl-methylene) (tricyclohexyl-phosphine)ruthenium (X=Br; R=cyclohexyl);

1,3-(Bis(mesityl)-2-imidazolidinylidene)diiodo-(phenylm-ethylene) (tricyclohexyl-phosphine)ruthenium (X=I; R=cyclohexyl);

1,3-(Bis(mesityl)-2-imidazolidinylidene)dichloro-(phenyl-methylene) (triphenylphosphine)ruthenium (X=Cl; R=phenyl);

1,3-(Bis(mesityl)-2-imidazolidinylidene)dichloro-(phenyl-methylene) (tribenzylphosphine)ruthenium (X=Cl; R=benzyl);

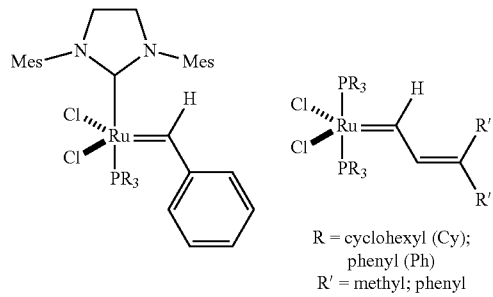

R = cyclohexyl (Cy); phenyl (Ph)
R' = methyl; phenyl

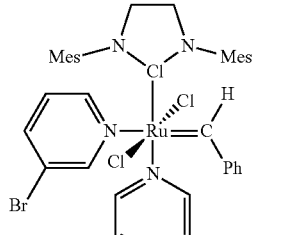

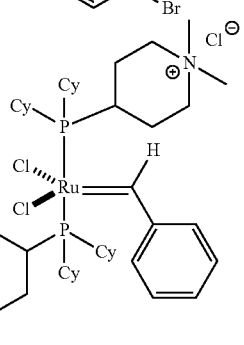

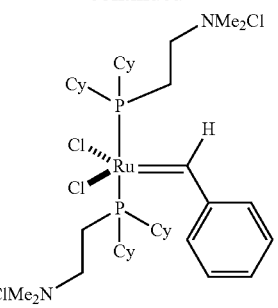

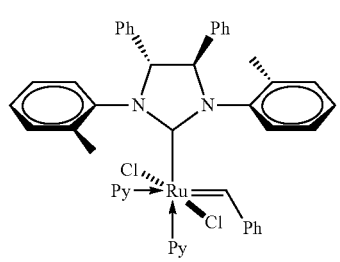

Py = pyridine
Ph = phenyl

In certain embodiments, the ROMP catalyst is a Grubbs-Hoveyda catalyst. In certain embodiments, the Grubbs-Hoveyda catalyst is selected from the group consisting of:

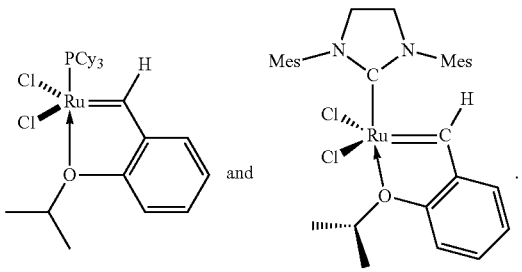

and

In certain embodiments, the ROMP catalyst is selected from the group consisting of:

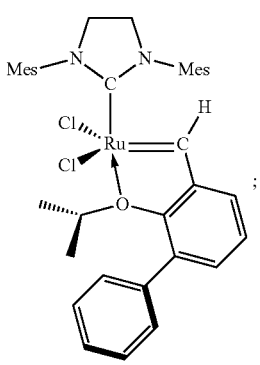

Blechart Catalyst

-continued

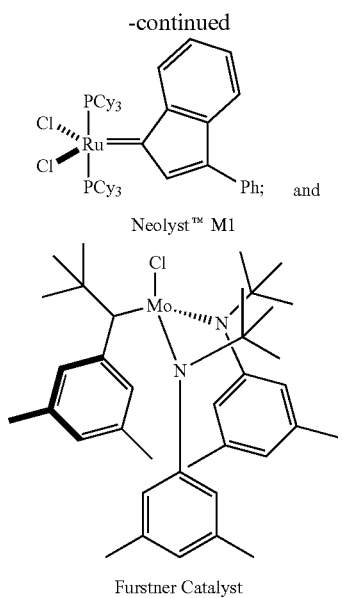

Neolyst™ M1

Furstner Catalyst

In certain embodiments, the ROMP catalyst is of the formula:

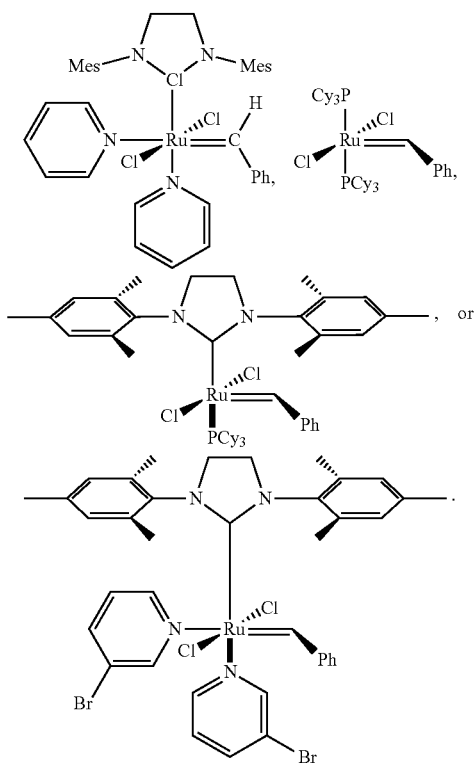

The ROMP can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

The ROMP can be quenched with a vinyl ether of the formula

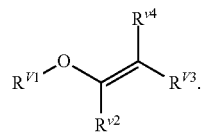

Each of $R^{v1}$, $R^{v2}$, $R^{v3}$, and $R^{v4}$ is independently optionally substituted alkyl, optionally substituted alkenyl, optionally substituted alkynyl, optionally substituted carbocyclyl, optionally substituted phenyl, optionally substituted heterocyclyl, or optionally substituted heteroaryl. In certain embodiments, $R^{v1}$ is optionally substituted alkyl, and $R^{v2}$, $R^{v3}$, and $R^{v4}$ are hydrogen. In certain embodiments, $R^{v1}$ is unsubstituted alkyl, and $R^{v2}$, $R^{v3}$, and $R^{v4}$ are hydrogen. In certain embodiments, $R^{v1}$ is substituted alkyl, and $R^{v2}$, $R^{v3}$, and $R^{v4}$ are hydrogen. In certain embodiments, $R^{v1}$ is methyl, and $R^{v2}$, $R^{v3}$, and $R^{v4}$ are hydrogen. In certain embodiments, $R^{v1}$ is ethyl, and $R^{v2}$, $R^{v3}$, and $R^{v4}$ are hydrogen. In certain embodiments, $R^{v1}$ is propyl, and $R^{v2}$, $R^{v3}$, and $R^{v4}$ are hydrogen. In certain embodiments, $R^{v1}$ is optionally substituted alkenyl, and $R^{v2}$, $R^{v3}$, and $R^{v4}$ are hydrogen. In certain embodiments, $R^{v1}$ is unsubstituted alkenyl, and $R^{v2}$, $R^{v3}$, and $R^{v4}$ are hydrogen. In certain embodiments, $R^{v1}$ is vinyl, and $R^{v2}$, $R^{v3}$, and $R^{v4}$ are hydrogen. In certain embodiments, at least one of $R^{v1}$, $R^{v2}$, $R^{v3}$, and $R^{v4}$ is conjugated with a diagnostic agent as defined above. In certain embodiments, the ROMP is quenched by ethyl vinyl ether. Excess ethyl vinyl ether can be removed from the Pt-BASPs by vacuum.

The Pt-BASPs can be multi-agent loaded star polymers. In certain embodiments, the inventive Pt-BASPs are capable of releasing multiple chemotherapeutic agents for combination therapy. In certain embodiments, the Pt-BASPs are capable of releasing two chemotherapeutic agents. In certain embodiments, the Pt-BASPs are capable of releasing three chemotherapeutic agents. In certain embodiments, the Pt-BASPs are capable of releasing four chemotherapeutic agents. In certain embodiments, the Pt-BASPs are capable of releasing five chemotherapeutic agents. In certain embodiments, the Pt-BASPs incorporate only a platinum-based agent which is introduced from the platinum-based complex crosslinkers. In certain embodiments, the inventive Pt-BASPs incorporate only cisplatin. In certain embodiments, the Pt-BASPs incorporate one or more therapeutic, diagnostic, or prophylactic agents. The one or more therapeutic, diagnostic, or prophylactic agents are introduced from macromonomers in the synthesis of Pt-BASPs. In certain embodiments, a therapeutic agent is incorporated in the macromonomer. In certain embodiments, an anti-cancer agent is incorporated in the macromonomer. In certain embodiments, the macromonomer is camptothecin (CPT) macromonomer. In certain embodiments, the macromonomer is IRT macromonomer. In certain embodiments, the macromonomer is 5-FU macromonomer. In certain embodiments, the macromonomer is SN-38 macromonomer. In certain embodiments, the macromonomer is doxorubicin (DOX) macromonomer. In certain embodiments, the inventive Pt-BASPs incorporate oxaliplatin or a derivative thereof and CPT. In certain embodiments, the inventive Pt-BASPs incorporate oxaliplatin or a derivative thereof and IRT. In certain embodiments, the inventive Pt-BASPs incorporate oxaliplatin or a derivative thereof and 5-FU. In certain embodiments, the inventive Pt-BASPs incorporate an oxaliplatin prodrug, CPT, and 5-FU. In certain embodiments, the inventive Pt-BASPs incorporate an oxaliplatin prodrug, IRT, and 5-FU. In certain embodiments, the inventive Pt-BASPs incorporate an oxaliplatin prodrug, SN-38, and 5-FU. In certain embodiments, the one or more therapeutic, diagnostic, or prophylactic agents are connected to Pt-BASPs by a photocleavable linker. In certain embodiments, the inventive Pt-BASPs incorporate a diagnostic agent and a platinum therapeutic agent. In certain embodiments, the inventive Pt-BASPs incorporate a prophylactic agent and a platinum therapeutic agent.

In some cases, the Pt-BASPs are of the form of nanoparticles, i.e., the particle have a characteristic dimension of less than about 1 micrometer, where the characteristic dimension of a particle is the diameter of a perfect sphere having the same volume as the particle. In certain embodiments, the Pt-BASP particle has a characteristic dimension of less than about 300 nm. In certain embodiments, the Pt-BASP particle has a characteristic dimension of less than about 200 nm. In certain embodiments, the Pt-BASP particle has a characteristic dimension of less than about 150 nm. In certain embodiments, the Pt-BASP particle has a characteristic dimension of less than about 100 nm. In certain embodiments, the Pt-BASP particle has a characteristic dimension of less than about 50 nm. In certain embodiments, the Pt-BASP particle has a characteristic dimension of less than about 30 nm. In certain embodiments, the Pt-BASP particle has a characteristic dimension of less than about 20 nm. In certain embodiments, the Pt-BASP particle has a characteristic dimension of less than about 10 nm. In certain embodiments, the Pt-BASP particle has a characteristic dimension between 6 and 250 nm, inclusive. In certain embodiments, the Pt-BASP particle has a characteristic dimension between 8 and 200 nm, inclusive. In certain embodiments, the Pt-BASP particle has a characteristic dimension between 12 and 200 nm, inclusive. In certain embodiments, the Pt-BASP particle has a characteristic dimension between 50 and 200 nm, inclusive.

In certain embodiments, the Pt-BASPs are biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In certain embodiments, the solvents in step (a) is the same as the solvent of the platinum complex solution in step (b). In certain embodiments, the solvents in step (a) is different from the solvent of the platinum complex solution in step (b). Exemplary solvents for step (a) and platinum complex solution include, but are not limited to, methylene chloride, acetonitrile, chloroform, dimethylformamide, tetrahydrofuran, and acetone. Specific reaction conditions can be determined by those of ordinary skill in the art using no more than routine experimentation.

In certain embodiments of one type of macromonomer in Pt-BASPs, the amount of all the macromonomers, the platinum complex crosslinker, and the metathesis catalyst is of the molar ratio m:N:1, wherein m is an integer from 1 to 20, inclusive; and N is an integer from 1 to 20, inclusive. In certain embodiments, m is an integer from 3 to 12 inclusive. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10. In certain embodiments, m is 11. In certain embodiments, m is 12. In certain embodiments, N is an integer from 1 to 10 inclusive. In certain embodiments, N is 1. In certain embodiments, N is 2. In certain embodiments, N is 3. In certain embodiments, N is 4. In certain embodiments, N is 5. In certain embodiments, N is 6. In certain embodiments, N is 7. In certain embodiments, N is 8. In certain embodiments, N is 9. In certain embodiments, N is 10. In certain embodiments, the amount of macromonomer, platinum complex crosslinker, and metathesis catalyst is of the ratio 5:3:1. In certain embodiments, the amount of macromonomer, platinum complex crosslinker, and metathesis catalyst is of the molar ratio 5:5:1. In certain embodiments, the amount of macromonomer, platinum complex crosslinker, and metathesis catalyst is of the molar ratio 5:7:1. In certain embodiments, the amount of macromonomer, platinum complex crosslinker, and metathesis catalyst is of the molar ratio 7:3:1. In certain embodiments, the amount of macromonomer, platinum complex crosslinker, and metathesis catalyst is of the molar ratio 7:5:1. In certain embodiments, the amount of macromonomer, platinum complex crosslinker, and metathesis catalyst is of the molar ratio 7:7:1. In certain embodiments, the amount of macromonomer, platinum complex crosslinker, and metathesis catalyst is of the molar ratio 11:1:1. In certain embodiments, the amount of macromonomer, platinum complex crosslinker, and metathesis catalyst is of the molar ratio 11:3:1. In certain embodiments, the amount of macromonomer, platinum complex crosslinker, and metathesis catalyst is of the molar ratio 11:5:1.

In certain embodiments, the molar ratio of the first macromonomer to the metathesis catalyst is between 1:1 to 20:1, inclusive; the molar ratio of the second macromonomer to the metathesis catalyst is between 1:1 to 20:1, inclusive; and the molar ratio of the platinum complex to the metathesis catalyst is between 1:1 to 20:1, inclusive. In certain embodiments, the molar ratio of the first macromonomer to the metathesis catalyst is between 1:1 to 10:1, inclusive; the molar ratio of the second macromonomer to the metathesis catalyst is between 1:1 to 10:1, inclusive; and the molar ratio of the platinum complex to the metathesis catalyst is between 1:1 to 10:1, inclusive. In certain embodiments, the molar ratio of the first macromonomer to the metathesis catalyst is between 1:1 to 5:1, inclusive; the molar ratio of the second macromonomer to the metathesis catalyst is between 1:1 to 5:1, inclusive; and the molar ratio of the platinum complex to the metathesis catalyst is between 1:1 to 5:1, inclusive.

In certain embodiments of multi-agent loaded Pt-BASPs, the amount of the first macromonomer, second macromonomer, and platinum complex crosslinker is of the molar ratio of m1:m2:N, wherein m1 and m2 are each independently an integer from 1 to 20, inclusive; and N is an integer from 1 to 20, inclusive. In certain embodiments, the amount of the first macromonomer, second macromonomer, and platinum complex crosslinker is of the molar ratio of 3:4:3. In certain embodiments, the amount of the first macromonomer, second macromonomer, and platinum complex crosslinker is of the molar ratio of 4:3:3. In certain embodiments of more than one types of macromonomers in the multi-agent loaded Pt-BASPs, the amount of the first macromonomer, second macromonomer, and platinum complex crosslinker is of the molar ratio of m1:m2:N:1, wherein m1 and m2 are each independently an integer from 1 to 20, inclusive; and N is an integer from 1 to 20, inclusive. In certain embodiments, the amount of the first macromonomer, second macromonomer, and platinum complex crosslinker is of the molar ratio of 3:4:3:1. In certain embodiments, the amount of the first macromonomer, second macromonomer, and platinum complex crosslinker is of the molar ratio of 4:3:3:1.

Figure 1:
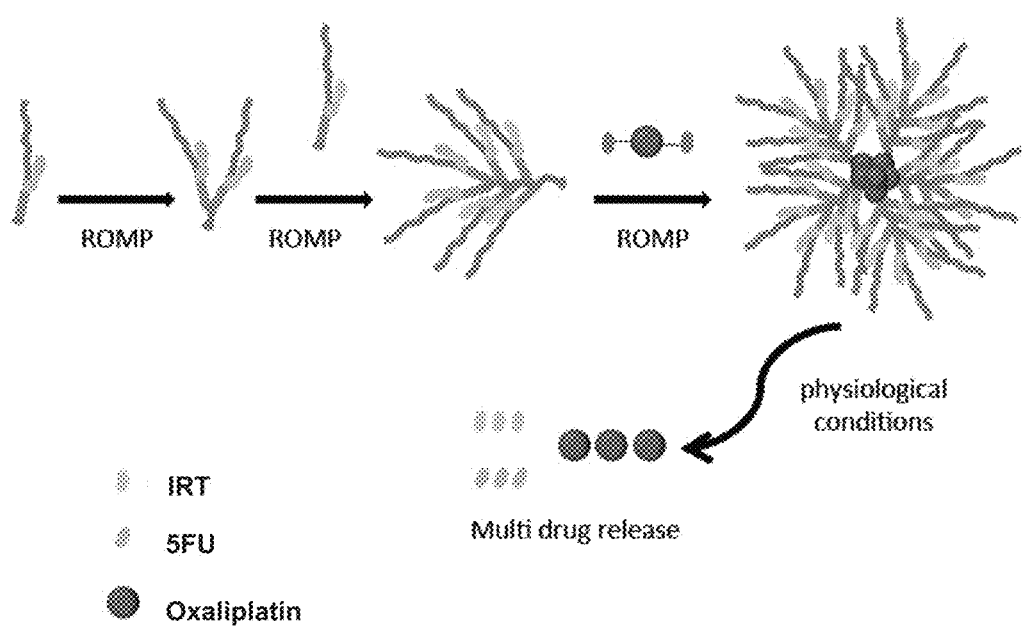
FIG. 1 shows an exemplary synthesis of Pt-BASPs loaded with an oxaliplatin prodrug crosslinker oxPt-XL, irinotecan (IRT), and 5-fluorouracil (5FU).
Figure 2:
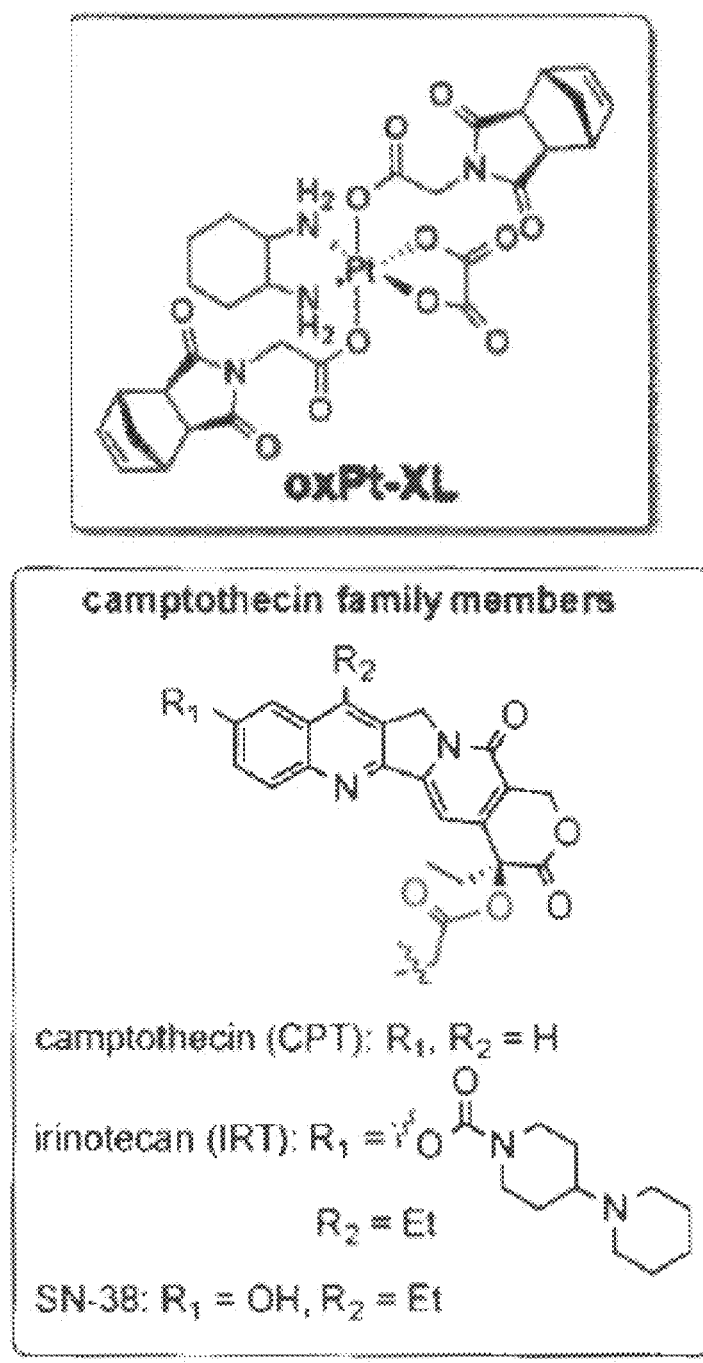
FIG. 2 shows structures of exemplary therapeutic agents: oxPt-XL, camptothecin (CPT), irinotecan (IRT), and SN-38.
Figure 3:
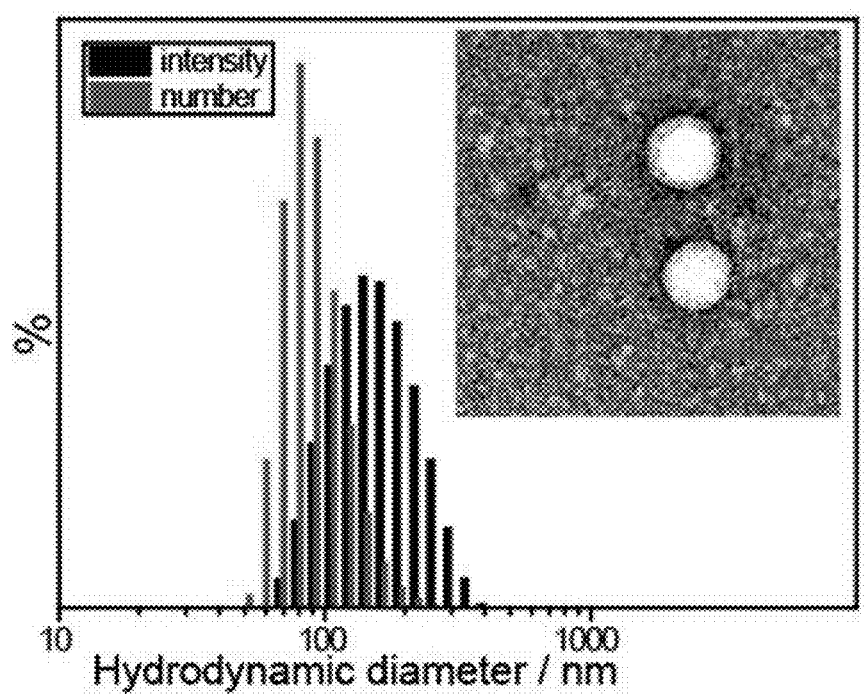
FIG. 3 shows Dynamic Light Scattering (DLS) data and a negatively stained Transmission Electron Microscopy (TEM) image of a BASP prepared from oxPt-XL and PEG-MM.
Figure 4:
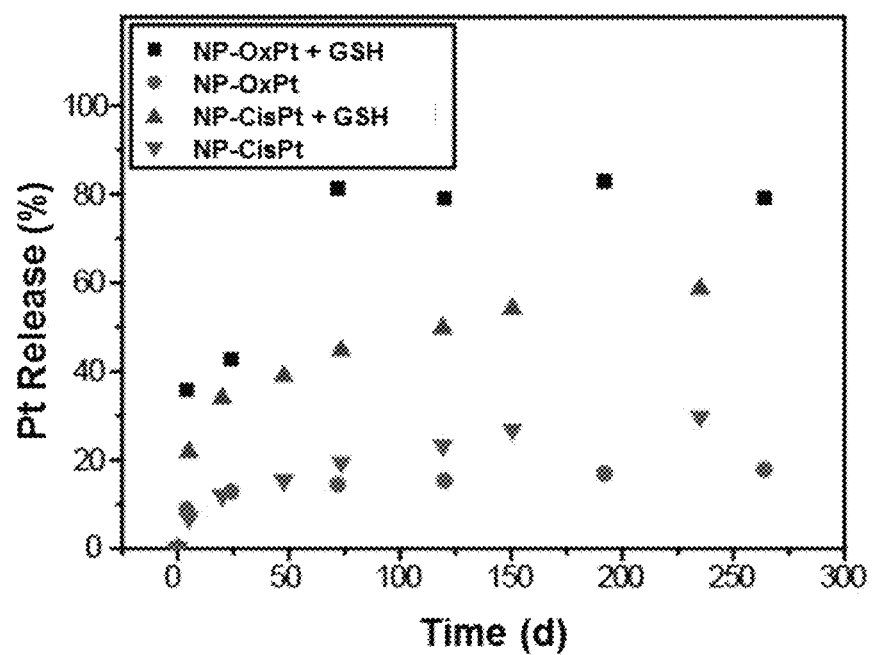
FIG. 4 shows release of cisplatin and oxaliplatin from BASPs in the absence and presence of intracellular concentration (about 5 mM) of glutathione (GSH) reducing agent.
Figure 5:
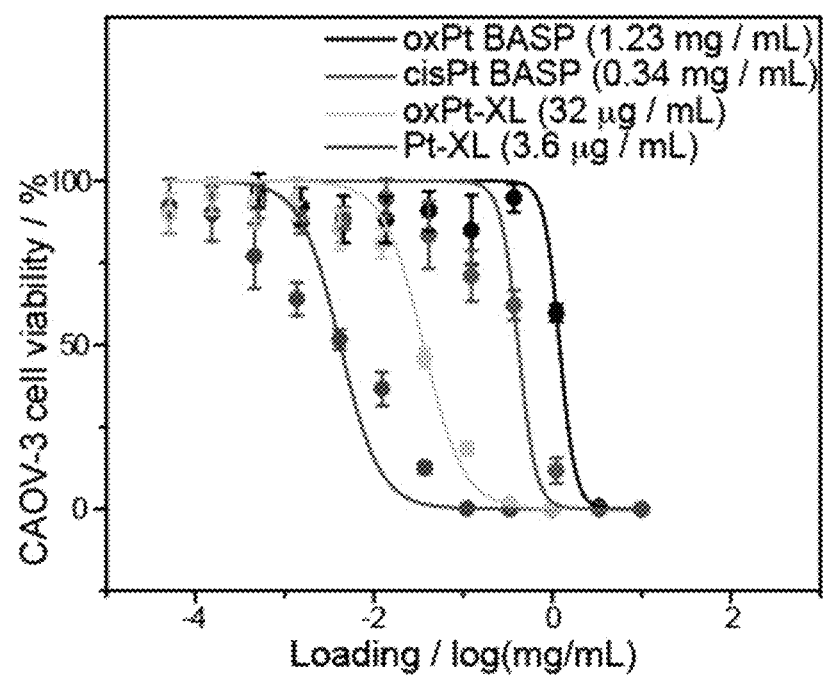
FIG. 5 shows CAOV3 cell viability studies in the presence of cisplatin and oxaliplatin crosslinkers and BASPs.
Figure 6:
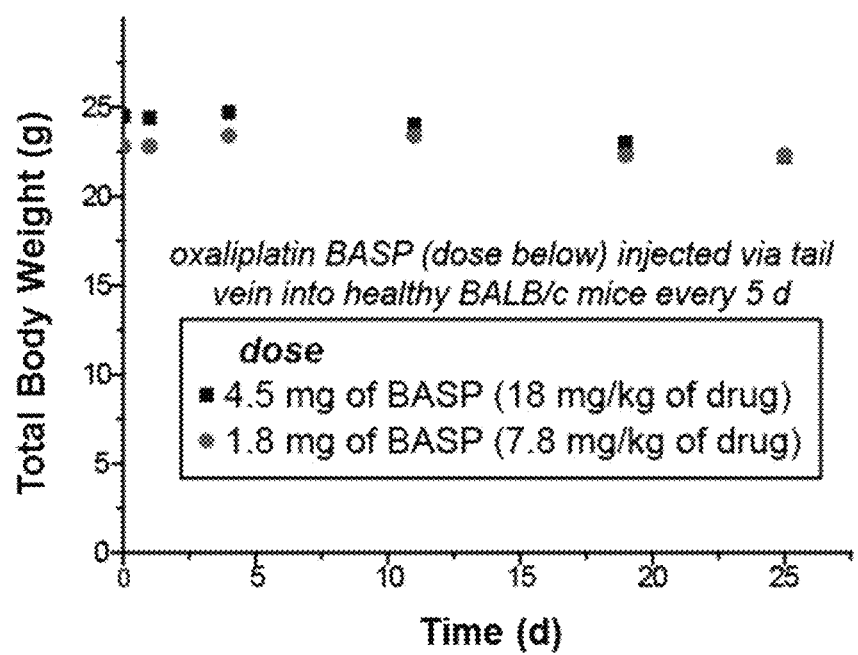
FIG. 6 shows total mouse body weight after injection of two different doses, 4.5 mg and 1.8 mg, of oxaliplatin BASP every 5 days for 25 days.
Figure 7:
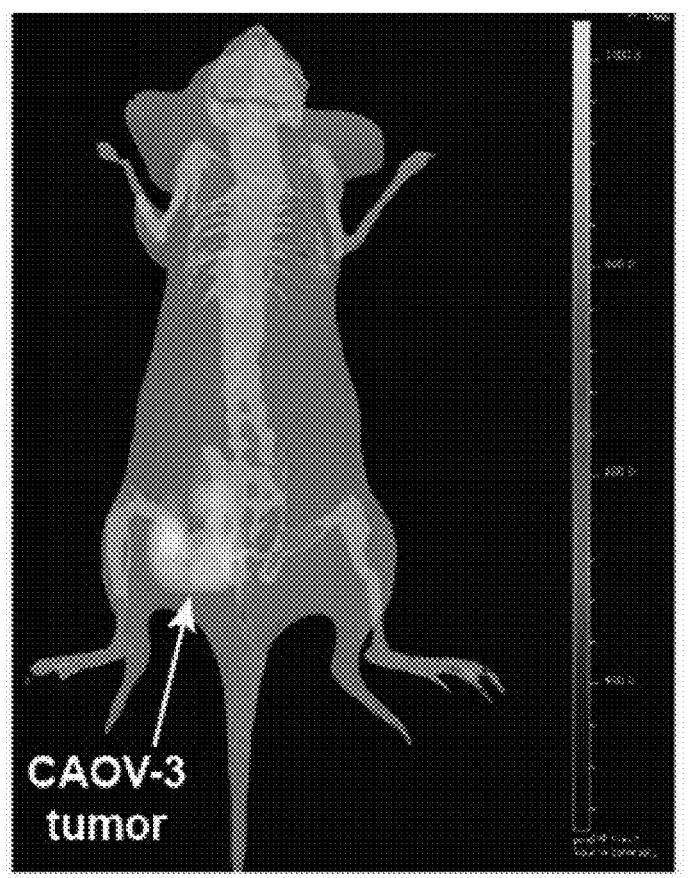
FIG. 7 shows passive tumor acculmulation of Cy5.5-labeled oxaliplatin BASP.

Exposure to physiologically relevant conditions can lead to the Pt-BASPs degradation and controlled, extended release of platinum-based agents. In certain embodiments, the release rate can increased by addition of GSH. In vitro cytotoxicity assays demonstrates that Pt-BASPs effectively kill cancer cells (FIG. 5).

Pharmaceutical Compositions, Kits, and Administration

The present invention provides pharmaceutical compositions comprising Pt-BASPs, as described herein, and optionally a pharmaceutically acceptable excipient. In certain embodiments, the Pt-BASPs are provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the Pt-BASPs into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80)), polyoxyethylene esters (e.g., polyoxyethylene monostearate (MYRJ 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (BRIJ 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC F-68, Poloxamer-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS, PHENONIP, methylparaben, GERMALL 115, GERMABEN II, NEOLONE, KATHON, and EUXYL.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

Dosage forms for topical and/or transdermal administration of a compound of this invention may include ointments, pastes, creams, lotions, gels, powders, solutions, sprays, inhalants and/or patches. Generally, the Pt-BASPs are admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles of Pt-BASPs described herein. Such compositions are conveniently in the form of dry powders for administration using a device comprising a dry powder reservoir to which a stream of propellant can be directed to disperse the powder and/or using a self-propelling solvent/powder dispensing container.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the Pt-BASPs in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the Pt-BASPs and having an average particle from about 0.2 to 500 micrometers. Such a formulation is administered by rapid inhalation through the nasal passage from a container of the powder held close to the nares.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Pt-BASPs provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The Pt-BASPs and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of the inventive polymer for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the inventive polymer may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for treating a proliferative disease (e.g., cancer (e.g., leukemia, melanoma, multiple myeloma), benign neoplasm, angiogenesis, inflammatory disease, autoinflammatory disease, or autoimmune disease). The kits provided may comprise the Pt-BASPs described herein, or a pharmaceutical composition thereof, and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Treatment and Uses

The present invention also provides methods of using the Pt-BASPs described herein, or a pharmaceutical composition thereof, for the treatment or prevention of a proliferative disease such as cancer (e.g., lung cancer, large bowel cancer, pancreas cancer, biliary tract cancer, colorectal cancer, or endometrial cancer), benign neoplasm, angiogenesis, inflammatory disease, autoinflammatory disease, or autoimmune disease in a subject.

In some embodiments, the Pt-BASPs described herein, or a pharmaceutical composition thereof are useful in treating a cancer. In some embodiments, the Pt-BASPs described herein, or a pharmaceutical composition thereof, are useful to delay the onset of, slow the progression of, or ameliorate the symptoms of cancer. In some embodiments, the Pt-BASPs described herein, or a pharmaceutical composition thereof, are administered in combination with other compounds, drugs, or therapeutics to treat cancer.

In some embodiments, the Pt-BASPs described herein, or a pharmaceutical composition thereof are useful for treating a cancer including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrim's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomal-leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM), a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In some embodiments, the Pt-BASPs described herein, or a pharmaceutical composition thereof, are useful in treating lung cancer, head-and-neck cancer, esophagus cancer, stomach cancer, breast cancer, pancreas cancer, colorectal cancer, liver cancer, kidney cancer, prostate caner, glioblastomas, metastatic melanomas, peritoneal or pleural mesotheliomas.

In some embodiments, the proliferative disease is a benign neoplasm. All types of benign neoplasms disclosed herein or known in the art are contemplated as being within the scope of the invention. In some embodiments, the proliferative disease is associated with angiogenesis. All types of angiogenesis disclosed herein or known in the art are contemplated as being within the scope of the invention. In certain embodiments, the proliferative disease is an inflammatory disease. All types of inflammatory diseases disclosed herein or known in the art are contemplated as being within the scope of the invention. In certain embodiments, the inflammatory disease is rheumatoid arthritis. In some embodiments, the proliferative disease is an autoinflammatory disease. All types of autoinflammatory diseases disclosed herein or known in the art are contemplated as being within the scope of the invention. In some embodiments, the proliferative disease is an autoimmune disease. All types of autoimmune diseases disclosed herein or known in the art are contemplated as being within the scope of the invention.

In certain embodiments, the methods described herein include administering to a subject with an effective amount of the Pt-BASPs described herein, or a pharmaceutical composition thereof. In certain embodiments, the methods described herein include implanting to a subject with an effective amount of the Pt-BASPs described herein, or a pharmaceutical composition thereof.

In certain embodiments, the Pt-BASPs described herein, or a pharmaceutical composition thereof, are administered in combination with one or more additional pharmaceutical agents described herein. In certain embodiments, the additional pharmaceutical agent is an anti-cancer agent. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), antimetabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine. In certain embodiments, the anti-cancer agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase Erwinia chrysanthemi (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPOX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), or zoledronic acid (e.g., ZOMETA).

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

EXAMPLES

In order that the invention described herein may be more fully understood, the following examples are set forth. It should be understood that these examples are for illustrative purposes only and are not to be construed as limiting this invention in any manner.

Materials and Methods

All reagents were purchased from commercial suppliers and used without further purification unless stated otherwise. Norbornene anhydride a2[1], dihydroxy oxaliplatin-Pt (IV) a1[2], Grubbs 3$^{rd}$ generation bispyridyl catalyst G3-Cat[3], PEG-MM[4], DOX-MMS, DOX-PC-MM[1], CPT-MM[1], Cy5.5-MM[6], CisPtXL[1], and AcetalXL[5] were prepared according to literature procedures. Liquid chromatography mass spectrometry (LC-MS) tandem was performed on a reverse-phase, C18-column using a binary solvent system (MeCN and H$_2$O with 0.1% CH$_3$COOH). Size exclusion chromatography (SEC) analyses were performed on an Agilent 1260 Infinity setup with two Shodex KD-806M columns in tandem and a 0.025 M LiBr DMF mobile phase run at 60° C. The differential refractive index (dRI) of each compound was monitored using a Wyatt Optilab T-rEX detector. Column chromatography was carried out on silica gel 60F (EMD Millipore, 0.040-0.063 mm). Nuclear magnetic resonance (NMR) spectra were recorded on Bruker AVANCE 111-400 spectrometer, with working frequencies of 400 (1H), 100 ($^{13}$C) and 86 ($^{195}$Pt) MHz, respectively. Chemical shifts are reported in ppm relative to the signals corresponding to the residual non-deuterated solvents: DMSO-$d_6$: 5H=2.50 and 5c=39.5 ppm. High-resolution mass spectra (HRMS) were measured on a Bruker Daltonics APEXIV 4.7 Tesla Fourier Transform Ion Cyclotron Resonance Mass Spectrometer (FT-ICR-MS) using an electrospray ionization (ESI) source. Dynamic light scattering (DLS) measurements were performed using a Wyatt Technology Mobius DLS instrument. Samples were prepared by diluting the stock solution (BASP nanoparticles were stored at 0° C. in THF to prevent aggregation) in either nanopure water (MilliQ) or 5% glucose solution (also in nanopure water); the resulting solutions were passed through a 0.4 m Nalgene filter (PES membrane) into disposable polystyrene cuvettes, which were pre-cleaned with compressed air. Measurements were made in sets of 10 acquisitions, and the average hydrodynamic diameters were calculated by fitting the DLS correlation function (Dynamics V7 software package from Wyatt Technology). TEM images were acquired using a FEI Tecnai Multipurpose TEM (G2 Spirit TWIN, 12 kV) at the MIT Center for Materials Science and Engineering. Sample preparation consisted of the following: 5 µL of a 1.0 mg/mL aqueous solution of BASP nanoparticles was pipetted onto a carbon film-coated 200-mesh copper grid (Electron Microscopy Sciences) placed on a piece of parafilm. Next, the aqueous solution was carefully absorbed at the base of the droplet using the edge of a Kimwipe, leaving behind the nanoparticles on the TEM grid. The samples were then stained negatively by adding a drop of 2 wt % uranyl acetate (Electronic Microscopy Sciences). After 5 min, the residual uranyl acetate solution was carefully absorbed onto a Kimwipe, and the samples were allowed to dry completely before analysis.

RNAi signatures were performed as described previously[2-4]. Briefly, Eµ-Myc p19$^{Arf-/-}$ lymphoma cells were infected at about 30% with GFP-tagged shRNAs. The cells were then treated with drug to kill 80-90% of cells as judged by propidium iodide exclusion via flow cytometry at 48 h. At 72 h, GFP positivity was assessed via flow cytometry. Constrained linear regression was performed in Stata using least-squares fit with individual drug treatments as the predictor variables and the combination signatures as the response variables. The linear regression was constrained such that the sum of the predictor variables had to equal one and none could be negative.

Cell Culture, shRNA Constructs

Animal Usage: All experiments involving animals were reviewed and approved by the MIT Committee for Animal Care (CAC). BALB/c mice (female, 12-16 weeks old) were used for toxicity and pharmacokinetic studies and for therapeutic efficacy study while receiving an alfalfa-free diet (TestDiet) to minimize auto-fluorescence. For statistical significance, all experiments were performed on groups of n=4+. Exclusion criteria included human error in BASP nanoparticle administration.

In Vivo Toxicity and Pharmacokinetics:

BASP nanoparticle solutions ranging from 1.0-6.0 mg/200 µL in 5% glucose solution/sterile pH 7.4 PBS buffer were prepared, passed through a sterile 0.2 m filter (Nalgene, PES membrane), and administered into BALB/c mice (n=4) via tail vein injection using a catheter. Adverse physical effects and weight loss were monitored, yielding an optimized dosage of 5.0 mg/200 µL. For pharmacokinetic study, BASP nanoparticle doses (4.5 mg/200 µL) were injected into BALB/c mice (3.0 groups of n=3), and blood samples were taken at 0, 0.25, 5, 24, and 48 h via cheek bleed. Samples were centrifuged to obtain blood serum, which were then subjected to fluorescence imaging (IVIS, Cy5.5 $\lambda_{ex}/\lambda_{em}$=640/700 nm, Xenogen). Additionally, tumor localization was monitored at 3 and 24 h, followed by euthanizing the mice and subjecting the excised organs to fluorescence imaging.

In Vivo Therapeutic Efficacy:

Ovarian cancer cells (SKOV-3; ATCC) were grown in RPMI-1640 media supplemented with 0.01 mg/mL bovine insulin, 20% fetal bovine serum in 5% $CO_2$ humidified atmosphere (37° C.) to a final concentration of 20%; cells were then harvested, mixed with Matrigel and sterile pH 7.4 PBS buffer, filtered through sterile 0.2 µm filters, and subcutaneously injected on the flanks of the mice. Tumor growth was monitored until 0.9 cm in cumulative diameter was reached. At this point, drug-loaded BASP nanoparticles were injected (5.0 mg/200 µL, weekly injections) to the treatment group (n=4) while the same amount of 5% glucose were administered to the control group (n=4) via tail vein injection. Tumor progression and therapeutic efficacy were monitored via IVIS imaging, caliber and/or ImageJ measurements. At set time-points, mice were taken out of the study for blood chemistry panel analysis, tumor and/or organ collection, followed by histology/pathology analysis.

In Vivo IVIS Imaging:

In vivo imaging was performed on an IVIS Spectrum-bioluminescent and fluorescent imaging system (Xenogen) at the Koch Institute for Integrative Cancer Research at MIT. Mice were anesthetized in isoflurane chamber for 10 min prior to imaging. Fluorescence imaging was acquired based on the Cy5.5 component of the BASP nanoparticles ($\lambda_{ex}/\lambda_{em}$=675/nm, exposure time 2-10 s).

Example 1: Oxaliplatin Crosslinker (OxPtXL): Synthetic Protocol

Figure 8:
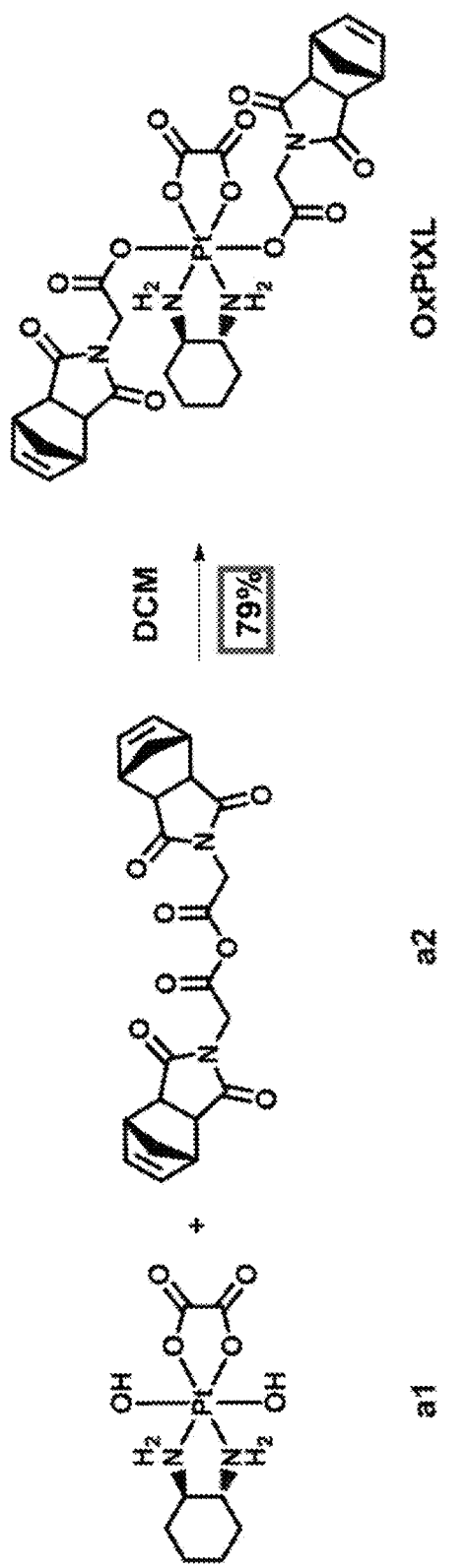
FIG. 8 shows the synthesis of an Oxaliplatin Crosslinker (OxPtXL).

Oxaliplatin Crosslinker (OxPtXL):

A modified procedure[1] was used in the synthesis of OxPtXL (FIG. 8). Norbonene anhydride a2 (551 mg, 1.3 mmol, 4.3 eq), and dihydroxy oxaliplatin-Pt(IV) a1 (129 mg, 0.3 mmol, 1.0 eq) were dissolved in anhydrous DCM (10 mL). The reaction mixture was allowed to stir under $N_2$ at room temperature for 2 weeks. The mixture was then centrifuged upon the addition of DCM (25 mL); the solid was collected, washed with ethyl acetate (30 mL×3), and followed by centrifugation (3,000 rpm, 7 min). The pure product was collected and dried under vacuum, yielding OxPtXL (197.6 mg, 79%) as a white solid. HRMS-ESI: Calcd for $C_{30}H_{34}N_4O_{12}Pt$: m/z=860.1712 [M+Na]$^+$; Found: 860.1713 [M+Na]$^+$. $^1$H NMR (400 MHz, DMSO-$d_6$, ppm) $\delta_H$ 8.28 (d, J=8.7 Hz, 2H), 7.78 (t, J=11.2 Hz, 2H), 6.31 (s, 4H), 4.17 (s, 4H), 3.10 (s, 4H), 2.71 (s, 4H), 2.55 (br, 2H), 2.09 (d, J=11.0 Hz, 2H), 1.53 (d, J=9.5 Hz, 4H), 1.44 (br, 2H), 1.33-1.31 (d, J=9.6 Hz, 2H), 1.22-1.09 (m, 2H). $^{13}$C NMR (100 MHz, $d_6$-DMSO, ppm): $\delta_C$ 176.9, 172.5, 163.7, 137.8, 60.6, 47.3, 44.6, 42.6, 30.7, 23.6 (FIG. 11). $^{195}$Pt NMR (86 MHz, $d_6$-DMSO, ppm): $\delta_{Pt}$ 1660.5 (FIG. 12).

Example 2: Procedure for Brush-Arm Star Polymer (BASP) Syntheses

All BASP syntheses were performed in a glovebox under a $N_2$ atmosphere; however, similar results are expected under ambient conditions. All ROMP reactions followed the same general procedure, which was modified from previously published literature[1,5].

Figure 9A:
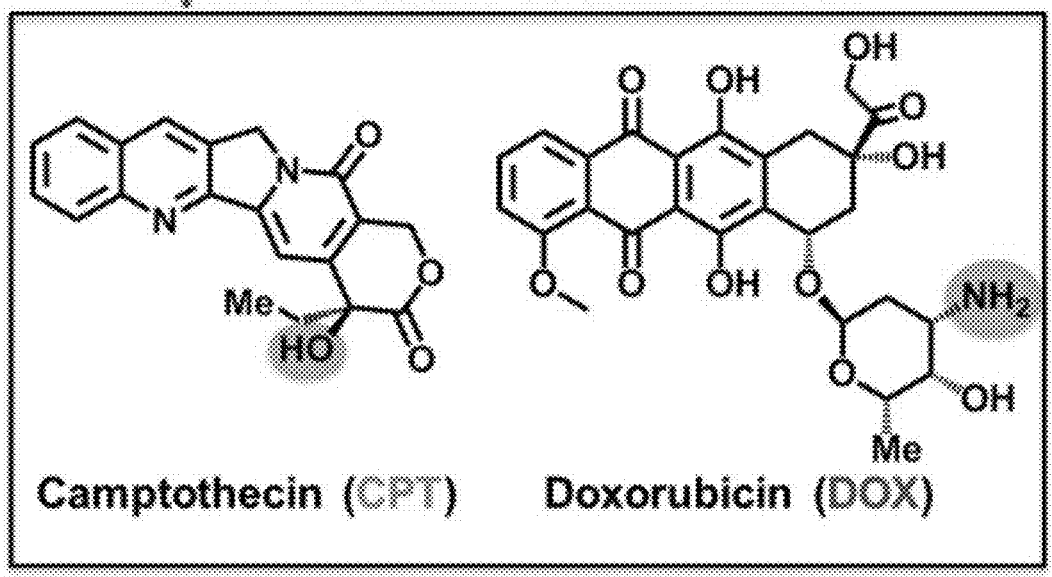
FIGS. 9A to 9C show chemical structures of: i) topoisomerase I/II inhibitors, camptothecin (CPT) and doxorubicin (DOX) (FIG. 9A); ii) DNA crosslinkers/intercalators, cisplatin (cisPt) and oxaplatin (oxPt) (FIG. 9B); and iii) various macromonomer (MM)-crosslinkers (XL) (FIG. 9C).
Figure 9B:
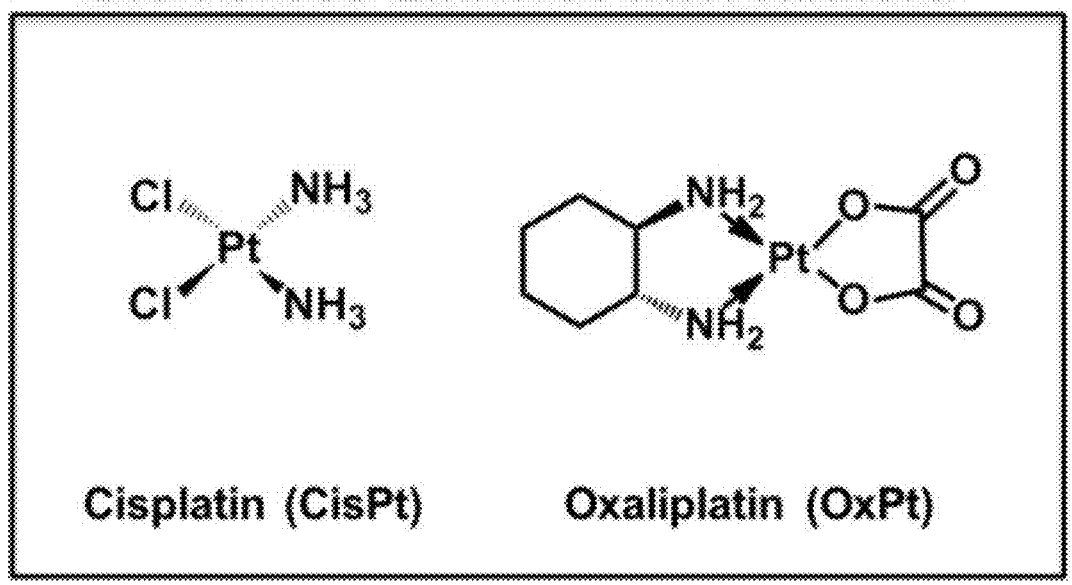
Figure 9C:
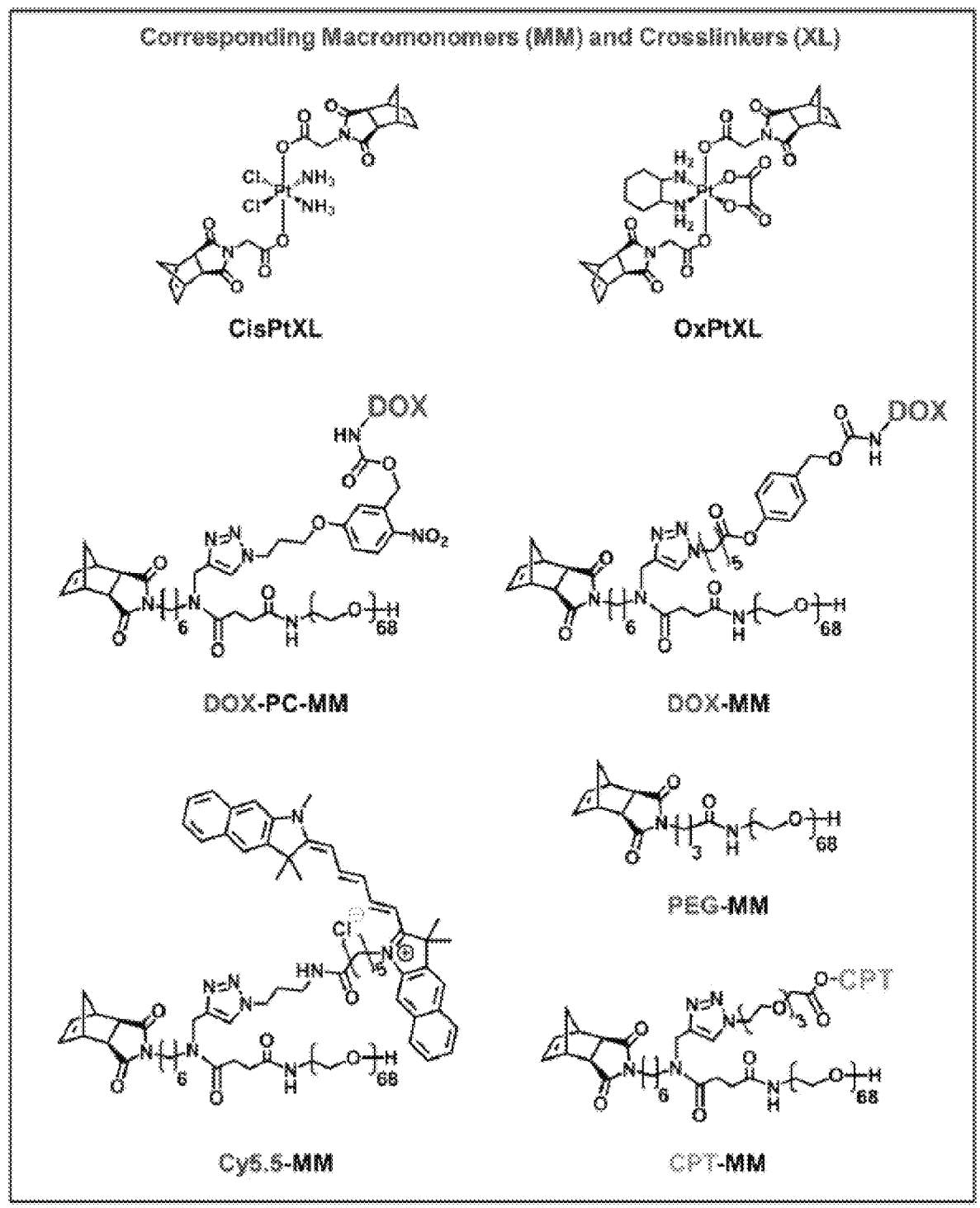

Chemical Structures of all Macromonomers (MMs) and Crosslinkers (XLs):

The chemical structures of macromonomers (MMs) and crosslinkers (XLs) used are shown in FIGS. 9A to 9C. The highlighted functional groups of CPT and DOX indicate where the drug is conjugated to the MM.

General Scheme for Brush Polymerization and Crosslinking to Form BASPs:

The general scheme for the synthesis of the reported drug-loaded brush, followed by cross-linking with the bis-norbornene functionalized Pt(IV) prodrug to afford brush-arm star polymers (BASPs) is shown in FIG. 10.

Cisplatin(cisPt)-Doxorubicin(DOX)-Camptothecin(CPT) Nanoparticles:

The general scheme for the synthesis of cisPt-DOX-CPT nanoparticles is shown in FIG. 22.

CPT-Loaded BASP (NP-CPT):

To a 4 mL vial, a suspension of AcetalXL (5.70 mg, 9.80 µmol, 15.0 eq) in THF (98.0 µL, 0.1 M AcetalXL) was prepared. To a second 4 mL vial containing a stir bar, CPT-MM (3.56 mg, 0.91 µmol, 1.4 eq) and PEG-MM (20.00 mg, 5.63 mol, 8.6 eq) were added. To a third vial, a solution of Grubbs $3^{rd}$ generation bispyridyl catalyst G3-Cat (0.02 M in THF) was freshly prepared. THF (33.0 µL) was then added to the MM vial, followed by the addition of the G3-Cat solution (32.7 µL, 0.65 µmol, 1.0 eq) to give the desired MM:G3-Cat ratio of 10:1, while achieving a total MM concentration of 0.1 M, affording a yellow solution. The reaction mixture was allowed to stir for 20 min at room temperature before an aliquot (~10 µL) was taken out and quenched with 1 drop of ethyl vinyl ether for GPC analysis. Next, the AcetalXL suspension was added into the MM vial in three aliquots (~5 equiv. each addition) until the desired 15.0 equiv. were added, and the polymerizing mixture was allowed to stir for 1 h at room temperature, affording a brown solution. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchanged every 6 h). The BASP nanoparticles were stored in THF at 0° C. (FIG. 13B).

DOX-Loaded BASP (NP-DOX):

To a 4 mL vial, a suspension of AcetalXL (5.70 mg, 9.80 µmol, 15.0 eq) in THF (98.0 µL, 0.1 M AcetalXL) was prepared. To a second 4 mL vial containing a stir bar, DOX-MM (3.80 mg, 0.91 µmol, 1.4 eq) and PEG-MM (20.00 mg, 5.63 µmol, 8.6 eq) were added. To a third vial, a solution of Grubbs $3^{rd}$ generation bispyridyl catalyst G3-Cat (0.02 M in THF) was freshly prepared. THF (33.0 µL) was then added to the MM vial, followed by the addition of the G3-Cat solution (32.7 µL, 0.65 µmol, 1.0 eq) to give the desired MM:G3-Cat ratio of 10:1, while achieving a total MM concentration of 0.1M, affording a red solution. The reaction mixture was allowed to stir for 20 min at room temperature before an aliquot (~10 µL) was taken out and quenched with 1 drop of ethyl vinyl ether for GPC analysis. The AcetalXL suspension was then added into the MM vial in three aliquots (5 equiv. each addition) until the desired 15.0 equiv. were added, and the polymerizing mixture was allowed to stir for 1 h at room temperature, affording a red solution. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. (FIG. 13C).

OxPt-Loaded BASP (NP-OxPt):

To a 4 mL vial containing a stir bar, OxPtXL (3.82 mg, 4.57 µmol, 5.0 eq) was added. To a second 4 mL vial containing a stir bar, PEG-MM (30.00 mg, 9.13 µmol, 10.0 eq) were added. To a third vial, a solution of Grubbs $3^{rd}$ generation bispyridyl catalyst G3-Cat (0.02 M in THF) was freshly prepared. THF (136.9 µL) was then added to the MM vial, followed by the addition of the G3-Cat solution (45.6 µL, 0.91 µmol, 1.0 eq) to give the desired MM:G3-Cat ratio of 10:1, while achieving a total MM concentration of 0.05M, affording a yellow solution. The reaction mixture was allowed to stir for 20 min at room temperature before an aliquot (~10 µL) was taken out and quenched with 1 drop of ethyl vinyl ether for GPC analysis. The polymerizing mixture was then transferred (163 µL) to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. (FIG. 13A). The $DTE_M$ for the NP-OxPt BASP nanoparticles was determined to be 34±8 nM.

PEG BASP (NP-PEG):

To a 4 mL vial, a suspension of AcetalXL (23.50 mg, 40.5 tmol, 14.3 eq) in THF (405 µL, 0.1 M AcetalXL) was prepared. To a second 4 mL vial containing a stir bar, PEG-MM (65.00 mg, 19.80 µmol, 7.0 eq) was added. To a third vial, a solution of Grubbs $3^{rd}$ generation bispyridyl catalyst G3-Cat (0.02 M in THF) was freshly prepared. THF (100 µL) was then added to the MM vial, followed by the addition of the G3-Cat solution (98.0 µL, 2.82 µmol, 1.0 eq) to give the desired MM:G3-Cat ratio of 7:1, while achieving a total MM concentration of 0.1M, affording a yellow solution. The reaction mixture was allowed to stir for 20 min at room temperature before an aliquot (~10 µL) was taken out and quenched with 1 drop of ethyl vinyl ether for GPC analysis. The AcetalXL suspension was then added dropwise (in 3 aliquots of ~130 µL) over the course of 10 min into the MM vial, and the polymerizing mixture was allowed to stir for 3 h at room temperature, affording a brown solution. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. (FIG. 13D).

CPT-DOX-CisPt BASP (NP-3D-CisPt):

To a 4 mL vial containing a stir bar, CisPtXL (0.82 mg, 1.12 µmol, 3.0 eq) was added. To a second 4 mL vial containing a stir bar, CPT-MM (3.01 mg, 0.77 µmol, 2.1 eq), DOX-MM (1.27 mg, 0.31 µmol, 0.8 eq), and PEG-MM (5.00 mg, 1.52 µmol, 4.1 eq) were added. To a third vial, a solution of Grubbs $3^{rd}$ generation bispyridyl catalyst G3-Cat (0.02 M in THF) was freshly prepared. THF (33.4 µL) was then added to the MM vial, followed by the addition of the G3-Cat solution (18.6 µL, 0.37 µmol, 1.0 eq) to give the desired MM:G3-Cat ratio of 7:1, while achieving a total MM concentration of 0.05M, affording a red solution. The reaction mixture was allowed to stir for 20 min at room temperature before an aliquot (~10 µL) was taken out and quenched with 1 drop of ethyl vinyl ether for GPC analysis. The polymerizing mixture was then transferred to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C.

CPT-DOX-PC-OxPt BASP (NP-3D-PC-OxPt):

To a 4 mL vial containing a stir bar, OxPtXL (7.42 mg, 8.86 μmol, 5.0 eq) was added. To a second 4 mL vial containing a stir bar, CPT-MM (24.00 mg, 6.13 μmol, 3.5 eq), DOX-PC-MM (10.27 mg, 2.46 μmol, 1.4 eq), and PEG-MM (30.00 mg, 9.13 μmol, 5.2 eq) were added. To a third vial, a solution of Grubbs $3^{rd}$ generation bispyridyl catalyst G3-Cat (0.02 M in THF) was freshly prepared. THF (266 μL) was then added to the MM vial, followed by the addition of the G3-Cat solution (88.4 μL, 1.77 μmol, 1.0 eq) to give the desired MM:G3-Cat ratio of 10:1, while achieving a total MM concentration of 0.05M, affording a red solution. The reaction mixture was allowed to stir for 20 min at room temperature before an aliquot (~10 μL) was taken out and quenched with 1 drop of ethyl vinyl ether for GPC analysis. The polymerizing mixture was then transferred (334 μL) to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. The $D_H$ for the NP-3D-PC-OxPt BASP nanoparticles was determined to be 16±3 nM.

CPT-Diluted DOX-PC-OxPt BASP (NP-3D-DD-OxPt):

To a 4 mL vial containing a stir bar, OxPtXL (7.66 mg, 9.14 μmol, 5.0 eq) was added. To a second 4 mL vial containing a stir bar, CPT-MM (35.77 mg, 9.14 μmol, 5.0 eq), DOX-PC-MM (0.0763 mg, 0.0183 μmol, 0.01 eq), and PEG-MM (30.00 mg, 9.13 μmol, 4.99 eq) were added. To a third vial, a solution of Grubbs $3^{rd}$ generation bispyridyl catalyst G3-Cat (0.02 M in THF) was freshly prepared. THF (274 μL) was then added to the MM vial, followed by the addition of the G3-Cat solution (91.9 μL, 1.83 μmol, 1.0 eq) to give the desired MM:G3-Cat ratio of 10:1, while achieving a total MM concentration of 0.05M, affording a yellow solution. The reaction mixture was allowed to stir for 20 min at room temperature before an aliquot (~10 μL) was taken out and quenched with 1 drop of ethyl vinyl ether for GPC analysis. The polymerizing mixture was then transferred (346 L) to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. The $D_{TEM}$ for the NP-3D-DD-OxPt BASP nanoparticles was determined to be 57±33 nM and the $D_H$ was determined to be 37±21 nM.

CPT-DOX-OxPt BASP (NP-3D-OxPt):

To a 4 mL vial containing a stir bar, OxPtXL (7.63 mg, 9.11 μmol, 5.0 eq) was added. To a second 4 mL vial containing a stir bar, CPT-MM (24.66 mg, 6.30 μmol, 3.5 eq), DOX-MM (10.59 mg, 2.53 μmol, 1.4 eq), and PEG-MM (30.00 mg, 9.38 μmol, 5.2 eq) were added. To a third vial, a solution of Grubbs $3^{rd}$ generation bispyridyl catalyst G3-Cat (0.02 M in THF) was freshly prepared. THF (273 μL) was then added to the MM vial, followed by the addition of the G3-Cat solution (91.0 μL, 1.82 μmol, 1.0 eq) to give the desired MM:G3-Cat ratio of 10:1, while achieving a total MM concentration of 0.05M, affording a red solution. The reaction mixture was allowed to stir for 20 min at room temperature before an aliquot (~10 μL) was taken out and quenched with 1 drop of ethyl vinyl ether for GPC analysis. The polymerizing mixture was then transferred (344 μL) to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. (FIGS. 23C to 23D).

CPT-DOX-OxPt-Cy5.5 BASP (NP-3D-OxPt-Cy5.5):

To a 4 mL vial containing a stir bar, OxPtXL (7.82 mg, 9.34 μmol, 5.0 eq) was added. To a second 4 mL vial containing a stir bar, CPT-MM (25.30 mg, 6.46 μmol, 3.5 eq), DOX-MM (10.86 mg, 2.60 μmol, 1.4 eq), Cy5.5-MM (1.00 mg, 0.25 μmol, 0.13 eq), and PEG-MM (30.00 mg, 9.38 μmol, 5.0 eq) were added. To a third vial, a solution of Grubbs $3^{rd}$ generation bispyridyl catalyst G3-Cat (0.02 M in THF) was freshly prepared. THF (275 μL) was then added to the MM vial, followed by the addition of the G3-Cat solution (93.4 μL, 1.87 μmol, 1.0 eq) to give the desired MM:G3-Cat ratio of 10:1, while achieving a total MM concentration of 0.05M, affording a dark brown solution. The reaction mixture was allowed to stir for 20 min at room temperature before an aliquot (~10 μL) was taken out and quenched with 1 drop of ethyl vinyl ether for GPC analysis. The polymerizing mixture was then transferred to the XL vial, and the solution was allowed to stir for 6 h at room temperature. To quench the polymerization, a drop of ethyl vinyl ether was then added. The newly formed nanoparticles were transferred to an 8 kD MW cutoff dialysis tubing (Spectrum Laboratories) in 5 mL THF, and the solution was dialyzed against THF (500 mL×3, solvent exchange every 6 h). The BASP nanoparticles were stored in THF at 0° C. (FIGS. 23A to 23B).

Free Drug Combination (DOX-CPT-OxPt): A stock solution of free DOX and CPT at 0.50 mg/mL (DOX) and 0.79 mg/mL (CPT) in 5% glucose was prepared. To a second vial, a free OxPt stock solution (24.75 mg/mL) in DMSO was prepared. The OxPt solution was diluted 20-fold with the DOX-CPT solution, forming the final free drug solution with 0.47 mg/mL DOX, 0.75 mg/mL CPT, and 1.24 mg/mL OxPt. The final solution contained 5% DMSO; the net amount and composition of drug delivered was matched to the BASP system at 200 μL injections.

General Scheme for Iterative Exponential Growth+ Analysis:

A general scheme analysis for the IEG+ is shown in FIG. 27.

Analysis of Homopolymer Blocks:

A general synthesis of homopolymer blocks was performed, resulting in a 32-unit polymer (FIG. 28A). Analysis was then performed using MALDI (FIG. 28B), gel permeation chromatography (GPC) (FIG. 28C), and $^1$H NMR (FIG. 28D).

Analysis of Alternating Copolymer Blocks:

A general synthesis of alternating copolymer blocks was performed with further analysis done using MALDI and GPC (FIG. 29).

Example 3: RNAi Signature Assay

Heat Map and Principle Component Analysis of UV-Stimulated and Diluted DOX NPs: A signature assay heat map (FIG. 14A) illustrating the effect that UV-triggered release of DOX has on the mechanism of action of the three-drug-loaded nanoparticle is shown. The principal components were further analyzed using a principal component analysis (FIG. 14B).

RNAi Signatures and Classification of Individual Free Drugs, Prodrugs, and Nanoparticles:

Eμ-Myc p19$_{Arf-/-}$ lymphoma cells were infected at about 30% with GFP-tagged shRNAs. The cells were then treated with drug to kill 80-90% of cells as judged by propidium iodide exclusion via flow cytometry at 48 h. At 72 h GFP positivity was assessed via flow cytometry. Using the RNAi signature approach, the free drug, prodrug, single-drug-conjugated BASPs, and multi-drug conjugated BASPs illustrated in FIGS. 9A-9C were characterized. The signature assay of native DOX and prodrugs DOX-MM and NP-DOX classified (FIG. 20A) each species as a Topoisomerase II (Top2) poison. Furthermore, CPT, CPT-MM, and NP-CPT were all classified (FIG. 20B) as Topoisomerase I (Top1) poisons. Unexpectedly, the prodrugs CisPtXL and NP-CisPt were classified (FIG. 20C) as new categories not represented in the reference set, and not as DNA cross-linkers, the anticipated mechanism of action of free cisplatin. This observation indicates that prodrugs and/or NPs are capable of altering a drug's expected mechanism of action. In contrast, the free drug OxPt (a CisPt derivative comprised of bidentate ligands), OxPtXL, and the NP-OxPt classified similarly (FIG. 20D), namely as transcription/translation inhibitors. Hence, the deviation of CisPtXL and NP-CisPt from the known free drug mechanism of action is not an occurrence common to all Pt(IV)-based chemotherapeutic prodrugs investigated with the RNAi signature assay. Next, the RNAi signatures for each of the free drugs and their corresponding prodrug monomers and BASPs were plotted (FIG. 20E) using principal component analysis (PCA). PCA is a means of representing the variance in a multi-dimensional dataset in fewer dimensions. This plot indicates that the CisPtXL and NP-CisPt are both more similar to the transcription/translation inhibitors than to the DNA cross-linkers. One hypothesis that may explain the observed difference between the cisplatin and oxaliplatin prodrug mechanisms is related to the ligand lability of these species. Inside the cell, where the concentration of chloride ions is much lower than in the extracellular milieu (2 to 30 mM for the former compared to ~100 mM for the latter), the weakly bound chloride ligands of free cisplatin are replaced with aquo ligands. This diaquo species induces cytotoxic inter- or intra-strand DNA cross-links. In the case of the cisplatin prodrugs disclosed herein, it is possible that the axial norbornene-carboxylate ligand that is released upon intracellular reduction re-binds to an equatorial position of the platinum center, thus, forming a carboxylate-Pt(II) complex rather than the expected diaquo complex. This altered ligand composition could then generate monofunctional DNA adducts as opposed to completely cross-linked ones. In the case of OxPtXL prodrug, the bidentate carboxylate ligands may be able to out-compete the norbornene-based carboxylates that result from the reduction of the Pt(IV) prodrug. Therefore, no changes in the mechanism of action of OxPtXL or NP-OxPt would be observed using the RNAi signature assay. This hypothesis is supported by a comparison of the corresponding Pt(II) release profiles (FIG. 15) associated with each NP in the presence of GSH. The release of platinum from NP-OxPt plateaus at approximately 75 days, whereas release of platinum from NP-CisPt never plateaus within the scope of a 270 day investigation, thus, suggesting that platinum remains bound to the polymeric carrier. Additionally, utilizing a CisPt-DNA adduct specific antibody, the genomic DNA isolated from murine lymphoma cells after 8 h of drug treatment was analyzed. It was observed that Cisplatin-DNA adducts are only detected (FIG. 13A-D) as a result of CisPt treatment, and not CisPtXL, further confirming the lack of expected bifunctional adduct formation from CisPtXL. As an additional functional validation of the RNAi signature results, DOX and CPT free drug, as well as NP-DOX and NP-CPT, were also tested with validated Top1 and Top2A shRNAs via a GFP competition assay. Knockdown of Top1 elicited resistance to the Top1 poison CPT and sensitivity to the Top2 poison DOX. The inverse was true for knockdown of Top2A: cells harboring the Top2A shRNA were resistant to free DOX and exhibited sensitivity to free CPT. These results were recapitulated for the respective BASPs, specifically NP-CPT and NP-DOX, where each BASP produced (FIG. 20F) similar RNAi signatures as their corresponding free drugs CPT and DOX, respectively.

Contribution of Different Drugs to Mechanism of Action of Combination Nanoparticles as Predicted by Constrained Linear Regression:

Constrained linear regression was performed in Matlab 2015a using the 'lsqlin' function with individual drug treatments as the predictor variables and the combination signatures as the response variables. The linear regression was constrained such that the sum of the predictor variables had to equal one and none could be negative. This was repeated for all combinations of replicates for both the response and predictor variables. This resulted in a minimum of 120 individual linear regressions. The results of all regressions were then averaged to obtain the final result. Error is the standard error of the mean of all of the regressions. In order to use RNAi-based signatures to determine the relative effective contribution of multiple drugs within a single NP, a BASP capable of externally triggered drug release was designed to easily validate the presence or absence of the triggered drug in a combination of other drugs without having to change the BASP composition. For this, CPT-MM and photocleavable DOX-PC-MM were crosslinked with OxPtXL via BF-ROMP to yield 3-drug-conjugated BASP NP-3D-PC-OxPt. The incorporation of the UV-triggered DOX-PC-MM allows for rapid release of free DOX upon exposure to 365 nm light. NP-3D-PC-OxPt was used to treat cells either with or without light irradiation and RNAi signatures were obtained. Constrained linear regression was then performed (FIGS. 14-A and 21A) on the RNAi signatures to ascertain the relative effective contributions of each drug's mechanism of action between the UV-irradiated and non-irradiated BASP treatments. As anticipated, the signatures obtained in the absence of light irradiation showed (FIG. 21A, 'no UV') that free DOX was not predicted to have contributed to the mechanism of action of the NP, as determined by constrained linear regression. Conversely, constrained linear regression predicted (FIG. 21A, 'UV') that free DOX contributed to the UV-irradiated NP mechanism of action at approximately 55%. Then, the mechanism of action of two novel BASPs were analyzed that either contained DOX-PC-MM diluted to ~0.2% of the amount used in NP-3D-PC-OxPt (NP-3D-DD-OxPt, where DD=Diluted DOX), or possessed the non-photo-cleavable DOX-MM (NP-3D-OxPt). In both of these cases, regardless of treatment with UV light, constrained linear regression was able to identify (FIGS. 14A-B and 21B-C) the contribution of free DOX to the combined mechanism of action.

Example 4: Histology

Comparison of H&E Stained Liver Cross Sections of Treated and Untreated Mice:

Different views of paraffin-embedded and H&E stained liver cross sections were obtained from control mice (FIG. 15, top panel), nanoparticle-treated mice starting with tumors possessing 1 cm and 0.5 cm diameters (FIG. 15, middle panel), and free drug treated mice (FIG. 15, bottom panel).

Comparison of H&E Stained Tumor Cross Sections of Treated and Untreated Mice:

Different views of paraffin-embedded and H&E stained left (L) and right (R) tumor cross sections were obtained from control mice (FIG. 16, top panel), nanoparticle-treated mice starting with tumors possessing 1 cm and 0.5 cm diameters (FIG. 16, middle panel), and free drug treated mice (FIG. 16, bottom panel).

Comparison of H&E Stained Tumor and Liver Cross Sections of Treated and Untreated Mice:

Different views of H&E stained left (L) and right (R) tumor cross sections obtained from a control mouse (FIG. 26, top panel), H&E stained liver cross sections obtained from acute and chronic mice (FIG. 26, middle panel), and H&E stained right (R) tumor cross sections obtained from acute and chronic mice (FIG. 26, bottom panel).

Example 5: Blood Chemistry Analysis

Pharmacokinetics of OxPt-Loaded BASP (NP-OxPt): Pharmacokinetics over a 126 h period associated with NP-OxPt containing 1% Cy5.5-MM injected (4.5 mg/dose; 18 mg/kg) in BALB/c mice are shown in FIG. 17A. Tumor localization in NCR-NU mice injected with NP-OxPt containing 1% Cy5.5-MM is shown in FIG. 17B.

Blood Panel Analysis of Nanoparticle/Free-Drug Treated and Control NCR-NU Mice:

Blood panel analysis of biomarkers associated with NCR-NU mice treated with: i) NP-3D-OxPt (#114 bars: Chronic; #19 bars: Acute); ii) the free drug combination (#5 bars: DOX-CPT-OxPt); and iii) 5% glucose solutions is shown in FIG. 18. B/C=BUN/Creatinine.

Example 6: In Vivo Efficacy

Animal Usage:

All experiments involving animals were reviewed and approved by the MIT Committee for Animal Care (CAC). BALB/c mice (female, 8-12 weeks old, Taconic) were used for toxicity and pharmacokinetic studies. NCR-NU nude mice (female, 8-12 weeks old, Taconic) were used for biodistribution and therapeutic efficacy studies while receiving an alfalfa-free diet (TestDiet) to minimize auto-fluorescence. For statistical significance, all experiments were performed on groups of n=4+.

Tumor Volume Plot, Survival Curve, and Nanoparticle Localization in 1 cm Diameter Tumor Study:

Ovarian cancer cells (SKOV-3; ATCC) were grown in RPMI-1640 media supplemented with 0.01 mg/mL bovine insulin, 20% fetal bovine serum in 5% $CO_2$ humidified atmosphere (37° C.) to a final concentration of 20%. The cells were then harvested, mixed with Matrigel and sterile pH 7.4 PBS buffer (1:1), filtered through sterile 0.2 µm filters, and injected subcutaneously (1.25×106 cells) in the hind flanks of the mice. Tumor growth was monitored for 2-4 wks until either 0.5 or 1.0 cm in cumulative diameter was reached as the starting point for the two efficacy studies, after which treatment groups were randomized. At this point, three-drug-loaded BASP nanoparticles (NP-3D-OxPt) were injected (5.0 mg/200 µL, approx. weekly injections) to the treatment group (n=4+), while the same volume of 5% glucose was administered to the control group (n=4+) via tail vein injection. Tumor progression and therapeutic efficacy were monitored via caliper and ImageJ measurements.

At set time-points, mice were removed from the study for blood chemistry panel analysis (Charles River), tumor and/or organ excision, followed by histology and pathology analysis. Non-sacrificial mice were removed from the study if one or more of the following criteria were met: i) body weight decreased by 10% or more compared to the body weight at the start of the study, ii) the diameter of the tumor doubled compared to the starting diameter (i.e., if starting with 0.5 cm diameter, then the mouse was removed at 1.0 cm; or if starting at 1.0 cm, then the mouse was removed at 2.0 cm in diameter), or iii) development of necrotic, and/or cracked and bleeding tumor tissue. As discussed above, tumor localization of NP-3D-OxPt-Cy5.5 was investigated by injecting NCR-NU mice with 5 mg of the three-drug-loaded nanoparticle and monitoring (excitation at 675 nm; emission at 720 nm) the epifluorescence at 3 and 20 h in an IVIS whole animal imaging system (FIG. 19A). Tumor volume plot and treatment schedule for the in vivo efficacy study of mice possessing 1 cm in diameter subcutaneous xenograft tumors are shown in FIG. 19B. FIG. 19C shows the survival curve illustrating the survival probability of the nanoparticle treated mice versus the control mice that were only injected with 5% glucose solutions.

Tumor Volume Plot, Survival Curve, and Nanoparticle Localization in 0.5 cm Diameter Tumor Study:

To investigate the therapeutic efficacy of the three-drug-loaded NP-3D-OxPt in vivo, NCR-NU mice were injected subcutaneously in each hind flank with 1.25×106 ovarian carcinoma cells (SKOV-3, ATCC) mixed (1:1) with Matrigel and PBS buffer. Tumor growth was monitored for 2-4 wks until the tumor reached approximately 0.5 cm in diameter, at which point three treatment groups were established: those treated with sterile-filtered 5% aqueous glucose solutions containing either i) NP-3D-OxPt, ii) a free drug formulation at the same DOX, CPT, and OxPt concentrations as NP-3D-OxPt, or iii) the blank vehicle. The BASP treatment schedule consisted of four tail-vein injections over 22 days (~1 inj./wk), where each injection per mouse comprised of 5 mg BASP in 200 µL of 5% glucose solution, a dose that is close to the maximum solubility limit (~6 mg/200 µL) of the three-drug-conjugated BASP. Since ~10% of each NP-3D-OxPt is made up of the three anti-cancer drugs, each dose is equal to ~20 mg total drug/kg mouse. Although the ratio of drug loading in NP-3D-OxPt should afford maximum tolerable doses (MTD) that match those of free DOX and CPT, and more than twice that of OxPt, the results from the RNAi signature assay suggest that, at least in vitro, the effective contribution from all three drugs toward the overall mechanism of action should be nearly equal. Simultaneous delivery of all three drugs within one BASP entity ensures that the three drugs will arrive at the tumor in a ratio defined by the BASP, which precludes differences in pharmacokinetics and biodistribution that could be observed for mixtures of single-drug-conjugated NPs. Thus, results obtained at the cell culture level can be expected to translate to the tumor. As a consequence of the branched MM design, the BASP possesses a protective PEG outer layer, a feature that greatly enhances its bioavailability and leads to a blood circulation half-life ($t_{1/2}$) of 43±8 h for NP-OxPt in NCR-NU mice (FIG. 14A-B). This increased circulation in the bloodstream allows sufficient time for passive accumulation of the BASPs in tumors (FIGS. 14A-B, 19A-B, and 24A), a process which occurs within 20-24 h post-injection by way of the enhanced permeability and retention (EPR) effect. A qualitative biodistribution analysis of NP-OxPt loaded with 1% Cy5.5-MM fluorophore reveals (FIG. 15) tumor and liver accumulation after 24 h, followed by excretion of the residual NP in the mouse feces after 48 h. The mice treated with the free drug formulation lost significant total body mass after only two treatments (FIG. 24D) and therefore had to be euthanized, with their blood serum and tissues harvested for post-therapeutic analysis. The BASP treatment group, however, displayed (FIG. 24D) excellent therapeutic tolerance, as evidenced by a consistent total body mass and no noticeable adverse effects throughout the course of the study. The tumor volume progression plot illustrates (FIG. 24B) a clear regression in tumor growth associated with the BASP treatment group, whereas the mice in the vehicle control group showed no signs of tumor regression. After the fourth and final BASP treatment, both the BASP treatment and the vehicle groups showed a continued increase of tumor volumes though the tumors in the former case grew at a slower rate. The survival rate of each treatment group reflects (FIG. 24C) the overall therapeutic tolerance and efficacy associated with the BASP combination therapy, whereas the mice from the vehicle control group were removed as deemed necessary, according to the criteria established in our Committee on Animal Care protocol. After completion of the 60-day therapeutic efficacy study, the surviving mice from the BASP treatment group were sacrificed and their blood serum and organs were harvested in order to perform a blood panel analysis (FIG. 17B). This allowed for comparison of toxicity between the post-study chronically treated mice, the mid-study acutely treated mice, and vehicle mice. As anticipated, the acutely and chronically treated mice associated with the BASP treatment group demonstrated little to no kidney damage as evidenced by the low blood urea nitrogen to creatinine ratio, as well as very low amounts of liver damage-related biomarkers, such as alanine and aspartate aminotransferases (FIG. 17B). Pathology of the paraffin-embedded, H&E-stained cross-sections (~5 m thick) of the livers (FIG. 18) from the BASP-treated and vehicle mice supports this biomarker quantification analysis. Cross-sections of the paraffin-embedded, H&E-stained tumors harvested from acute/chronic BASP-treated mice show (FIGS. 19A-C) strong evidence of cancer cell death in direct contrast to the healthy vehicle control tumor tissue. To assess the degree to which our NP-3D-OxPt dose could demonstrate efficacy in larger tumors from the same cancer cell line, we carried out another in vivo therapeutic efficacy study starting (FIGS. 19A-C) with tumors ~1.0 cm in diameter and observed comparable therapeutic tolerance and efficacy relative to the results from the first study.

Tumor Reduction:

Nearly complete tumor reduction was observed in Mouse #105 over a 21 day treatment schedule and 12 week observation using CPT-DOX-OxPt (FIG. 25).

Discussion

It has been demonstrated that a modular BASP combination therapy platform—comprised of drug-conjugated MMs and Pt(IV)-based XLs—is an effective means of delivering a precise ratio of an otherwise toxic combination of three drugs to a subcutaneous xenograft tumor in mice. Previously, there was no way to verify that the drug mechanism of action was not disrupted by incorporation into the nanoparticle. The mechanism of action associated with the reported prodrugs and single-drug-loaded BASPs was characterized using an RNAi signature assay that allows for a fast and accurate in vitro combinatorial screening that is capable of predicting a prodrug's mechanism of action. Although the Pt(IV)-diester XL—intended to be a precursor to CisPt—did not behave as anticipated in vitro, the RNAi signatures allowed the identification of another Pt(IV)-diester XL that functions as a faithful precursor to OxPt. Thus, a functional genetic assay was employed to ensure that the conjugated drugs—whose mechanistic targets differ from one another—behaved as intended. Moreover, constrained linear regression analysis, paired with RNAi signatures, revealed the relative effective contributions of each drug towards the mechanism of action in our three-drug-conjugated BASPs. The ability to assess the in vitro contribution of each drug adds another layer of quality control to NP-based drug delivery. The initial stoichiometric ratios can be tuned to achieve BASPs where all drugs contribute equally, or BASPs that possess disparate drug contributions that may potentially maximize synergistic ratios, all the while taking into account the kinetics associated with the release of each drug from the combination NP platformThis modular platform and the RNAi-based mechanism of action predictive assay can be further utilized to assess different combinations of drugs in an effort to treat other types of cancer, as well as characterize nanoparticles other than BASPs consisting of one, two, three, or potentially more drugs.

REFERENCES

[1] Liao, L.; Liu, J.; Dreaden, E. C.; Morton, S. W.; Shopsowitz, K. E.; Hammond, P. T.; Johnson, J. A. J. Am. Chem. Soc. 2014, 136, 5896-5899.

[2] Hall, M.; Dillon, C.; Zhang, M.; Beale, P.; Cai, Z.; Lai, B.; Stampfl, A. J.; Hambley, T. J. Biol. Inorg. Chem. 2003, 8, 726-732.

[3] Love, J. A.; Morgan, J. P.; Trnka, T. M.; Grubbs, R. H. Angew. Chem. Int. Ed. 2002, 41, 4035-4037.

[4] Liu, J.; Burts, A. O.; Zhukhovitsky, A. V.; Ottaviani, M. F.; Turro, N. J.; Johnson, J. A. J. Am. Chem. Soc. 2012, 134, 16337-16344

[5] Gao, A. X.; Liao, L.; Johnson, J. A. ACS Macro Lett. 2014, 3, 854-857.

[6] Sowers, M. A; McCombs, J. R.; Wang, Y.; Paletta, J. T.; Morton, S. W.; Dreaden, E. C.; Boska, M. D.; Ottaviani, M. F.; Hammond, P. T.; Rajca, A.; Johnson, J. A. Nature Commun. 2014, 5, 5460.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. It is also noted that the term "including" is intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Thoses killed in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A polymer prepared by the steps of:
   (a) reacting a first macromonomer of Formula (III'):

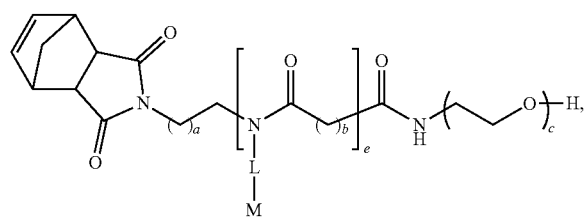

or a salt thereof, with a second macromonomer of Formula (III'), or a salt thereof, in the presence of a metathesis catalyst to provide a polymerization mixture, wherein:
   a is an integer from 1 to 10, inclusive;
   each instance of b is independently an integer from 1 to 10, inclusive;
   c is an integer from 1 to 200, inclusive;
   e is 0, 1, 2, 3, 4, 5, or 6;
   each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O) NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, a polymer, or a substituted or unsubstituted C$_{1-30}$ hydrocarbon chain, optionally wherein one or more carbon units of the hydrocarbon chain is independently replaced with substituted or unsubstituted phenyl, substituted or unsubstituted triazolyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O) NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, substituted or unsubstituted C$_{1-10}$ alkyl, or a nitrogen protecting group, and wherein each occurrence of R$^{Lb}$ is independently selected from the group consisting of hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{Lb}$ groups are joined to form a substituted or unsubstituted carbocyclic or substituted or unsubstituted heterocyclic ring, or R$^{La}$ and R$^{Lb}$ are joined to form an substituted or unsubstituted heterocyclic ring;

each instance of M is independently hydrogen or a pharmaceutical agent, wherein the pharmaceutical agent is a small molecule, a protein, a peptide, a polynucleotide, a glycoprotein, or a lipoprotein; wherein: the molecular weight of the small molecule is not more than 2,000 g/mol; and the polynucleotide is DNA or RNA; and the first macromonomer and the second macromonomer are the same or different from each other; and (b) contacting the polymerization mixture with a platinum complex of Formula (I):

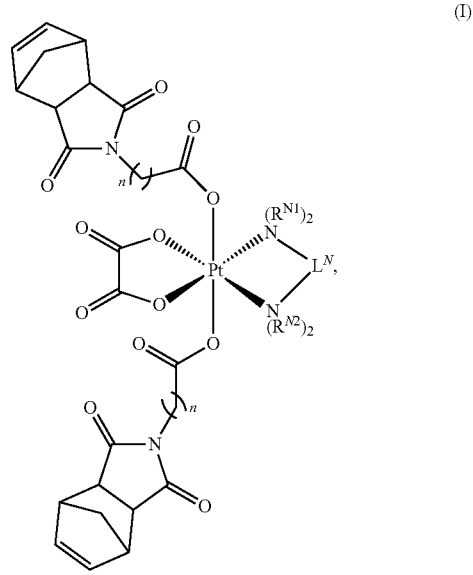

or a salt thereof, to provide the polymer, wherein:
   each instance of R$^{N1}$ is independently hydrogen, substituted or unsubstituted C$_{1-6}$ alkyl, or a nitrogen protecting group, or two R$^{N1}$ are taken with the intervening atoms to form a heterocyclic ring;

each instance of $R^{N2}$ is independently hydrogen, substituted or unsubstituted $C_{1-6}$ alkyl, or a nitrogen protecting group, or two $R^{N2}$ are taken with the intervening atoms to form a heterocyclic ring;

$L^N$ is a linker selected from the group consisting of substituted or unsubstituted alkylene, substituted or unsubstituted heteroalkylene, substituted or unsubstituted arylene, substituted or unsubstituted heteroarylene, substituted or unsubstituted cycloalkylene, substituted or unsubstituted heterocyclylene, and combinations thereof; and each instance of n is 1, 2, 3, 4, 5, or 6.

2. The polymer of claim 1, wherein at least one instance of L is a substituted or unsubstituted $C_{1-30}$ hydrocarbon chain, wherein one or more carbon units of the hydrocarbon chain is independently replaced with substituted or unsubstituted phenyl, substituted or unsubstituted triazolyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR—, S(=O)$_2$O, —OS(=O)$_2$—, —S(=O)$_2$NR$^{La}$—, or —NR$^{La}$S(=O)$_2$—.

3. The polymer of claim 1, wherein at least one instance of L is a substituted or unsubstituted $C_{1-30}$ hydrocarbon chain, wherein:
one or more carbon units of the hydrocarbon chain is replaced with substituted or unsubstituted triazolyl; and
optionally one or more carbon units of the hydrocarbon chain is independently replaced with substituted or unsubstituted phenyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—.

4. The polymer of claim 1,
wherein:
each instance of b is independently an integer from 1 to 5, inclusive;
c is an integer from 1 to 100, inclusive;
e is 0, 1, 2, 3, or 4;
each instance of L is independently —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, —NR$^{La}$S(=O)$_2$—, a peptide, or a substituted or unsubstituted $C_{1-10}$ hydrocarbon chain, optionally wherein one or more carbon units of the hydrocarbon chain is replaced with —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—, wherein each instance of R$^{La}$ is independently hydrogen, substituted or unsubstituted $C_{1-10}$ alkyl, or a nitrogen protecting group, and wherein each occurrence of R$^{Lb}$ is independently selected from the group consisting of hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{Lb}$ groups are joined to form a substituted or unsubstituted carbocyclic or substituted or unsubstituted heterocyclic ring, or R$^{La}$ and R$^{Lb}$ are joined to form a substituted or unsubstituted heterocyclic ring.

5. The polymer of claim 1, wherein e is 1.

6. The polymer of claim 1, wherein c is an integer from 30 to 100, inclusive.

7. The polymer of claim 1, wherein at least one instance of L is of the formula:

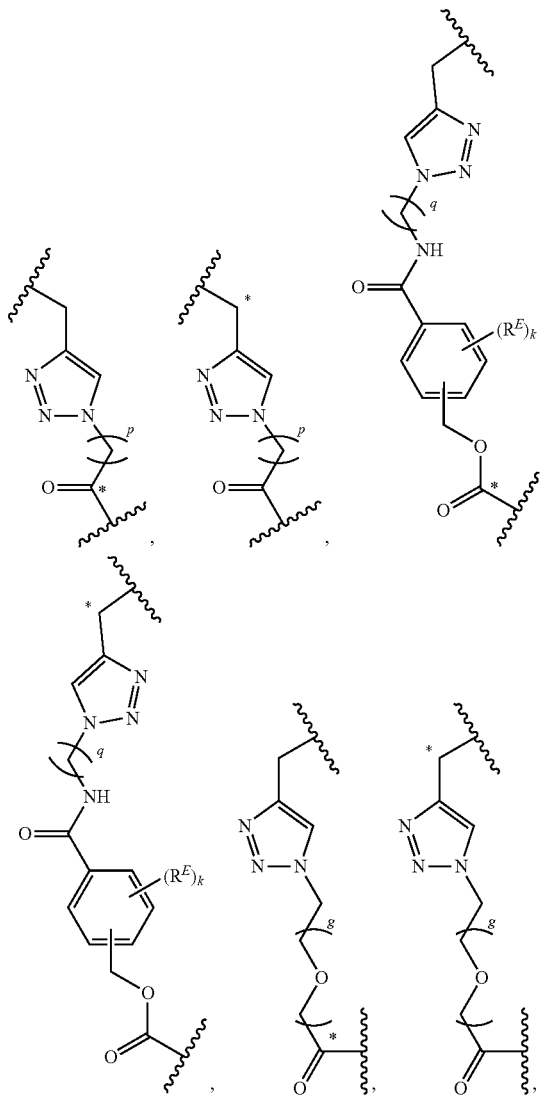

-continued

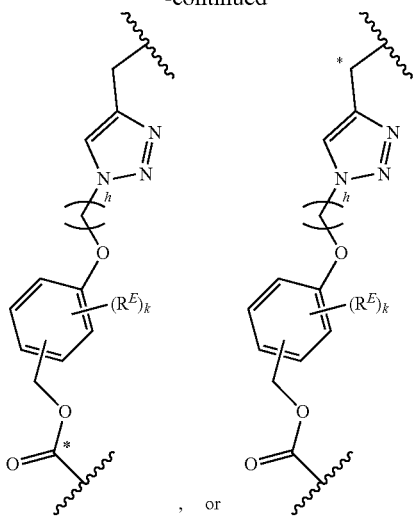

, or wherein:
each instance of the carbon atom labeled with "*" is attached to M;
each instance of $R^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —N(R$^a$)C(=O)R$^a$, —N(R$^a$)C(=O)OR$^a$, —N(R$^a$)C(=O)N(R$^a$)$_2$, —N(R$^a$)S(=O)R$^a$, —N(R$^a$)S(=O)OR$^a$, —N(R$^a$)S(=O)N(R$^a$)$_2$, —N(R$^a$)S(=O)$_2$R$^a$, —N(R$^a$)S(=O)$_2$OR$^a$, —N(R$^a$)S(=O)$_2$N(R$^a$)$_2$, —OC(=O)R$^a$, —OC(=O)OR$^a$, or —OC(=O)N(R$^a$)$_2$;
each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ are joined to form a substituted or unsubstituted, heterocyclic ring, or substituted or unsubstituted, heteroaryl ring;
each instance of k is independently 0, 1, 2, 3, or 4;
each instance of p is independently an integer from 1 to 10, inclusive;
each instance of q is independently an integer from 1 to 10, inclusive;
each instance of g is independently an integer from 1 to 10, inclusive; and
each instance of h is independently an integer from 1 to 10, inclusive.

8. The polymer of claim 1, wherein at least one instance of the macromonomer is of Formula (III-e):

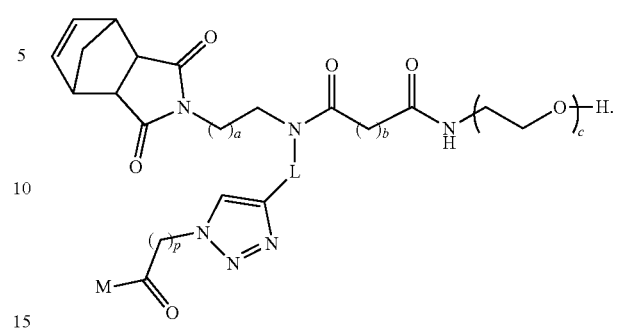

9. The polymer of claim 1, wherein at least one instance of the macromonomer is of Formula (III-f) or (III-h):

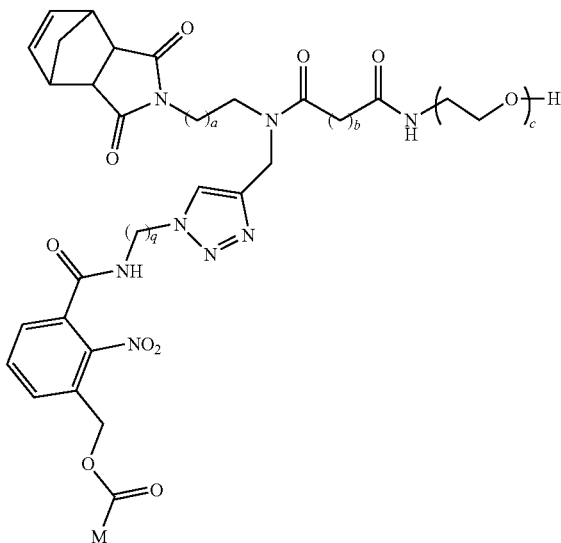

or

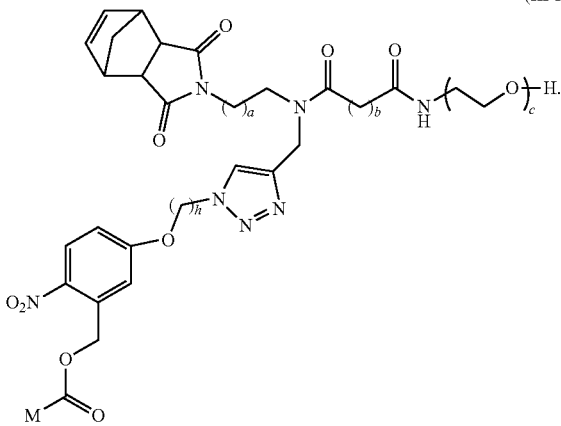

10. The polymer of claim 1, wherein at least one instance of the macromonomer is of Formula (III-g):

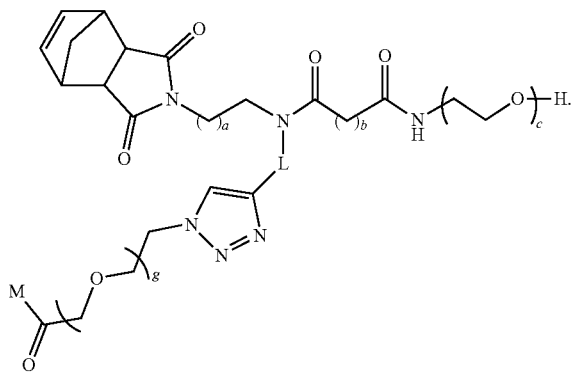

(III-g)

11. The polymer of claim 1, wherein at least one instance of M is a pharmaceutical agent.

12. The polymer of claim 1, wherein at least one instance of M is an anti-cancer agent, wherein the anti-cancer agent is a small molecule, a protein, a peptide, a polynucleotide, a glycoprotein, or a lipoprotein.

13. The polymer of claim 1, wherein at least one instance of M is of the formula:

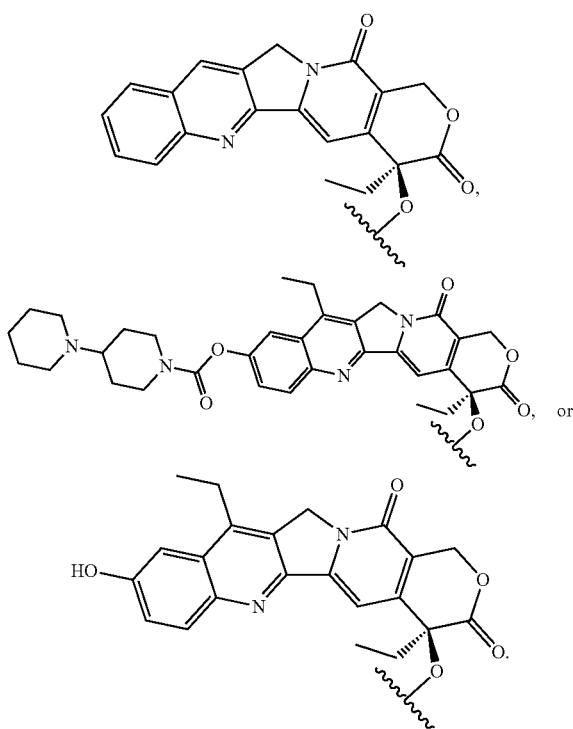

14. A pharmaceutical composition comprising a polymer of claim 11 and optionally a pharmaceutically acceptable excipient.

15. A kit comprising:
a container, wherein the container comprises a polymer of claim 1; and
instructions for using the polymer.

16. A method of treating cancer in a subject in need thereof comprising administering to the subject in need thereof an effective amount of a polymer of claim 12, wherein the cancer is acoustic neuroma, adenocarcinoma, adrenal gland cancer, anal cancer, angiosarcoma, appendix cancer, benign monoclonal gammopathy, biliary cancer, bladder cancer, breast cancer, brain cancer, bronchus cancer, carcinoid tumor, cervical cancer, choriocarcinoma, chordoma, craniopharyngioma, colorectal cancer, connective tissue cancer, epithelial carcinoma, ependymoma, endotheliosarcoma, endometrial cancer, esophageal cancer, eye cancer, familiar hypereosinophilia, gall bladder cancer, gastric cancer, gastrointestinal stromal tumor, germ cell cancer, head or neck cancer, hematopoietic cancer, hemangioblastoma, hypopharynx cancer, inflammatory myofibroblastic tumor, immunocytic amyloidosis, kidney cancer, liver cancer, lung cancer, leiomyosarcoma, mastocytosis, muscle cancer, myelodysplastic syndrome, mesothelioma, myeloproliferative disorder, neuroblastoma, neurofibroma, neuroendocrine cancer, bone cancer, ovarian cancer, papillary adenocarcinoma, pancreatic cancer, penile cancer, pinealoma, primitive neuroectodermal tumor, plasma cell neoplasia, paraneoplastic syndromes, intraepithelial neoplasms, prostate cancer, rectal cancer, rhabdomyosarcoma, salivary gland cancer, skin cancer, small bowel cancer, soft tissue sarcoma, sebaceous gland carcinoma, small intestine cancer, sweat gland carcinoma, synovioma, testicular cancer, thyroid cancer, urethral cancer, vaginal cancer, or vulvar cancer.

17. A method of delivering a pharmaceutical agent to a subject comprising administering to the subject a polymer of claim 11.

18. A method of delivering a pharmaceutical agent to a biological sample, tissue, or cell, the method comprising contacting the biological sample, tissue, or cell with a polymer of claim 11.

19. The polymer of claim 1, wherein the platinum complex is of Formula (I-a):

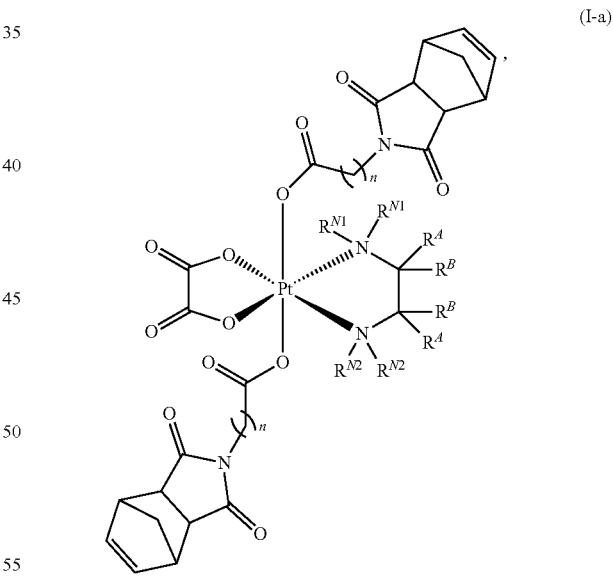

(I-a)

or a salt thereof, wherein:
each instance of $R^A$ is independently hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl; and
each instance of $R^B$ is independently hydrogen, halogen, substituted or unsubstituted alkyl, substituted or unsubstituted carbocyclyl, substituted or unsubstituted heterocyclyl, substituted or unsubstituted aryl, or substituted or unsubstituted heteroaryl;

or two instances of $R^B$ are joined to form a substituted or unsubstituted, carbocyclic ring, or substituted or unsubstituted, heterocyclic ring.

20. The polymer of claim 19, wherein the platinum complex is of Formula (I-b):

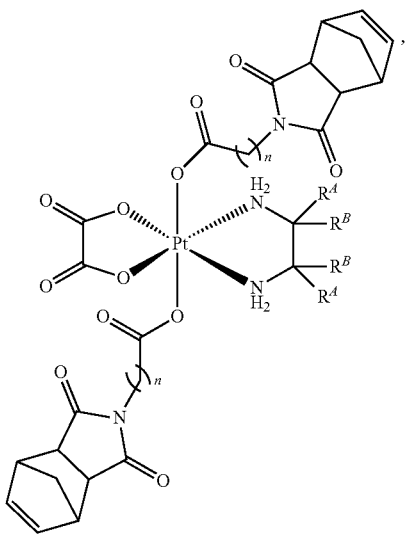

(I-b)

or a salt thereof.

21. The polymer of claim 19, wherein the platinum complex is of Formula (I-c):

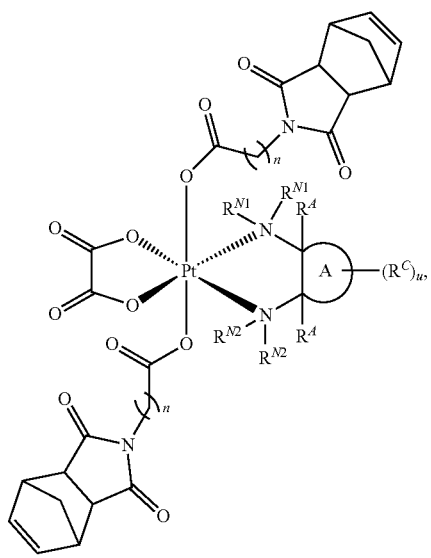

(I-c)

or a salt thereof, wherein:
Ring A is a substituted or unsubstituted, monocyclic, 3- to 7-membered carbocyclic ring;
each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$N(R^a)$C(=O)$R^a$, —$N(R^a)$C(=O)$OR^a$, —$N(R^a)$C(=O)$N(R^a)_2$, —$N(R^a)$S(=O)$R^a$, —$N(R^a)$S(=O)$OR^a$, —$N(R^a)$S(=O)$N(R^a)_2$, —$N(R^a)$S(=O)$_2R^a$, —$N(R^a)$S(=O)$_2OR^a$, —$N(R^a)$S(=O)$_2N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted, heterocyclic ring, or substituted or unsubstituted, heteroaryl ring; and u is an integer between 0 and 8, inclusive.

22. The polymer of claim 21, wherein the platinum complex is of Formula (I-d):

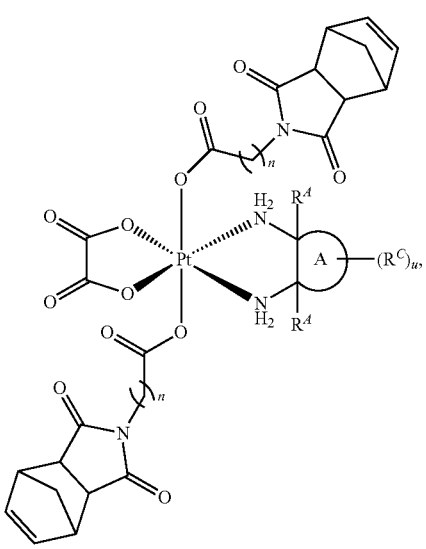

(I-d)

or a salt thereof.

23. The polymer of claim 21, wherein the platinum complex is of Formula (I-e):

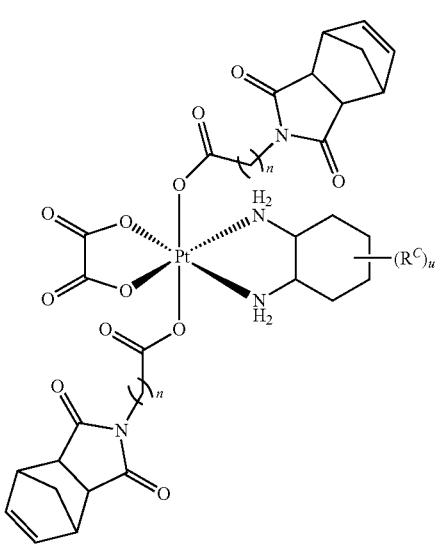

(I-e)

or a salt thereof.

24. The polymer of claim 1, wherein the platinum complex is of Formula (I-f):

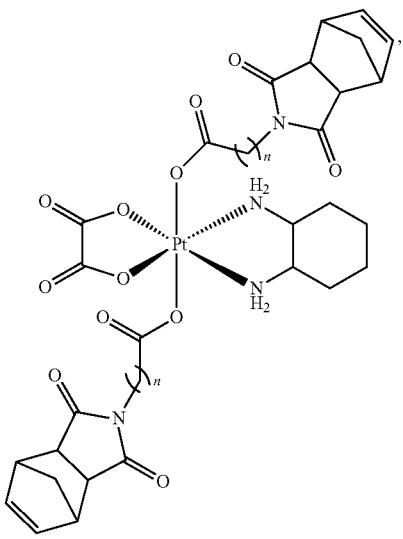

(I-f)

or a salt thereof.

25. The polymer of claim 1, wherein each instance of $R^{N1}$ is hydrogen, and each instance of $R^{N2}$ is hydrogen.

26. The polymer of claim 1, wherein $L^N$ is substituted or unsubstituted heterocyclylene or substituted or unsubstituted cycloalkylene.

27. The polymer of claim 1, wherein each instance of

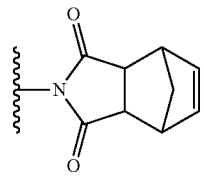 [SMILES: *N1C(=O)C2C3C=CC(C3)C2C1=O]

is

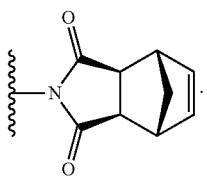 [SMILES: *N1C(=O)[C@@H]2[C@H](C1=O)[C@H]1C=C[C@@H]2C1]

28. The polymer of claim 1, wherein the platinum complex is of the formula:

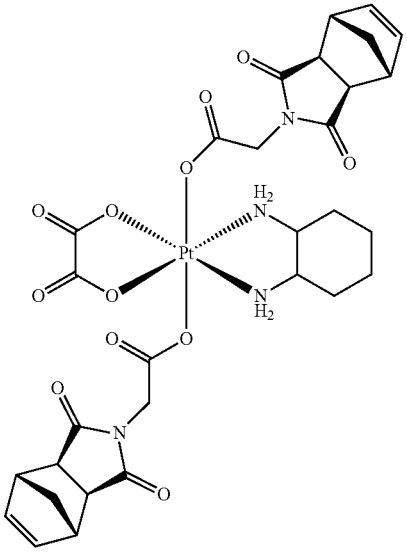

29. The polymer of claim 1, wherein at least one instance of L is a substituted or unsubstituted $C_{1-30}$ hydrocarbon chain, and wherein:
one carbon unit of the hydrocarbon chain is replaced with

wherein the nitrogen atom labeled with "*" is attached directly or indirectly to M;
one or more carbon units of the hydrocarbon chain are independently replaced with —SC(=O)—, —C(=O)S—, —OC(=O)—, —C(=O)O—, —OC(=O)O—, —OC(=O)NR$^{La}$—, —NR$^{La}$C(=O)O—, —S(=O)$_2$O—, or —OS(=O)$_2$—; and
optionally one or more carbon units of the hydrocarbon chain are independently replaced with substituted or unsubstituted phenyl, —O—, —S—, —NR$^{La}$—, —NR$^{La}$C(=O)—, —C(=O)NR$^{La}$—, —SC(=O)—, —C(=O)S—, —OC(=O)—, —C(=O)O—, —OC(=O)O—, —OC(=O)NR$^{La}$—, —NR$^{La}$C(=O)O—, trans-CR$^{Lb}$=CR$^{Lb}$—, cis-CR$^{Lb}$=CR$^{Lb}$—, —C≡C—, —OC(R$^{Lb}$)$_2$—, —C(R$^{Lb}$)$_2$O—, —NR$^{La}$C(R$^{Lb}$)$_2$—, —C(R$^{Lb}$)$_2$NR$^{La}$—, —S(=O)$_2$O—, —OS(=O)$_2$—, —S(=O)$_2$NR$^{La}$—, or —NR$^{La}$S(=O)$_2$—.

30. The polymer of claim 1, wherein at least one instance of M of the first macromonomer and at least one instance of M of the second macromonomer are different from each other.

31. The polymer of claim 12, wherein the anti-cancer agent is tumor necrosis factor, interferon α, interferon γ, IL-1, IL-2, IL-4, IL-6, IL-12, GM-CSF, trastuzumab, T-DM1, bevacizumab, cetuximab, panitumumab, rituximab, tositumomab, tamoxifen, raloxifene, megestrol, goscrclin, leuprolide, flutamide, bicalutamide, vertoporfin, phthalocyanine, photosensitizer Pc4, demethoxy-hypocrellin A, cyclophosphamide, ifosfamide, trofosfamide, chlorambucil, estramustine, melphalan, carmustine, lomustine, busulfan, treosulfan, dacarbazine, temozolomide, cisplatin, carboplatin, oxaliplatin, vincristine, vinblastine, vindesine, vinorelbine, paclitaxel, DHA-paclitaxel, taxoprexin, PG-paclitaxel, paclitaxel poliglumex, CT-2103, XYOTAX, Angiopep-2 bound to three molecules of paclitaxel, paclitaxel bound to the erbB2-recognizing peptide EC-1, 2'-paclitaxel methyl 2-glucopyranosyl succinate, docetaxel, taxol, etoposide, etoposide phosphate, teniposide, topotecan, 9-aminocamptothecin, camptoirinotecan, irinotecan, crisnatol, mytomycin C, methotrexate, dichloromethotrexate, trimetrexate, edatrexate, mycophenolic acid, tiazofurin, ribavirin, EICAR, hydroxyurea, deferoxamine, 5-fluorouracil, floxuridine, doxifluridine, ratitrexed, tegafur-uracil, capecitabine, cytarabine, cytosine arabinoside, fludarabine, mercaptopurine, thioguanine, EB 1089, CB 1093, KH 1060, lovastatin, 1-methyl-4-phenylpyridinium ion, staurosporine, actinomycin D, dactinomycin, bleomycin A2, bleomycin B2, peplomycin, daunorubicin, doxorubicin, pegylated liposomal doxorubicin, idarubicin, epirubicin, pirarubicin, zorubicin, mitoxantrone, verapamil, thapsigargin, imatinib, thalidomide, lenalidomide, axitinib, bosutinib, cediranib, AZD2171, dasatinib, erlotinib, gefitinib, lapatinib, lestaurtinib, neratinib, nilotinib, semaxanib, sunitinib, toceranib, vandetanib, vatalanib, ranibizumab, sorafenib, everolimus, alemtuzumab, gemtuzumab, ozogamicin, temsirolimus, ENMD-2076, PCI-32765, AC220, dovitinib lactate, BIBW 2992, SGX523, PF-04217903, PF-02341066, PF-299804, BMS-777607, ABT-869, MP470, BIBF 1120, AP24534, JNJ-26483327, MGCD265, DCC-2036, BMS-690154, CEP-11981, tivozanib, OSI-930, MM-121, XL-184, XL-647, XL228, bortezomib, rapamycin, ridaforolimus, AP23573, AZD8055, BEZ235, BGT226, XL765, PF-4691502, GDC0980, SF1126, OSI-027, oblimersen, gemcitabine, carminomycin, leucovorin, pemetrexed, prednisolone, dexamethasone, campathecin, plicamycin, asparaginase, aminopterin, methopterin, porfiromycin, leurosidine, leurosine, trabectedin, procarbazine, discodermolide, hexamethyl melamine, camptothecin, or SN-38.

* * * * *

UNITED STATES PATENT AND TRADEMARK OFFICE
CERTIFICATE OF CORRECTION

PATENT NO. : 10,792,373 B2
APPLICATION NO. : 16/167412
DATED : October 6, 2020
INVENTOR(S) : Jeremiah A. Johnson et al.

Page 1 of 1

It is certified that error appears in the above-identified patent and that said Letters Patent is hereby corrected as shown below:

In the Claims

In Claim 2, at Column 99, Line 26, please replace the text "–C($R^{Lb}$)$_2$NR–, S(=O)$_2$O" with the text -- –C($R^{Lb}$)$_2$N$R^{La}$–, –S(=O)$_2$O– --.

In Claim 7, at Column 101, Line 38, please replace the text "–N($R^a$)S(=)$_2$$R^a$" with the text -- –N($R^a$)S(=O)$_2$$R^a$ --.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*